US012662694B2

(12) United States Patent
Liu et al.

(10) Patent No.: US 12,662,694 B2
(45) Date of Patent: Jun. 23, 2026

(54) CRISPR-CAS12A REACTION FOR RAPID AND HIGHLY SENSITIVE ISOTHERMAL NUCLEIC ACID DETECTION

(71) Applicant: UNIVERSITY OF CONNECTICUT, Farmington, CT (US)

(72) Inventors: Changchun Liu, Farmington, CT (US); Xiong Ding, Farmington, CT (US)

(73) Assignee: UNIVERSITY OF CONNECTICUT, Farmington, CT (US)

(*) Notice: Subject to any disclaimer, the term of this patent is extended or adjusted under 35 U.S.C. 154(b) by 818 days.

(21) Appl. No.: 17/760,126

(22) PCT Filed: Mar. 17, 2021

(86) PCT No.: PCT/US2021/022760
§ 371 (c)(1),
(2) Date: Aug. 4, 2022

(87) PCT Pub. No.: WO2021/188669
PCT Pub. Date: Sep. 23, 2021

(65) Prior Publication Data
US 2024/0279718 A1 Aug. 22, 2024

Related U.S. Application Data

(60) Provisional application No. 63/054,318, filed on Jul. 21, 2020, provisional application No. 62/991,247, filed on Mar. 18, 2020.

(51) Int. Cl.
| | |
|---|---|
| *C12Q 1/682* | (2018.01) |
| *C12N 9/22* | (2006.01) |
| *C12Q 1/44* | (2006.01) |
| *C12Q 1/6844* | (2018.01) |

(52) U.S. Cl.
CPC .............. *C12Q 1/682* (2013.01); *C12N 9/22* (2013.01); *C12Q 1/44* (2013.01); *C12Q 1/6844* (2013.01)

(58) Field of Classification Search
CPC ........ C12Q 2521/507; C12Q 2531/119; C12Q 1/6818; C12Q 1/682; C12Q 1/6844
See application file for complete search history.

(56) References Cited

FOREIGN PATENT DOCUMENTS

| WO | 2019/104058 | 5/2019 |
|---|---|---|
| WO | 2020/006036 | 1/2020 |
| WO | 2020/028729 | 2/2020 |
| WO | 2020/142739 | 7/2020 |
| WO | 2020/142754 | 7/2020 |
| WO | 2020/257356 | 12/2020 |
| WO | 2021/092519 | 5/2021 |

OTHER PUBLICATIONS

Wang et al., "Cas12aVDet: A CRISPR/Cas12a-Based Platform for Rapid and Visual Nucleic Acid Detection," Analytical Chemistry, August, vol. 91, pp. 1215-12161. (Year: 2019).*
The International Search Report (ISR) for PCT/US2021/022760 dated Jul. 21, 2021, pp. 1-8.
Chen, Janice S. et al. "CRISPR-Cas12a target binding unleashes indiscriminate single-stranded DNase activity" Science (2018) vol. 360 (6387), pp. 436-439.
Chen, Janice S. et al. "Supplementary Materials for CRISPR-Cas12a target bind8ng unleashes indiscriminate single-stranded DNase activity" Apr. 27, 2019 Retrieved from the Internet: URL:https://science.sciencemag.org/content/sci/suppl/2018/02/14/science.aar6245.DC1/aar6245_Chen_SM_revision2.pdf [retrieved on Jun. 22, 2021].
Ding, Xiong et al. "Ultrasensitive and visual detection of SARS-CoV-2 using all-in-one dual CRISPR-Cas12a assay" Nature Communications (2020) vol. 11(1) [Online] Retrieved from the Internet: URL:http://www.nature.com/articles/s41467-020-18575-6>. the whole document.
Swarts, Daan C. et al. "Mechanistic Insights into the cis- and trans-Acting DNase Activities of Cas12a" Molecular Cell (2019) vol. 73(3), pp. 589-600.
Written Opinion of the International Searching Authority for PCT/US2021/022760 dated Jul. 21, 2021, pp. 1-7.

* cited by examiner

*Primary Examiner* — Young J Kim
(74) *Attorney, Agent, or Firm* — McDonnell Boehnen Hulbert & Berghoff, LLP

(57) ABSTRACT

The disclosure provides methods and compositions for All-In-One Dual CRISPR-Cas12a (termed "AIOD-CRISPR") permit simple, rapid, ultrasensitive, specific, one-pot and visual detection of nucleic acids (DNA and RNA).

18 Claims, 24 Drawing Sheets
Specification includes a Sequence Listing.

CRISPR-CAS12A REACTION FOR RAPID AND HIGHLY SENSITIVE ISOTHERMAL NUCLEIC ACID DETECTION

CROSS REFERENCE

This application is a U.S. national phase of International Application No. PCT/US2021/022760, filed on Mar. 17, 2021, which claims priority to U.S. Provisional Application No. 63/054,318, filed Jul. 21, 2020, and U.S. Provisional Application No. 62/991,247, filed Mar. 18, 2020, all of which are incorporated by reference herein in their entirety.

STATEMENT OF GOVERNMENT RIGHTS

This invention was made with government support under grant numbers TW010625, CA214072 and EB023607 awarded by the National Institutes of Health. The government has certain rights in the invention.

SEQUENCE LISTING STATEMENT

A computer readable form of the Sequence Listing is filed with this application by electronic submission and is incorporated into this application by reference in its entirety. The Sequence Listing is contained in the file created on Mar. 3, 2021 Aug. 4, 2022 having the file name "20-852-PCT_SeqList_ST25.txt" and is 3 kb in size.

SEQUENCE LISTING STATEMENT

A computer readable form of the Sequence Listing is filed with this application by electronic submission and is incorporated into this application by reference in its entirety. The Sequence Listing is contained in the file created on Mar. 3, 2021, having the file name "20-852-PCT_SeqList_ST25.txt" and is 3 kb in size.

BACKGROUND

Severe acute respiratory syndrome Coronavirus 2 (SARS-CoV-2, previously named 2019-nCoV) is a new coronavirus causing coronavirus disease 2019 (COVID-19) which first emerged in December 2019. Rapid and early detection of this deadly virus plays a critical role in facilitating early intervention and treatment, which, in turn, may reduce disease transmission risk. Polymerase chain reaction (PCR) method including its variant reverse transcription PCR (RT-PCR) is the most commonly used technology for pathogen nucleic acid detection. However, it typically relies on expensive equipment and well-trained personnel, as well as needs long assay reaction time (about 2 h), all of which is not suitable for simple, rapid, point of care (POC) molecular diagnostics of the SARS-CoV-2.

SUMMARY

In one aspect, the disclosure provides nucleic acid detection methods, comprising:
(a) incubating a sample with dNTPs, ATP, a forward primer and a reverse primer that are each complementary to a target nucleic acid, a single stranded DNA fluorophore quencher (ssDNA-FQ) comprising a fluorophore and a quencher, a strand displacement DNA polymerase, single-stranded DNA binding protein, and a recombinase to form a mixture;

wherein incubating the sample results in base pairing of the forward primer and the reverse primer to the target nucleic acid if present in the sample and initiation of recombinase polymerase amplification (RPA) of the target nucleic acid in the mixture, exposing binding sites for Cas12a-crRNA complexes due to strand displacement;
(b) incubating the mixture with:
(i) a forward Cas12a-crRNA complex and a reverse Cas12a-crRNA complex to form an assembled mixture, wherein the forward Cas12a-crRNA complex comprises a forward crRNA and Cas12a protein or functional analogue thereof, the reverse Cas12a-crRNA complex comprises a reverse crRNA and the Cas12a protein or functional analogue, wherein
(I) the forward crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the forward primer on the opposite strand from the forward primer; and
(II) the reverse crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the reverse primer on the opposite strand from the reverse primer; or
(ii) one or more Cas12a-crRNA complexes comprising a crRNA and Cas12a protein or functional analogue thereof to form an assembled mixture, wherein each of the one or more crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid between forward and reverse primer binding sites;
wherein all of the crRNAs in option (i) or (ii) each have a GC content of between about 50% and about 65%, and a melting temperature ($T_m$) of between about 56-65° C. using nearest neighbor method under the condition of 0.1 μM oligos and 1 M Na$^+$;
wherein none of the crRNAs include the protospacer adjacent motif (PAM) sequence TTTV;
wherein if the target nucleic acid is present in the mixture, incubating the mixture results in binding of either:
(I) the forward Cas12a-crRNA complex and the reverse Cas12a-crRNA complex to the binding sites for Cas12a-crRNA complexes on the target nucleic acid and Cas12a endonuclease activation and cleavage of ssDNA-FQ reporters to produce fluorescence; or
(II) the one or more Cas12a-crRNA complex to the binding sites for Cas12a-crRNA complexes on the target nucleic acid, and Cas12a endonuclease activation and cleavage of ssDNA-FQ reporters to produce fluorescence; and
(c) detecting fluorescence emitted from the assembled mixture, wherein fluorescence emission detection indicates presence of the target nucleic acid in the sample.
In another aspect, the disclosure provides compositions comprising:
(a) one or more containers comprising dNTPs, ATP, and optionally comprising a forward primer and a reverse primer that are each complementary to a target nucleic acid, a single stranded DNA fluorophore quencher (ssDNA-FQ) comprising a fluorophore and a quencher, a strand displacement DNA polymerase, single-stranded DNA binding protein, and a recombinase; and (b) a further container comprising
    (i) a forward Cas12a-crRNA complex comprising a forward crRNA and Cas12a protein or functional analogue thereof wherein the forward crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the forward primer on the opposite strand from the forward primer, and a reverse Cas12a-crRNA complex comprising a reverse crRNA and Cas12a protein or functional analogue thereof, wherein the reverse crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the reverse primer on the opposite strand from the reverse primer;
    (ii) a forward crRNA wherein the forward crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the forward primer on the opposite strand from the forward primer, a reverse crRNA wherein the reverse crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the reverse primer on the opposite strand from the reverse primer, and Cas12a protein or functional analogue thereof;
    (iii) one or more Cas12a-crRNA complexes comprising a crRNA and Cas12a protein or functional analogue thereof, wherein each of the one or more crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid between forward and reverse primer binding sites; or
    (iv) one or more crRNA and Cas12a protein or functional analogue thereof, wherein each of the one or more crRNA is between 10-100, 10-90, 10-80, 10-70, 10-60, 10-50, 1040, 10-30, 20-100, 20-90, 20-80, 20-70, 20-60, 20-50, 20-40, 20-30, or 20-24 nt in length, and is designed to bind to the target nucleic acid between forward and reverse primer binding sites;

wherein each crRNA has a GC content of between about 50% and about 65%, and a melting temperature ($T_m$) of between about 56-65° C. using nearest neighbor method under the condition of 0.1 μM oligos and 1 M $Na^+$; and wherein none of the crRNAs include the protospacer adjacent motif (PAM) sequence TTTV.

In one embodiment, the disclosure provides compositions comprising (a) a first container comprising dNTPs, ATP, and optionally comprising a forward primer and a reverse primer that are each complementary to a target nucleic acid, (b) a second container comprising a single stranded DNA fluorophore quencher (ssDNA-FQ) comprising a fluorophore and a quencher, a strand displacement DNA polymerase, single-stranded DNA binding protein, and a recombinase; and (c) a third container comprising
    (i) a forward Cas12a-crRNA complex comprising a forward crRNA and Cas12a protein or functional analogue thereof wherein the forward crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the forward primer on the opposite strand from the forward primer, and a reverse Cas12a-crRNA complex comprising a reverse crRNA and Cas12a protein or functional analogue thereof, wherein the reverse crRNA is between 10-100, 10-90, 10-80, 10-70, 10-60, 10-50, 1040, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the reverse primer on the opposite strand from the reverse primer;
    (ii) a forward crRNA wherein the forward crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the forward primer on the opposite strand from the forward primer, a reverse crRNA wherein the reverse crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the reverse primer on the opposite strand from the reverse primer, and Cas12a protein or functional analogue thereof;
    (iii) one or more Cas12a-crRNA complexes comprising a crRNA and Cas12a protein or functional analogue thereof, wherein each of the one or more crRNA is between 10-100, 10-90, 10-80, 10-70, 10-60, 10-50, 1040, 10-30, 20-100, 20-90, 20-80, 20-70, 20-60, 20-50, 20-40, 20-30, or 20-24 nt in length, and is designed to bind to the target nucleic acid between forward and reverse primer binding sites; or
    (iv) one or more crRNA and Cas12a protein or functional analogue thereof, wherein each of the one or more crRNA is between 10-100, 10-90, 10-80, 10-70, 10-60, 10-50, 1040, 10-30, 20-100, 20-90, 20-80, 20-70, 20-60, 20-50, 20-40, 20-30, or 20-24 nt in length, and is designed to bind to the target nucleic acid between forward and reverse primer binding sites;

wherein each crRNA has a GC content of between about 50% and about 65%, and a melting temperature ($T_m$) of between about 56-65° C. using nearest neighbor method under the condition of 0.1 μM oligos and 1 M $Na^+$; and wherein none of the crRNAs include the protospacer adjacent motif (PAM) sequence TTTV.

DETAILED DESCRIPTION

Figure 1:
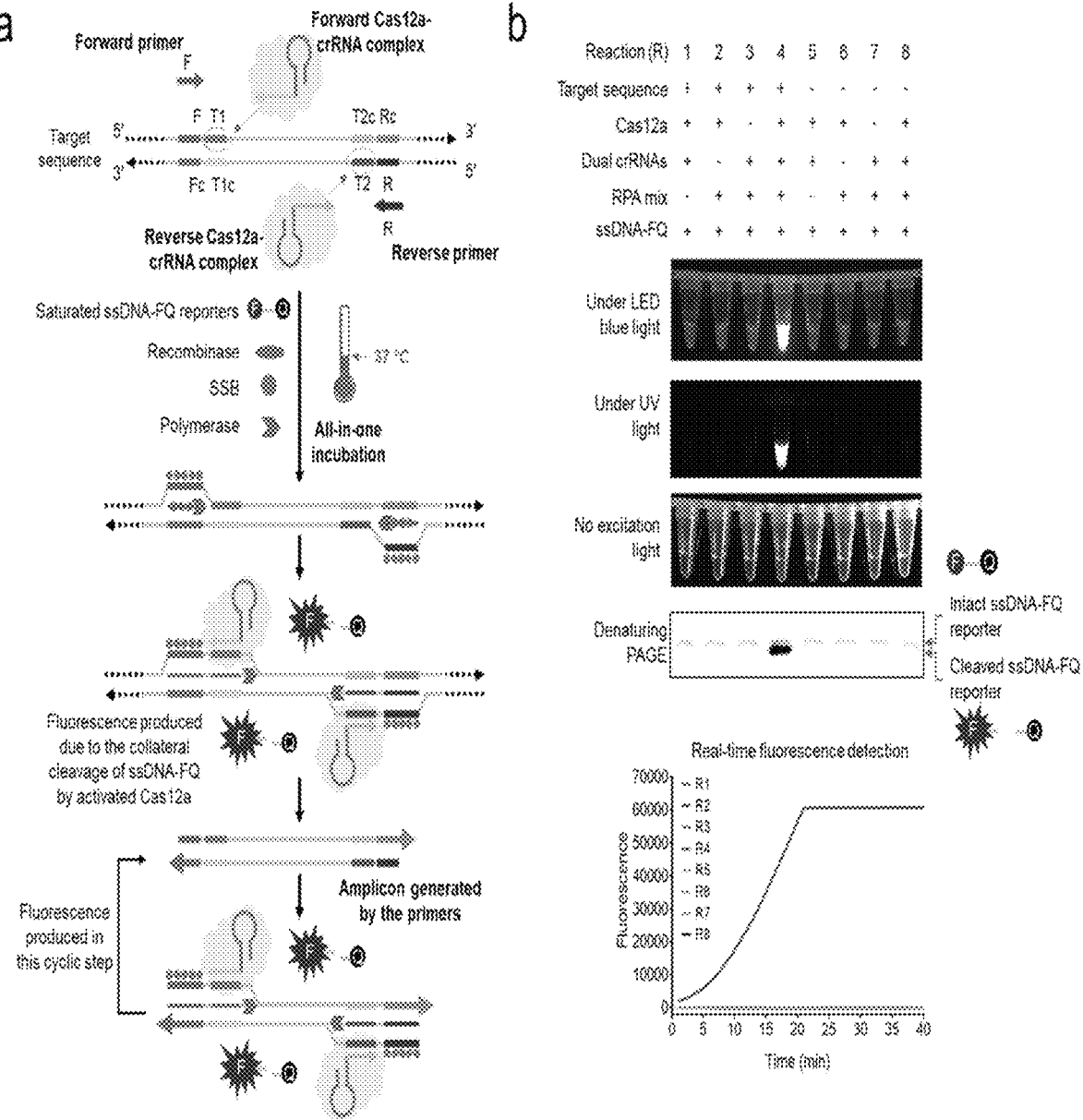
FIG. 1a-b. Design and working principle of the AIOD-CRISPR assay. a Schematic of the AIOD-CRISPR assay system. SSB, single-stranded DNA binding protein. The four sites in the target sequence are labeled as F, T1, T2, and R, respectively. The letter c represents the corresponding complementary site. For example, F and Fc sites are complementary. The short horizontal lines with the same colors denote the same sites and their arrows represent the direction of 5'-3'. b Evaluation of eight AIOD-CRISPR reactions (R) with various components through endpoint imaging after 40-min incubation, denaturing polyacrylamide gel electrophoresis (PAGE) analysis of the single-stranded fluorescent reporter (ssDNA-FQ), and real-time fluorescence detection. The ssDNA-FQ was labelled by 5'6-FAM (Fluorescein) fluorophore and 3' Iowa Black™ FQ quencher. Recombinase polymerase amplification (RPA) mix from Twist-Amp™ Liquid Basic kit was composed of 1× Reaction Buffer, 1× Basic E-mix, 1× Core Reaction Buffer, 14 mM MgOAc, 320 nM each of primers and 1.2 mM dNTPs. Dual crRNAs contained 0.64 µM each of crRNAs specific to the SARS-CoV-2 N gene sequence. A plasmid containing the SARS-CoV-2 N gene sequence ($3×10^3$ copies), 8 µM of ssDNA-FQ reporters, and 1.28 µM EnGen Lba™ Cas12a (Cpf1) were used. Each experiment was repeated three times with similar results.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', "comprising", and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

As used herein, "about" means+/−5% of the recited parameter.

All embodiments of any aspect of the invention can be used in combination, unless the context clearly dictates otherwise.

In a first aspect, the disclosure provides nucleic acid detection methods, comprising:

(a) incubating a sample with dNTPs, ATP, a forward primer and a reverse primer that are each complementary to a target nucleic acid, a single stranded DNA fluorophore quencher (ssDNA-FQ) comprising a fluorophore and a quencher, a strand displacement DNA polymerase, single-stranded DNA binding protein, and a recombinase to form a mixture;

wherein incubating the sample results in base pairing of the forward primer and the reverse primer to the target nucleic acid if present in the sample and initiation of recombinase polymerase amplification (RPA) of the target nucleic acid in the mixture, exposing binding sites for Cas12a-crRNA complexes due to strand displacement;

(b) incubating the mixture with:

(i) a forward Cas12a-crRNA complex and a reverse Cas12a-crRNA complex to form an assembled mixture, wherein the forward Cas12a-crRNA complex comprises a forward crRNA and Cas12a protein or functional analogue thereof, the reverse Cas12a-crRNA complex comprises a reverse crRNA and the Cas12a protein or functional analogue thereof, wherein (I) the forward crRNA is between 10-100, 10-90, 10-80, 10-70, 10-60, 10-50, 10-40, 10-30, 20-100, 20-90, 20-80, 20-70, 20-60, 20-50, 2040, 20-30, or 20-24 nucleotides ("nt") in length, and is designed to bind to the target nucleic acid within 0-25, 0-20, 0-15, 0-10, or 0-5 nt of the forward primer on the opposite strand from the forward primer; and (II) the reverse crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the reverse primer on the opposite strand from the reverse primer, or (ii) one or more Cas12a-crRNA complexes comprising a crRNA and Cas12a protein or functional analogue thereof to form an assembled mixture, wherein each of the one or more crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid between forward and reverse primer binding sites;

wherein all of the crRNAs in option (i) or (ii) each have
a GC content of between about 50% and about 65%,
and a melting temperature ($T_m$) of between about
56-65° C. using nearest neighbor method under the
condition of 0.1 µM oligos and 1 M Na$^+$;

wherein none of the crRNAs include the protospacer
adjacent motif (PAM) sequence TTTV;

wherein if the target nucleic acid is present in the mixture,
incubating the mixture results in binding of either:

(I) the forward Cas12a-crRNA complex and the reverse
Cas12a-crRNA complex to the binding sites for
Cas12a-crRNA complexes on the target nucleic acid
and Cas12a endonuclease activation and cleavage of
ssDNA-FQ reporters to produce fluorescence; or (II) the one or more Cas12a-crRNA complex to the
binding sites for Cas12a-crRNA complexes on the
target nucleic acid, and Cas12a endonuclease acti-
vation and cleavage of ssDNA-FQ reporters to pro-
duce fluorescence; and (c) detecting fluorescence emitted from the assembled
mixture, wherein fluorescence emission detection indi-
cates presence of the target nucleic acid in the sample.

As described in detail in the attached examples, the
methods and compositions of the disclosure (referred to in
the examples as All-In-One Dual CRISPR-Cas12a (termed
"AIOD-CRISPR") permit simple, rapid, ultrasensitive, spe-
cific, one-pot and visual detection of nucleic acids (DNA and
RNA). In one embodiment, dual crRNAs are introduced to
initiate highly sensitive dual CRISPR-based nucleic acid
detection. In other embodiments, one or more crRNAs as
defined may be used. In the AIOD-CRISPR assay, all
components for nucleic acid amplification and CRISPR-
based detection are mixed in a single, one-pot reaction
system and incubated at a single temperature, eliminating
the need for separate pre-amplification and transfer of ampli-
fied product. Further details are provided in the examples.

Unlike previously reported CRISPR-based nucleic acid
detection, the presently claimed methods can be used in a
non-PAM strategy for crRNA design. This provides several
advantages, including but not limited to significantly
improving the design flexibility of both crRNAs and primers
without the need to have the specific a PAM sequence motif
(TTTV) in the nucleic acid amplification product, as most
targeted nucleic acid sequences may not contain the specific
PAM sequence (TTTV); and increasing the efficiency of
recombinase polymerase amplification and avoiding the
rapid cleavage of amplicons and templates by activated
Cas12a compared to PAM-based methods. Thus, in one
embodiment the crRNAs do not include a PAM sequence.

The forward and reverse primer pair can be of suitable
length and selective for any target nucleic acid of interest.
The target nucleic acid may be any suitable target nucleic
acid, including but not limited to DNA and RNA. In one
embodiment, the target nucleic acid is DNA, including but
not limited to genomic DNA. In another embodiment, the
target nucleic acid is RNA, including but not limited to
mRNA. In one embodiment, the target nucleic acid com-
prises RNA, and the method further comprises incubating
the sample with reverse transcriptase. Any suitable reverse
transcriptase may be used, including but not limited to Avian
Myeloblastosis Virus (AMV) reverse transcriptase.

The primer pair can be designed to amplify any length of
the target nucleic acid as deemed appropriate for an intended
use. In non-limiting embodiments, the forward primer and
the reverse primer are designed to generate a target nucleic
acid amplification product of between 100-500 base pairs in
length. The primers may be present in the assembled mixture at any concentration suitable for an intended purpose. In
various embodiments, the forward primer and the reverse
primer are each present in the assembled mixture at a
concentration between 50 nM-1.6 µM, 50 nM-1 µM, 50
nM-750 nM, 50 nM-500 nM, 50 nM-400 nM, 50 nM-350
nM, 100 nM-1.6 µM, 100 nM-1 µM, 100 nM-750 nM, 100
nM-500 nM, 100 nM-400 nM, 100 nM-350 nM, 150 nM-1.6
µM, 150 nM-1 µM, 150 nM-750 nM, 150 nM-500 nM, 150
nM-400 nM, 150 nM-350 nM, 200 nM-1.6 µM, 200 nM-1
µM, 200 nM-750 nM, 200 nM-500 nM, 200 nM-400 nM,
200 nM-350 nM, 250 nM-1.6 µM, 250 nM-1 µM, 250
nM-750 nM, 250 nM-500 nM, 250 nM-400 nM, 250
nM-350 nM, 300 nM-1.6 µM, 300 nM-1 µM, 300 nM-750
nM, 300 nM-500 nM, 300 nM-400 nM, 300 nM-350 nM, or
310 nM-330 nM.

As will be understood by those of skill in the art, the
dNTPs include dATP, dGTP, dCTP, and dTTP (or dUTP
when the target nucleic acid is an RNA). The dNTPs may be
present in the assembled mixture at any concentration suit-
able for an intended purpose. In certain embodiments, the
dNTPs are present in the assembled mixture at a concen-
tration between 0.2 mM-3 mM, 0.2 mM-2.5 mM, 0.2 mM-2
mM, 0.2 mM-1.5 mM, 0.5 mM-3.6 mM, 0.5 mM-3 mM, 0.5
mM-2.5 mM, 0.5 mM-2 mM, 0.5 mM-1.5 mM, 0.75
mM-3.6 mM, 0.75 mM-3 mM, 0.75 mM-2.5 mM, 0.75
mM-2 mM, 0.75 mM-1.5 mM, 1 mM-3.6 mM, 1 mM-3 mM,
1 mM-2.5 mM, 1 mM-2 mM, 1 mM-1.5 mM, or 1.1 mM to
1.3 mM.

The ATP (adenosine triphosphate) may be present in the
assembled mixture at any concentration suitable for an
intended purpose. In various embodiments, the ATP is
present in the assembled mixture at a concentration between
0.2 mM-8 mM, 0.2 mM-6 mM, 0.2 mM-4 mM, 0.2 mM-3.5
mM, 0.2 mM-3.1 mM, 0.5 mM-10 mM, 0.5 mM-8 mM, 0.5
mM-6 mM, 0.5 mM-4 mM, 0.5 mM-3.5 mM, 0.5 mM-3.1
mM, 1 mM-10 mM, 1 mM-8 mM, 1 mM-6 mM, 1 mM-4
mM, 1 mM-3.5 mM, 1 mM-3.1 mM, 1.5 mM-10 mM, 1.5
mM-8 mM, 1.5 mM-6 mM, 1.5 mM-4 mM, 1.5 mM-3.5
mM, 1.5 mM-3.1 mM, 2 mM-10 mM, 2 mM-8 mM, 2 mM-6
mM, 2 mM-4 mM, 2 mM-3.5 mM, 2 mM-3.1 mM, 2.5
mM-10 mM, 2.5 mM-8 mM, 2.5 mM-6 mM, 2.5 mM-4 mM,
2.5 mM-3.5 mM, 2.5 mM-3.1 mM, or 2.9 mM-3.1 mM.

The single stranded DNA fluorophore quencher (ssDNA-
FQ) comprises a fluorophore and a quencher; any suitable
fluorophore and quencher may be used as deemed appro-
priate for an intended end use. In one embodiment, the
ssDNA-FQ reporter is target irrelevant. As used herein,
"target irrelevant" means that the ssDNA-FQ can just be
present in solution. The ss DNA component of the ssDNA-
FQ may be of any suitable nucleotide composition and
length as deemed appropriate for an intended purpose. In
one embodiment, the ss DNA component of ssDNA-FQ is
between 5-30 nucleotides in length. In another embodiment,
the ssDNA-FQ comprises, but is not limited to fluorophore
6-FAM at 5'-end and quencher DABCYL at 3'-end. The
ssDNA-FQ may be present in the assembled mixture at any
concentration as deemed suitable for an intended use. In
certain embodiments, the ssDNA-FQ is present in the
assembled mixture at a concentration of between 0.2 µM-14
µM, 0.2 µM-12 µM, 0.2 µM-10 µM, 0.2 µM-9 µM, 0.2
µM-8.5 µM, 1 µM-16 µM, 1 µM-14 µM, 1 µM-12 µM, 1
µM-10 µM 1 µM-9 µM, 1 µM-8.5 µM, 2.5 µM-16 µM, 2.5
µM-14 µM, 2.5 µM-12 µM, 2.5 µM-10 µM, 2.5 µM-9 µM,
2.5 µM-8.5 µM, 5 µM-16 µM, 5 µM-14 µM, 5 µM-12 µM,
5 µM-10 µM, 5 µM-9 µM, 5 µM-8.5 µM, 7.5 µM-16 µM, 7.5
µM-14 µM, 7.5 µM-12 µM, 7.5 µM-10 µM, 7.5 µM-9 µM,
7.5 µM-8.5 µM, 7.8 µM-8.2 µM, or 7.9 µM-8.1 µM.

Any suitable strand displacement DNA polymerase may be used as deemed appropriate for an intended use. In one embodiment, the strand displacement DNA polymerase may comprise, but is not limited to Bsu DNA polymerase. The strand displacement DNA polymerase may be present in the assembled mixture at any concentration deemed suitable for an intended use. In certain embodiments, the strand displacement DNA polymerase is present in the assembled mixture at a concentration between 5 ng/μL-0.75 μg/μL, 5 ng/μL-0.50 μg/μL, 5 ng/μL-0.25 μg/μL, 5 ng/μL-0.1 μg/μL, 5 ng/μL-0.5 μg/μL, 5 ng/μL-0.4 μg/μL, 10 ng/μL-1 μg/μL, 10 ng/μL-0.75 μg/μL, 10 ng/μL-0.50 μg/μL, 10 ng/μL-0.25 μg/μL, 10 ng/μL-0.1 μg/μL, 10 ng/μL-0.5 μg/μL, 10 ng/μL-0.4 μg/μL, 20 ng/μL-1 μg/μL, 20 ng/μL-0.75 μg/μL, 20 ng/μL-0.50 μg/μL, 20 ng/μL-0.25 μg/μL, 20 ng/μL-0.1 μg/μL, 20 ng/μL-0.5 μg/μL, 20 ng/μL-0.4 μg/μL, 25 ng/μL-1 μg/μL, 25 ng/μL-0.75 μg/μL, 25 ng/μL-0.50 μg/μL, 25 ng/μLL-0.25 μg/μL, 25 ng/μL-0.1 μg/μL, 25 ng/μL-0.5 μg/μL, 25 ng/μL-0.4 μg/μL, 28 ng/μL-32 ng/μL, or 29 ng/μL-31 ng/μL.

Any suitable single stranded DNA binding protein may be used as deemed appropriate for an intended use. In certain embodiments, the single-stranded DNA binding protein may comprise but is not limited to T4 gp32, Rb69 gp32, or combinations thereof. The single-stranded DNA binding protein may be present in the assembled mixture at any concentration deemed suitable for an intended use. In certain embodiments, the single-stranded DNA binding protein is present in the assembled mixture at a concentration between 50 ng/μL-7.5 μg/μL, 50 ng/μL-5 μg/μL, 50 ng/μL-2.5 μg/μL, 50 ng/μL-1 μg/μL, 250 ng/μL-10 μg/μL, 250 ng/μL-7.5 μg/μL, 250 ng/μL-5 μg/μL, 250 ng/μL-2.5 μg/μL, 250 ng/μL-1 μg/μL, 500 ng/μL-10 μg/μL, 500 ng/μL-7.5 μg/μL, 500 ng/μL-5 μg/μL, 500 ng/μL-2.5 μg/μL, 500 ng/μL-1 μg/μL, 750 ng/μL-10 μg/μL, 750 ng/μL-7.5 μg/μL, 750 ng/μL-5 μg/μL, 750 ng/μL-2.5 μg/μL, 750 ng/μL-1 μg/μL, or 850 ng/μL-950 ng/μL.

Any suitable recombinase may be used as deemed appropriate for an intended use. In certain embodiments, the recombinase may comprise, but is not limited to T2 UvsX, T4 UvsX, T6 UvsX, Aeh1 UvsX, Rb69 UvsX, or combinations thereof. The recombinase may be present in the assembled mixture at any concentration deemed suitable for an intended use.

In certain embodiments, the recombinase is present in the assembled mixture at a concentration between 20 ng/μL-1 μg/μL, 20 ng/μL-0.75 μg/μL, 20 ng/μL-0.5 μg/μL, 20 ng/μL-0.25 μg/μL, 20 ng/μL-0.15 μg/μL, 50 ng/μL-5 μg/μL, 50 ng/μL-1 μg/μL, 50 ng/μL-0.75 μg/μL, 50 ng/μL-0.5 μg/μL, 50 ng/μL-0.25 μg/μL, 50 ng/μL-0.15 μg/μL, 75 ng/μL-5 μg/μL, 75 ng/μL-1 μg/μL, 75 ng/μL-0.75 μg/μL, 75 ng/μL-0.5 μg/μL, 75 ng/μL-0.25 μg/μL, 75 ng/μL-0.15 μg/μL, 100 ng/μL-5 μg/μL, 100 ng/μL-1 μg/μL, 100 ng/μL-0.75 μg/μL, 100 ng/μL-0.5 μg/μL, 100 ng/μL-0.25 μg/μL, 100 ng/μL-0.15 μg/μL, or 110 ng/μL-130 ng/μL.

In one embodiment, combining the mixture with Cas12a-crRNA complexes to generate the assembled mixture comprises combining the mixture with pre-formed Cas12a-crRNA complexes. In another embodiment, combining the mixture with Cas12a-crRNA complexes to generate the assembled mixture comprises combining the mixture with the crRNAs and the Cas12a protein or functional analogue thereof, wherein the Cas12a-crRNA complexes form in the assembled mixture.

The forward crRNA and the reverse crRNA may each be present in any concentration suitable for an intended use. In certain embodiments, the forward crRNA and the reverse crRNA are each present in the assembled mixture at a concentration of between 0.05 μM-5 μM, 0.05 μM-2.5 μM, 0.05 μM-1 μM, 0.05 μM-0.75 μM, 0.25 μM-5 μM, 0.25 μM-5 μM, 0.25 μM-2.5 μM, 0.25 μM-1 μM, 0.25 μM-0.75 μM, 0.5 μM-5 μM, 0.5 μM-5 μM, 0.5 μM-2.5 μM, 0.5 μM-1 μM, or 0.5 μM-0.75 μM.

The Cas12a may be present in the assembled mixture at any concentration as deemed suitable for an intended use. In certain embodiments, the Cas12a is present in the assembled mixture at a concentration of between 0.01 μM-7.5 μM, 0.01 μM-5 μM, 0.01 μM-2.5 IM, 0.01 μM-2 μM, 0.1 μM-10 μM, 0.1 μM-7.5 μM, 0.1 μM-5 μM, 0.1 μM-2.5 μM, 0.1 μM-2 μM, 0.5 μM-10 μM, 0.5 μM-7.5 μM, 0.5 μM-5 μM, 0.5 μM-2.5 μM, 0.5 μM-2 μM, 0.75 μM-10 μM, 0.75 μM-7.5 μM, 0.75 μM-5 μM, 0.75 μM-2.5 μM, 0.75 μM-2 μM, 1 μM-0 μM, 1 μM-7.5 μM, 1 μM-5 μM, 1 μM-2.5 μM, 1 μM-2 μM, or 1 μM-1.5 μM.

In one embodiment, the incubating further comprises incubating the sample with a $Mg^{2+}$ ion source. Any suitable $Mg^{2+}$ ion source may be used, including but not limited to magnesium acetate, magnesium chloride, magnesium sulphate, magnesium borate, or combinations thereof. The $Mg^{2+}$ ion source may be present in any suitable concentration. In various embodiments, the $Mg^{2+}$ ion source is present in the assembled mixture at a concentration between 2 mM-175 mM, 2 mM-150 mM, 2 mM-125 mM, 2 mM-100 mM, 2 mM-75 mM, 2 mM-50 mM, 2 mM-25 mM, 2 mM-20 mM, 2 mM-15 mM, 5 mM-200 mM, 5 mM-175 mM, 5 mM-150 mM, 5 mM-125 mM, 5 mM-100 mM, 5 mM-75 mM, 5 mM-50 mM, 5 mM-25 mM, 5 mM-20 mM, 5 mM-15 mM, 10 mM-200 mM, I0 mM-175 mM, 10 mM-150 mM, 10 mM-125 mM, 10 mM-100 mM, 10 mM-75 mM, 10 mM-50 mM, 10 mM-25 mM, 10 mM-20 mM, 10 mM-15 mM, 11 mM-15 mM, 12 mM-15 mM, or 13 mM-15 mM.

In another embodiment, the incubating further comprises incubating the sample with a crowding agent and a recombinase loading agent. The crowding agent may be any suitable polymer of other molecule that increases the strength of interactions of enzymes and nucleic acids to improve the nucleic acid replication process. Exemplary such crowding agents include but are not limited to polyethylene glycol (PEG), dextran, ficoll, and poly(N-vinylpyrrolidone) (PVP). In specific embodiments, the crowding agent may comprise, but is not limited to, polyethylene glycol (PEG) over 10,000 Daltons in molecular weight, particularly PEG of 20,000 Daltons or more in molecular weight. The crowding agent may be present in the assembled mixture at any suitable percentage on a weight/volume (wt/vol) basis. In various embodiments, the crowding agent is present in the assembled mixture between 0.5%-12%, 0.5%-10%, 0.5%-7.5%, 0.5%-6%, 1%-15%, 1%-12%, 1%-10%, 1%-7.5%, 1%-6%, 2.5%-15%, 2.5%-12%, 2.5%-10%, 2.5%-7.5%, 2.5%-6%, 4%-15%, 4%-12%, 4%-10%, 4%-7.5%, or 4%-6% crowding agent on a wt/vol basis.

As used herein, a recombinase loading agent is a factor to increase the affinity of recombinase protein for single-stranded DNA. Any suitable recombinase loading agent may be used as deemed appropriate for an intended use. In various non-limiting embodiments, the recombinase loading agent may comprise, but is not limited to T2 UvsY, T4 UvsY, T6 UvsY, Aeh1 UvsY, Rb69 UvsY, or combinations thereof. The recombinase loading agent may be present at any suitable concentration in the assembled mixture. In various specific embodiments, the recombinase loading agent is present in the assembled mixture at a concentration between about 5 ng/μL-0.5 μg/μL, 5 ng/μL-0.25 μg/μL, 5 ng/μL-0.1 μg/μL, 5 ng/μL-0.075 μg/μL, 5 ng/μL-0.05 μg/μL, 10 ng/µL-1 µg/µL, 10 ng/µL-0.5 µg/µL, 10 ng/µL-0.25 µg/µL, 10 ng/µL-0.1 µg/µL, 10 ng/µL-0.075 µg/µL, 10 ng/µL-0.05 µg/µL, 20 ng/µL-1 µg/µL, 20 ng/µL-0.5 µg/µL, 20 ng/µL-0.25 µg/µL, 20 ng/µLL-0.1 µg/µL, 20 ng/µL-0.075 µg/µL, 20 ng/µL-0.05 µg/µL, or 25 ng/µL-35 ng/µL.

In one specific embodiment, the assembled mixture may comprise:

(i) 2 mM-200 mM of the Mg$^{2+}$ ion source;
(ii) 0.5%-15% of the crowding agent on a wt/vol basis;
(iii) 0.2 mM-3.6 mM of the dNTPs;
(iv) 0.2 mM-10 mM of the ATP;
(v) 50 nM-1.6 µM each of the forward primer and the reverse primer;
(vi) 0.2 µM-16 µM of the ssDNA-FQ;
(vii) 5 ng/µL-1 µg/µL of the strand displacement DNA polymerase;
(viii) 50 ng/µL-10 µg/µL of the single-stranded DNA binding protein;
(ix) 20 ng/µL-5 µg/µL of the recombinase; and
(x) 5 ng/µL-1 µg/µL of the recombinase loading agent;
(xi) 0.05 µM-5 µM each of the forward crRNA and the reverse crRNA, or each crRNA in the one or more Cas12a-crRNA complexes; and
(xii) 0.01 µM-10 µM of the Cas12a protein or functional analogue thereof.

In this embodiment, the incubating step comprises (I) pre-mixing components (i)-(v) to form a first pre-mixture, and (II) pre-mixing components (vi)-(x) to form a second pre-mixture, and then mixing the first pre-mixture and the second pre-mixture to form the assembled mixture.

In various further embodiments, the assembled mixture may further comprise:

(xiii) a concentration between 0.5 mM-500 mM, 0.5 mM-250 mM, 0.5 mM-150 mM, 25 mM-500 mM, 25 mM-250 mM, 25 mM-150 mM, 50 mM-500 mM, 50 mM-250 mM, 50 mM-150 mM, 75 mM-500 mM, 75 mM-250 mM, 75 mM-150 mM, or 90 mM-110 mM of a K$^{2+}$ ion source including but not limited to potassium acetate, potassium chloride, potassium sulphate, potassium borate, or combinations thereof;
(xiv) a concentration between 0.1 mM-20 mM, 0.1 mM-15 mM, 0.1 mM-10 mM, 0.1 mM-5 mM, 0.1 mM-3 mM, 0.5 mM-20 mM, 0.5 mM-15 mM, 0.5 mM-10 mM, 0.5 mM-5 mM, 0.5 mM-3 mM, 1 mM-20 mM, 1 mM-15 mM, 1 mM-10 mM, 1 mM-5 mM, or 1 mM-3 mM of dithiothreitol (DTT);
(xv) a concentration between 0.01 µg/µL-1.0 µg/µL, 0.05 µg/µL-0.5 µg/µL, 0.0.75 µg/µL-0.25 µg/µL, or 0.9 µg/µL-1.1 µg/µL of creatine kinase; and
(xvi) a concentration between 0.5 mM-500 mM, 0.5 mM-250 mM, 0.5 mM-100 mM, 0.5 mM-75 mM, 5 mM-500 mM, 5 mM-250 mM, 5 mM-100 mM, 5 mM-75 mM, 20 mM-500 mM, 20 mM-250 mM, 20 mM-100 mM, 20 mM-75 mM, 40 mM-500 mM, 40 mM-250 mM, 40 mM-100 mM, 40 mM-75 mM, or 40 mM-60 mM phosphocreatine.

In this embodiment, the first pre-mixture comprises components (i)-(vi), and (xiii)-(xvi).

In another specific embodiment, the assembled mixture comprises about 100 mM potassium acetate, about 14 mM magnesium acetate, about 2 mM DTT, about 5% polyethylene glycol over 10,000 Daltons in molecular weight, about 1.2 mM dNTPs, about 3 mM ATP, about 50 mM phosphocreatine, about 0.1 µg/µL creatine kinase, about 320 nM each of the forward primer and the reverse primer, about 8 µM the ssDNA-FQ reporter, about 0.03 µg/µL strand displacement DNA polymerase, about 0.9 µg/µL single-stranded DNA binding protein, about 0.12 µg/µL recombinase, about 0.03 µg/µL recombinase loading agent, about 0.64 µM each of the forward crRNA and the reverse crRNA, and about 1.28 µM of Cas12a protein or functional analogue thereof.

Any suitable other conditions may be used in carrying out the methods of the disclosure as suitable for an intended purpose. In one embodiment, any suitable pH may be used, including but not limited to the assembled mixture having a pH between 7.0 and 8.5. In another embodiment, the incubating in step (a) of the method may be carried out for any time suitable for an intended purpose, including but not limited to being carried out for between 1 minute and 60 minutes, 1 minute and 45 minutes, 1 minute and 30 minutes, 1 minute and 15 minutes, 5 minutes and 60 minutes, 5 minutes and 45 minutes, 5 minutes and 30 minutes, 5 minutes and 15 minutes, 7.5 minutes and 12.5 minutes, or 9 minutes and 11 minutes, or being carried out for about 10 minutes. In further embodiments, the incubating in step (b) of the method may be carried out for any time suitable for an intended purpose, including but not limited to being carried out for between 1 minute and 120 minutes, 1 minute and 90 minutes, 1 minute and 60 minutes, 10 minutes and 120 minutes, 10 minutes and 90 minutes, 10 minutes and 60 minutes, 20 minutes and 120 minutes, 20 minutes and 90 minutes, 20 minutes and 60 minutes, 30 minutes and 50 minutes, or 35 minutes and 45 minutes, or being carried out for about 40 minutes.

The incubations may be carried out at any temperature deemed suitable for an intended purpose. In various embodiments, incubating the sample and incubating the mixture may be carried out at between 32° C. and 43° C., or between 35° C. and 42° C. The temperatures for incubating the sample and incubating the mixture may be carried out at the same or different temperatures. In one embodiment, incubating the sample and incubating the mixture are each carried out at the same temperature.

The methods may comprise the use of any suitable biological sample from any suitable subject. In one non-limiting embodiment, the subject may any suitable mammal including but not limited to mouse, rat, rabbit, dog, sheep, goat, equine, bovine, primate, etc. In one embodiment, the subject is a human subject. In other embodiments, the biological sample may comprise, by way of non-limiting examples, blood, plasma, saliva, a cheek or other swab, sputum or urine.

The target nucleic acid may be any suitable target nucleic acid as noted above. In one embodiment, the target nucleic acid is a pathogen nucleic acid, nucleic acid biomarker (e.g., cell-free DNA, mRNA), or tumor specific nucleic acid. In further embodiments, the target nucleic acid is a pathogen nucleic acid, wherein the pathogen is a bacterial, viral, fungal pathogen or any other organism capable of causing disease or illness in its host. In other embodiments, the pathogen is a viral pathogen, including but not limited to human immunodeficiency virus (HIV), severe acute respiratory syndrome coronavirus (SARS-CoV), Middle East respiratory syndrome (MERS) virus, and severe acute respiratory syndrome coronavirus-2 (SARS-CoV-2).

In some embodiments, the methods may comprise determining an amount of target nucleic acid. In one such embodiment, the method comprises quantitating an amount of the target nucleic acid based on detecting fluorescence emitted from the assembled mixture.

Any suitable means for detecting fluorescence emission may be used as suitable for an intended purpose. In various embodiments, detecting fluorescence emission comprises one or more of detecting fluorescence emission by the naked eye, smartphone, or other fluorescence detection equipment. In other embodiments, detecting fluorescence emission comprises exciting fluorescence signal by UV or blue light sources. Exemplary such detection techniques are described in the examples that follow.

In a second aspect, the disclosure provides compositions that may be used, for example, in the nucleic acid detection methods of the first aspect of the disclosure. All terms used in this second aspect have the same meaning as described in the first aspect, and all embodiments described for the various components in the first aspect are also applicable to all embodiments and combinations of embodiments of the second aspect. In one embodiment, the composition comprises:

(a) one or more containers comprising dNTPs, ATP, and optionally comprising a forward primer and a reverse primer that are each complementary to a target nucleic acid, a single stranded DNA fluorophore quencher (ssDNA-FQ) comprising a fluorophore and a quencher, a strand displacement DNA polymerase, single-stranded DNA binding protein, and a recombinase; and (b) a further container comprising (i) a forward Cas12a-crRNA complex comprising a forward crRNA and Cas12a protein or functional analogue thereof wherein the forward crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the forward primer on the opposite strand from the forward primer, and a reverse Cas12a-crRNA complex comprising a reverse crRNA and Cas12a protein or functional analogue thereof, wherein the reverse crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the reverse primer on the opposite strand from the reverse primer;

(ii) a forward crRNA wherein the forward crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the forward primer on the opposite strand from the forward primer, a reverse crRNA wherein the reverse crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the reverse primer on the opposite strand from the reverse primer, and Cas12a protein or functional analogue thereof;

(iii) one or more Cas12a-crRNA complexes comprising a crRNA and Cas12a protein or functional analogue thereof, wherein each of the one or more crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid between forward and reverse primer binding sites; or (iv) one or more crRNA and Cas12a protein or functional analogue thereof, wherein each of the one or more crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid between forward and reverse primer binding sites;

wherein each crRNA has a GC content of between about 50% and about 65%, and a melting temperature ($T_m$) of between about 56-65° C. using nearest neighbor method under the condition of 0.1 µM oligos and 1 M Na$^+$ and wherein none of the crRNAs include the protospacer adjacent motif (PAM) sequence TTTV.

In another embodiment, the composition comprises (a) a first container comprising dNTPs, ATP, and optionally comprising a forward primer and a reverse primer that are each complementary to a target nucleic acid, (b) a second container comprising a single stranded DNA fluorophore quencher (ssDNA-FQ) comprising a fluorophore and a quencher, a strand displacement DNA polymerase, single-stranded DNA binding protein, and a recombinase; and (c) a third container comprising (i) a forward Cas12a-crRNA complex comprising a forward crRNA and Cas12a protein or functional analogue thereof wherein the forward crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the forward primer on the opposite strand from the forward primer, and a reverse Cas12a-crRNA complex comprising a reverse crRNA and Cas12a protein or functional analogue thereof, wherein the reverse crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the reverse primer on the opposite strand from the reverse primer;

(ii) a forward crRNA wherein the forward crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the forward primer on the opposite strand from the forward primer, a reverse crRNA wherein the reverse crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the reverse primer on the opposite strand from the reverse primer, and Cas12a protein or functional analogue thereof;

(iii) one or more Cas12a-crRNA complexes comprising a crRNA and Cas12a protein or functional analogue thereof, wherein each of the one or more crRNA is between 10-100, 10-90, 10-80, 10-70, 10-60, 10-50, 1040, 10-30, 20-100, 20-90, 20-80, 20-70, 20-60, 20-50, 20-40, 20-30, or 20-24 nt in length, and is designed to bind to the target nucleic acid between forward and reverse primer binding sites; or (iv) one or more crRNA and Cas12a protein or functional analogue thereof, wherein each of the one or more crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid between forward and reverse primer binding sites;

wherein each crRNA has a GC content of between about 50% and about 65%, and a melting temperature ($T_m$) of between about 56-65° C. using nearest neighbor method under the condition of 0.1 μM oligos and 1 M $Na^+$; and wherein none of the crRNAs include the protospacer adjacent motif (PAM) sequence TTTV.

In each of these embodiments, the compositions (or kits) include separate containers providing the various components to carry out the methods of the first aspect of the disclosure. The contents of the containers may then be suitably mixed as deemed appropriate by an end user to carry out the methods of the disclosure. Any suitable containers may be used in the compositions of the disclosure.

In one embodiment, the one or more containers or the first container further comprises a $Mg^{2+}$ source, wherein the $Mg^{2+}$ ion source may comprise, but is not limited to, magnesium acetate, magnesium chloride, magnesium sulphate, magnesium borate, or combinations thereof. In one such embodiment, the one or more containers or the first container comprise a molar ratio of $Mg^{2+}$ source to dNTPs to of between 0.5:1 and 1000:1, 1.17 and 117, or about 11.7.

In another embodiment, the one or more containers or the first container further comprises a crowding agent, wherein the crowding agent may comprise, but is not limited to, polyethylene glycol (PEG) over 10,000 Daltons in molecular weight, particularly PEG of 20,000 Daltons or more in molecular weight. In one embodiment, the one or more containers or the first container comprise a weight/volume ratio between 1-50%, or about 5% by weight of the crowding agent.

In a further embodiment, the one or more containers or the second container further comprises recombinase loading agent. In one embodiment, the forward primer and the reverse primer are present in the one or more containers or the first container, and wherein the forward primer and the reverse primer are designed to generate a target nucleic acid amplification product of between 100-500 base pairs in length. In one embodiment, the forward primer and the reverse primer are present, and the one or more containers or the first container comprise a molar ratio of dNTPs to each of the forward primer and the reverse primer of between 125:1 and 72000:1, 3750:0.1 and 3750:10, or about 3750:1.

In one embodiment, the one or more containers or the first container comprise a molar ratio of dNTPs and ATP of between 0.02:1 and 18:1, 1:0.3 and 1:30, or about 1:3.

In another embodiment, the one or more containers or the first container further comprises a $K^{2+}$ source. In various embodiments, the $K^{2+}$ ion source includes but not limited to potassium acetate, potassium chloride, potassium sulphate, potassium borate, or combinations thereof, dithiothreitol (DTT), creatine kinase, and phosphocreatine. In various further embodiments (a) the one or more containers or the first container comprise a molar ratio of $K^{2+}$ source to $Mg^{2+}$ source of between 0.0025:1 and 250:1, 0.7 and 70, or about 7; (b) the one or more containers or the first container comprise a molar ratio of $K^{2+}$ source to DTT of between 0.0002:1 and 5000:1, 50:0.1 and 50:10, or about 50:1; and/or (c) the one or more containers or the first container comprise a molar ratio of $K^{2+}$ source to phosphocreatine of between 0.001 and 1000:1, 2:0.1 and 2:10, or about 2:1.

In a further embodiment, the one or more containers or the second container comprise a molar ratio of the recombinase and the recombinase loading agent of between 0.12 μg/μL to 0.003 μg/μL and 0.12 μg/μL to 0.3 μg/μL, or about 0.12 μg/μL to 0.03 μg/μL.

In all embodiments, the components in the compositions may be present in any form suitable for an intended purpose. In one embodiment, some or all of the components may be present in solution. In other embodiments, some or all components may be present as a powder or frozen, for later reconstitution; in this embodiment, the molarity or concentration provided refers to the molarity or concentration upon reconstitution.

In one embodiment, the compositions of the second aspect comprise:

(a) a first container comprising the following components when provided as a solution, or when reconstituted in an appropriate solution for use;

(i) 2 mM-200 mM of a $Mg^{2+}$ ion source;

(ii) 0.5%-15% crowding agent on a wt/vol basis;

(iii) 0.2 mM-3.6 mM dNTPs (including dATP, dGTP, dCTP, and dTTP (or dUTP);

(iv) 0.2 mM-10 mM ATP;

(v) 50 nM-1.6 μM each of a forward primer and a reverse primer that are complementary to a target nucleic acid and are designed to generate an amplification product of between 100-150 base (not over 500 bp) pairs in length; and (b) a second container comprising (vi) 0.2 μM-16 μM of single stranded DNA fluorophore quencher (ssDNA-FQ) comprising fluorophore 6-FAM at 5'-end and quencher DABCYL at 3'-end;

(vii) 5 ng/μL-1 μg/μL strand displacement DNA;

(viii) 50 ng/μL-10 μg/μL single-stranded DNA binding protein;

(ix) 20 ng/μL-5 μg/μL recombinase; and (x) 5 ng/μL-1 μg/μL recombinase loading agent;

In this embodiment, the composition may further comprise a third container, wherein the third container comprises the following components when provided as a solution, or when reconstituted in an appropriate solution for use;

(i) a forward Cas12a-crRNA complex comprising a forward crRNA and Cas12a protein or functional analogue thereof wherein the forward crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the forward primer on the opposite strand from the forward primer, and a reverse Cas12a-crRNA complex comprising a reverse crRNA and Cas12a protein or functional analogue thereof, wherein the reverse crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the reverse primer on the opposite strand from the reverse primer;

(ii) a forward crRNA wherein the forward crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the forward primer on the opposite strand from the forward primer, a reverse crRNA wherein the reverse crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the reverse primer on the opposite strand from the reverse primer, and Cas12a protein or functional analogue thereof;

(iii) one or more Cas12a-crRNA complexes comprising a crRNA and Cas12a protein or functional analogue thereof, wherein each of the one or more crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid between forward and reverse primer binding sites; or (iv) one or more crRNA and Cas12a protein or functional analogue thereof, wherein each of the one or more crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid between forward and reverse primer binding sites;

wherein each crRNA has a GC content of between about 50% and about 65%, and a melting temperature ($T_m$) of between about 56-65° C. using nearest neighbor method under the condition of 0.1 μM oligos and 1 M Na$^+$; and wherein none of the crRNAs include the protospacer adjacent motif (PAM) sequence TTTV.

In various further embodiments of these compositions of the second aspect:

The Mg$^{2+}$ ion source may comprise, but is not limited to, from magnesium acetate, magnesium chloride, magnesium sulphate, magnesium borate, or combinations thereof. In various embodiments, the Mg$^{2+}$ ion source is present in the first container at a concentration between 2 mM-175 mM, 2 mM-150 mM, 2 mM-125 mM, 2 mM-100 mM, 2 mM-75 mM, 2 mM-50 mM, 2 mM-25 mM, 2 mM-20 mM, 2 mM-15 mM, 5 mM-200 mM, 5 mM-175 mM, 5 mM-150 mM, 5 mM-125 mM, 5 mM-100 mM, 5 mM-75 mM, 5 mM-50 mM, 5 mM-25 mM, 5 mM-20 mM, 5 mM-15 mM, 10 mM-200 mM, 10 mM-175 mM, 10 mM-150 mM, 10 mM-125 mM, 10 mM-100 mM, 10 mM-75 mM, 10 mM-50 mM, 10 mM-25 mM, 10 mM-20 mM, 10 mM-15 mM, 11 mM-15 mM, 12 mM-15 mM or 13 mM-15 mM.

The crowding agent may comprise, but is not limited to, polyethylene glycol (PEG) over 10,000 Daltons in molecular weight, particularly PEG of 20,000 Daltons or more in molecular weight, and the crowding agent may be present in the first container between 0.5%-6-12%, 0.5%-10%, 0.5%-7.5%, 0.5%-6%, 1%-15%, 1%-12%, 1%-10%, 1%-7.5%, 1%-6%, 2.50%-15%, 2.5%-12%, 2.5%-10%, 2.5%-7.5%, 2.5%-6%, 4%-15%, 4%-12%, 4%-10%, 4%-7.5%, or 4%-6% crowding agent on a wt/vol basis.

The dNTPs may be present in the first container at a concentration between 0.2 mM-3 mM, 0.2 mM-2.5 mM, 0.2 mM-2 mM, 0.2 mM-1.5 mM, 0.5 mM-3.6 mM, 0.5 mM-3 mM, 0.5 mM-2.5 mM, 0.5 mM-2 mM, 0.5 mM-1.5 mM, 0.75 mM-3.6 mM, 0.75 mM-3 mM, 0.75 mM-2.5 mM, 0.75 mM-2 mM, 0.75 mM-1.5 mM, 1 mM-3.6 mM, 1 mM-3 mM, 1 mM-2.5 mM, 1 mM-2 mM, 1 mM-1.5 mM, or 1.1 mM to 1.3 mM.

The ATP may be present in the first container at a concentration between 0.2 mM-8 mM, 0.2 mM-6 mM, 0.2 mM-4 mM, 0.2 mM-3.5 mM, 0.2 mM-3.1 mM, 0.5 mM-10 mM, 0.5 mM-8 mM, 0.5 mM-6 mM, 0.5 mM-4 mM, 0.5 mM-3.5 mM, 0.5 mM-3.1 mM, 1 mM-10 mM, 1 mM-8 mM, 1 mM-6 mM, 1 mM-4 mM, 1 mM-3.5 mM, 1 mM-3.1 mM, 1.5 mM-10 mM, 1.5 mM-8 mM, 1.5 mM-6 mM, 1.5 mM-4 mM, 1.5 mM-3.5 mM, 1.5 mM-3.1 mM, 2 mM-10 mM, 2 mM-8 mM, 2 mM-6 mM, 2 mM-4 mM, 2 mM-3.5 mM, 2 mM-3.1 mM, 2.5 mM-10 mM, 2.5 mM-8 mM, 2.5 mM-6 mM, 2.5 mM-4 mM, 2.5 mM-3.5 mM, 2.5 mM-3.1 mM, or 2.9 mM-3.1 mM.

The forward primer and the reverse primer may each be present in the first container at a concentration between 50 nM-1.6 μM, 50 nM-1 μM, 50 nM-750 nM, 50 nM-500 nM, 50 nM-400 nM, 50 nM-350 nM, 100 nM-1.6 μM, 100 nM-1 μM, 100 nM-750 nM, 100 nM-500 nM, 100 nM-400 nM, 100 nM-350 nM, 150 nM-1.6 μM, 150 nM-1 μM, 150 nM-750 nM, 150 nM-500 nM, 150 nM-400 nM, 150 nM-350 nM, 200 nM-1.6 μM, 200 nM-1 μM, 200 nM-750 nM, 200 nM-500 nM, 200 nM-400 nM, 200 nM-350 nM, 250 nM-1.6 μM, 250 nM-1 μM, 250 nM-750 nM, 250 nM-500 nM, 250 nM-400 nM, 250 nM-350 nM, 300 nM-1.6 μM, 300 nM-1 μM, 300 nM-750 nM, 300 nM-500 nM, 300 nM-400 nM, 300 nM-350 nM, or 310 nM-330 nM.

The ssDNA-FQ reporter may be target irrelevant.

The ssDNA portion of the ssDNA-FQ may be between 5-30 nucleotides in length.

The ssDNA-FQ may be present in the second container at a concentration of between 0.2 μM-14 μM, 0.2 μM-12 μM, 0.2 μM-10 μM, 0.2 μM-9 μM, 0.2 μM-8.5 μM, 1 μM-16 μM, 1 μM-14 μM, 1 μM-12 μM, 1 μM-10 μM, 1 μM-9 μM, 1 μM-8.5 μM, 2.5 μM-16 μM, 2.5 μM-14 μM, 2.5 μM-12 μM, 2.5 μM-10 μM, 2.5 μM-9 μM, 2.5 μM-8.5 μM, 5 μM-16 μM 5 μM-14 μM, 5 μM-12 IM, 5 μM-10 μM 5 μM-9 μM, 5 μM-8.5 μM, 7.5 μM-16 μM, 7.5 μM-14 μM, 7.5 μM-12 μM, 7.5 μM-10 μM, 7.5 μM-9 μM, 7.5 μM-8.5 μM, 7.8 μM-8.2 μM, or 7.9 μM-8.1 μM.

The strand displacement DNA polymerase may comprise, but is not limited to Bsu DNA polymerase.

The strand displacement DNA polymerase may be present in the second container at a concentration between 5 ng/μL-0.75 μg/μL, 5 ng/μL-0.50 μg/μL, 5 ng/μL-0.25 μg/μL, 5 ng/μL-0.1 μg/μL, 5 ng/μL-0.5 μg/μL, 5 ng/μL-0.4 μg/μL, 10 ng/μL-1 μg/μL, 10 ng/μL-0.75 μg/μL, 10 ng/μL-0.50 μg/μL, 10 ng/μL-0.25 μg/μL, 10 ng/μL-0.1 μg/μL, 10 ng/μL-0.5 μg/μL, 10 ng/μL-0.4 μg/μL, 20 ng/μL-1 μg/μL, 20 ng/μL-0.75 μg/μL, 20 ng/μL-0.50 μg/μL, 20 ng/μL-0.25 μg/μL, 20 ng/μL-0.1 μg/μL, 20 ng/μL-0.5 μg/μL, 20 ng/μL-0.4 μg/μL, 25 ng/μL-1 μg/μL, 25 ng/μL-0.75 μg/μL, 25 ng/μL-0.50 μg/μL, 25 ng/μL-0.25 μg/μL, 25 ng/μL-0.1 μg/μL, 25 ng/μL-0.5 μg/μL, 25 ng/μL-0.4 μg/μL, 28 ng/μL-32 ng/μL, or 29 ng/μL-31 ng/μL.

The single-stranded DNA binding protein may comprise but is not limited to T4 gp32, Rb69 gp32, or combinations thereof.

The single-stranded DNA binding protein may be present in the second container at a concentration between 50 ng/μL-7.5 μg/μL, 50 ng/μL-5 μg/μL, 50 ng/μL-2.5 μg/μL, 50 ng/μL-1 μg/μL, 250 ng/μL-10 μg/μL, 250 ng/μL-7.5 μg/μL, 250 ng/μL-5 μg/μL, 250 ng/μL-2.5 μg/μL, 250 ng/μL-1 μg/μL, 500 ng/μL-10 μg/μL, 500 ng/μL-7.5 μg/μL, 500 ng/μL-5 μg/μL, 500 ng/μL-2.5 μg/μL, 500 ng/μLL-1 μg/μL, 750 ng/μL-10 μg/μL, 750 ng/μL-7.5 μg/μL, 750 ng/μL-5 μg/μL, 750 ng/μL-2.5 μg/μL, 750 ng/μL-1 μg/μL, or 850 ng/μL-950 ng/μL.

The recombinase may comprise, but is not limited to T2 UvsX, T4 UvsX, T6 UvsX, Aeh1 UvsX, Rb69 UvsX, or combinations thereof.

The recombinase may be present in the second container at a concentration between 20 ng/μL-1 μg/μL, 20 ng/μL-0.75 μg/μL, 20 ng/μL-0.5 μg/μL, 20 ng/μL-0.25 μg/μL, 20 ng/μL-0.15 μg/μL, 50 ng/μL-5 μg/μL, 50 ng/μL-1 μg/μL, 50 ng/μL-0.75 μg/μL, 50 ng/μL-0.5 μg/μL, 50 ng/μL-0.25 μg/μL, 50 ng/μL-0.15 μg/μL, 75 ng/μL-5 μg/μL, 75 ng/μL-1 μg/μL, 75 ng/μL-0.75 μg/μL, 75 ng/μL-0.5 μg/μL, 75 ng/μL-0.25 μg/μL, 75 ng/μL-0.15 μg/μL, 100 ng/μL-5 μg/μL, 100 ng/μL-1 μg/μL, 100 ng/μL-0.75 μg/μL, 100 ng/μL-0.5 μg/μL, 100 ng/μL-0.25 μg/μL, 100 ng/μL-0.15 μg/μL, or 110 ng/μL-130 ng/μLL.

The recombinase loading agent may comprise, but is not limited to T2 UvsY, T4 UvsY, T6 UvsY, Aeh1 UvsY, Rb69 UvsY, or combinations thereof.

The recombinase loading agent may be present in the second container at a concentration between about 5 ng/μL-0.5 μg/μL, 5 ng/μL-0.25 μg/μL, 5 ng/μL-0.1 μg/μL, 5 ng/μL-0.075 μg/μL, 5 ng/μL-0.05 μg/μL, 10 ng/μL-1 μg/μL, 10 ng/μL-0.5 μg/μL, 10 ng/μL-0.25 μg/μL, 10 ng/μL-0.1 μg/μL, 10 ng/μL-0.075 μg/μL, 10 ng/μL-0.05 μg/μL, 20 ng/μL-1 μg/μL, 20 ng/μL-0.5 μg/μL, 20 ng/μL-0.25 μg/μL, 20 ng/μL-0.1 μg/μL, 20 ng/μL-0.075 μg/μL, 20 ng/μL-0.05 μg/μL, or 25 ng/μL-35 ng/μL.

In another embodiment, the first container may further comprise:

(xi) a concentration of between 0.5 mM-500 mM, 0.5 mM-250 mM, 0.5 mM-150 mM, 25 mM-500 mM, 25 mM-250 mM, 25 mM-150 mM, 50 mM-500 mM, 50 mM-250 mM, 50 mM-150 mM, 75 mM-500 mM, 75 mM-250 mM, 75 mM-150 mM, or 90 mM-110 mM of a $K^{2+}$ ion source including but not limited to potassium acetate, potassium chloride, potassium sulphate, potassium borate, or combinations thereof;

(xii) a concentration of between 0.1 mM-20 mM, 0.1 mM-15 mM, 0.1 mM-10 mM, 0.1 mM-5 mM, 0.1 mM-3 mM, 0.5 mM-20 mM, 0.5 mM-15 mM, 0.5 mM-10 mM, 0.5 mM-5 mM, 0.5 mM-3 mM, 1 mM-20 mM, 1 mM-15 mM, 1 mM-10 mM, 1 mM-5 mM, or 1 mM-3 mM dithiothreitol (DTI);

(xiii) a concentration of between 0.1 μg/μL-1.0 μg/μL creatine kinase and (xiv) 0.5 mM-500 mM, 0.5 mM-250 mM, 0.5 mM-100 mM, 0.5 mM-75 mM, 5 mM-500 mM, 5 mM-250 mM, 5 mM-100 mM, 5 mM-75 mM, 20 mM-500 mM, 20 mM-250 mM, 20 mM-100 mM, 20 mM-75 mM, 40 mM-500 mM, 40 mM-250 mM, 40 mM-100 mM, 40 mM-75 mM, or 40 mM-60 mM phosphocreatine.

In one embodiment, the forward crRNA and the reverse crRNA are each present in the third container at a concentration of between 0.05 μM-5 μM, 0.05 μM-2.5 μM, 0.05 μM-1 μM, 0.05 μM-0.75 μM, 0.25 IM-5 μM, 0.25 μM-5 μM, 0.25 μM-2.5 μM, 0.25 μM-1 μM, 0.25 μM-0.75 μM, 0.5 μM-5 μM, 0.5 μM-5 μM, 0.5 μM-2.5 μM, 0.5 μM-1 μM, or 0.5 μM-0.75 μM. In another embodiment, the Cas12a is present in the third container at a concentration of between 0.01 μM-7.5 μM, 0.01 μM-5 μM, 0.01 μM-2.5 μM, 0.01 μM-2 μM, 0.1 μM-10 μM, 0.1 μM-7.5 μM, 0.1 μM-5 IM, 0.1 μM-2.5 μM, 0.1 μM-2 μM, 0.5 μM-10 μM, 0.5 μM-7.5 μM, 0.5 μM-5 μM 0.5 μM-2.5 μM, 0.5 μM-2 μM 0.75 μM-10 μM, 0.75 μM-7.5 μM, 0.75 μM-5 μM, 0.75 μM-2.5 μM, 0.75 μM-2 μM, 1 μM-10 μM, 1 μM-7.5 μM, 1 μM-5 μM, 1 μM-2.5 μM, 1 μM-2 μM, or 1 μM-1.5 μM.

In a further embodiment, the first container, the second container, and/or the third container have a pH between 7.0 and 8.5.

In one specific embodiment, the first container comprises about 100 mM potassium acetate, about 14 mM magnesium acetate, about 2 mM DTT, about 5% polyethylene glycol over 10,000 Daltons in molecular weight, about 1.2 mM dNTPs, about 3 mM ATP, about 50 mM phosphocreatine, about 0.1 μg/μL creatine kinase, about 320 nM each of the forward primer and the reverse primer; and the second container comprises about 8 μM the ssDNA-FQ reporter, about 0.03 μg/μL strand displacement DNA polymerase, about 0.9 μg/μL single-stranded DNA binding protein, about 0.12 μg/μL recombinase, and about 0.03 μg/μL recombinase loading agent. In another specific embodiment, the third container comprises about 0.64 μM each of the forward crRNA and the reverse crRNA, and about 1.28 μM of Cas12a protein or functional analogue thereof.

Examples

The recent outbreak of novel coronavirus (SARS-CoV-2) causing COVID-19 disease spreads rapidly in the world. Rapid and early detection of SARS-CoV-2 facilitates early intervention and prevents the disease spread. Here, an All-In-One Dual CRISPR-Cas12a (AIOD-CRISPR) assay is presented for one-pot, ultrasensitive, and visual SARS-CoV-2 detection. By targeting SARS-CoV-2's nucleoprotein gene, two CRISPR RNAs without protospacer adjacent motif (PAM) sites limitation are introduced to develop the AIOD-CRISPR assay and detect the nucleic acids with a sensitivity of few copies. The assay was validated by using COVID-19 clinical swab samples and obtain consistent results with RT-PCR assay. Furthermore, a low-cost hand warmer (~$0.3) is used as an incubator of the AIOD-CRISPR assay to detect clinical samples within 20 minutes, enabling an instrument-free, visual SARS-CoV-2 detection at the point of care. Thus, the method has the significant potential to provide a rapid, sensitive, one-pot point-of-care assay for SARS-CoV-2.

In this study, an All-In-One Dual CRISPR-Cas12a (termed AIOD-CRISPR) assay for simple, rapid, ultrasensitive, specific, one-pot and visual detection of SARS-CoV-2 is reported. Dual crRNAs without protospacer adjacent motif sites (PAM) sequence limitation are introduced to initiate dual CRISPR-based nucleic acid detection with high efficiency. In the AIOD-CRISPR assay, all components for nucleic acid amplification and CRISPR-based detection are thoroughly mixed in a single, one-pot reaction system and incubated at a single temperature (e.g., 37° C.), eliminating the need for separate pre-amplification and transfer of amplified product. By targeting the nucleoprotein (N) gene of SARS-CoV-2, the AIOD-CRISPR assay method is able to detect few copies of the nucleic acids (DNA or RNA). In addition, the AIOD-CRISPR method has been validated by testing 28 clinical swab samples and obtained consistent results with that of RT-PCR method. Furthermore, a low-cost hand warmer has been directly used to as its incubator for instrument-free point of care diagnostics of COVID-19.

Results

AIOD-CRISPR assay system. As shown in FIG. 1a, the AIOD-CRISPR assay system uses a pair of Cas12a-crRNA complexes generated by two individual crRNAs to bind two different sites which are close to the recognition sites of primers in the target sequence. The Cas12a-crRNA complexes are first prepared prior to being adding into the reaction solution containing RPA primers, single-stranded DNA fluorophore-quencher (ssDNA-FQ) reporter, recombinase, single-stranded DNA binding protein (SSB), strand-displacement DNA polymerase, and target sequences. When incubating the AIOD-CRISPR reaction system in one pot at ~37° C., the RPA amplification is initiated and exposes the binding sites of the Cas12a-crRNA complexes due to the strand displacement. On one hand, when the Cas12a-crRNA complexes bind the target sites, the Cas12a endonuclease is activated and cleaves the ssDNA-FQ reporters, generating strong fluorescence signals. On the other hand, the amplified products generated during the RPA continuously trigger CRISPR-Cas12a-based collateral cleavage activity. Therefore, target sequences for the AIOD-CRISPR assay are not limited by the Cas12a's PAM sequences.

Figure 6:
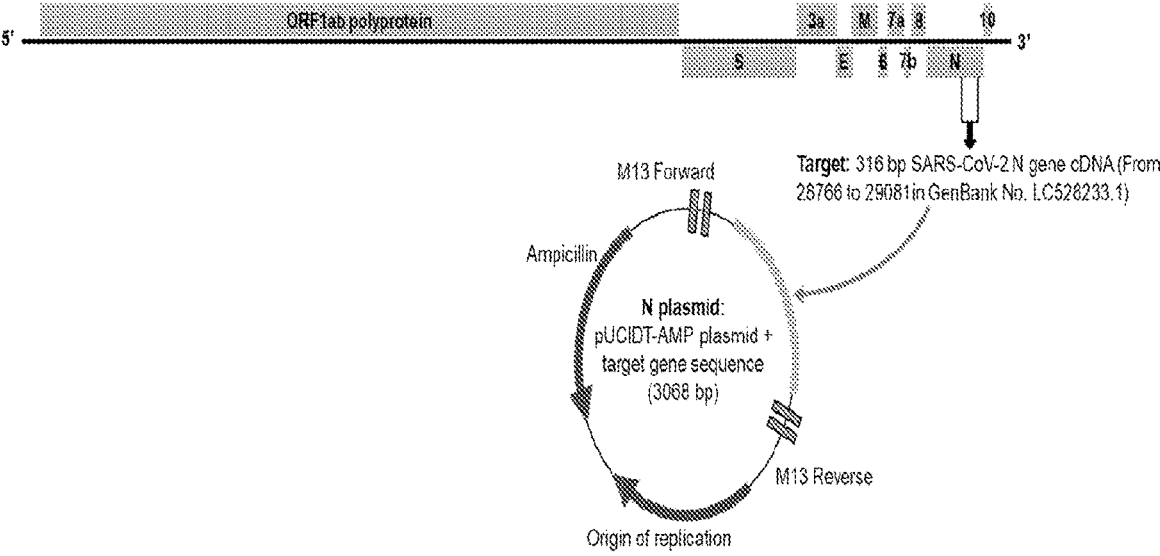
FIG. 6. The pUCIDT-AMP plasmid (from IDT) containing the 316 bp SARS-CoV-2 N gene cDNA (N plasmid) fragment and its location at the genome map.

To systematically evaluate the AIOD-CRISPR assay system, eight reaction systems (reactions #1-8) with various components (FIG. 1b) were prepared and tested. A plasmid containing 316 bp SARS-CoV-2 N gene fragment, termed N plasmid, was used as the target sequences (FIG. 6). The ssDNA-FQ reporter was a 5 nucleotide (nt) single-stranded DNA (5'-TTATT-3) labelled by 5' 6-FAM (Fluorescein) fluorophore and 3' Iowa Black™ FQ quencher. After incubation at 37° C. for 40 min, only reaction #4 containing target nucleic acid sequence, dual crRNAs, Cas12a, and RPA reaction mixture produced super-bright fluorescence signal (FIG. 1b), which could be directly visualized under a blue LED or UV light illuminator. Surprisingly, even under ambient light conditions without excitation, a color change from orange-yellow to green was directly observed in the reaction tube #4 by naked eyes. To further verify the specificity of the generated fluorescence signal, the assay products (self-probed fluorescence reporters) were subjected to denaturing polyacrylamide gel electrophoresis (PAGE). As shown in FIG. 1b, a strong band with shorter DNA size was observed only in the lane of reaction #4, which resulted from the cleaved ssDNA-FQ reporters with strong fluorescence signal. In comparison, for other reaction systems, only weak bands with relatively longer DNA sizes were observed in their corresponding lanes, which may be attributed to fluorescence quench of the intact uncut ssDNA-FQ reporters. In addition, in real-time fluorescence curves, only reaction #4 showed a significantly increased fluorescence signal that saturated at 13 min (FIG. 1b). Thus, these results show that the AIOD-CRISPR assay provides a simple, rapid, one-pot approach for target-specific nucleic acid detection.

Figure 7:
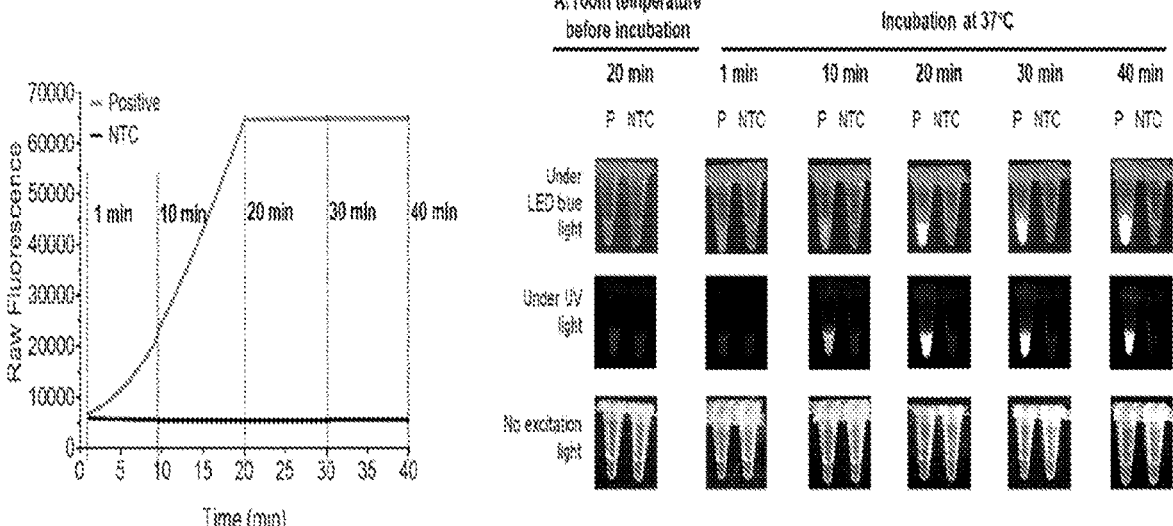
FIG. 7. The AIOD-CRISPR assay incubated at room temperature for 20 min and at 37° C. for 1, 10, 20, 30, and 40 min. Positive (P), $3×10^3$ copies of the plasmid DNA containing SARS-CoV-2 N gene sequence. NTC, non-target control reaction.

To determine if nucleic acid amplification is efficiently initiated at room temperature during sample preparation in the AIOD-CRISPR assay system, two AIOD-CRISPR solutions were prepared (one positive and one negative) and allowed them to remain at room temperature for 20 min. As shown in FIG. 7, very weak fluorescence change between positive and negative samples was observed in the AIOD-CRISPR systems at room temperature. In comparison, there's a significant fluorescence change at 37° C. after as short as 10 min incubation (FIG. 7). Eventually, the fluorescence signal was saturated and a color change from orange-yellow to green was present after 20-min incubation at 37° C. Therefore, the AIOD-CRISPR assay system is mainly triggered after reaction temperature is elevated to −37° C.

Figure 8:
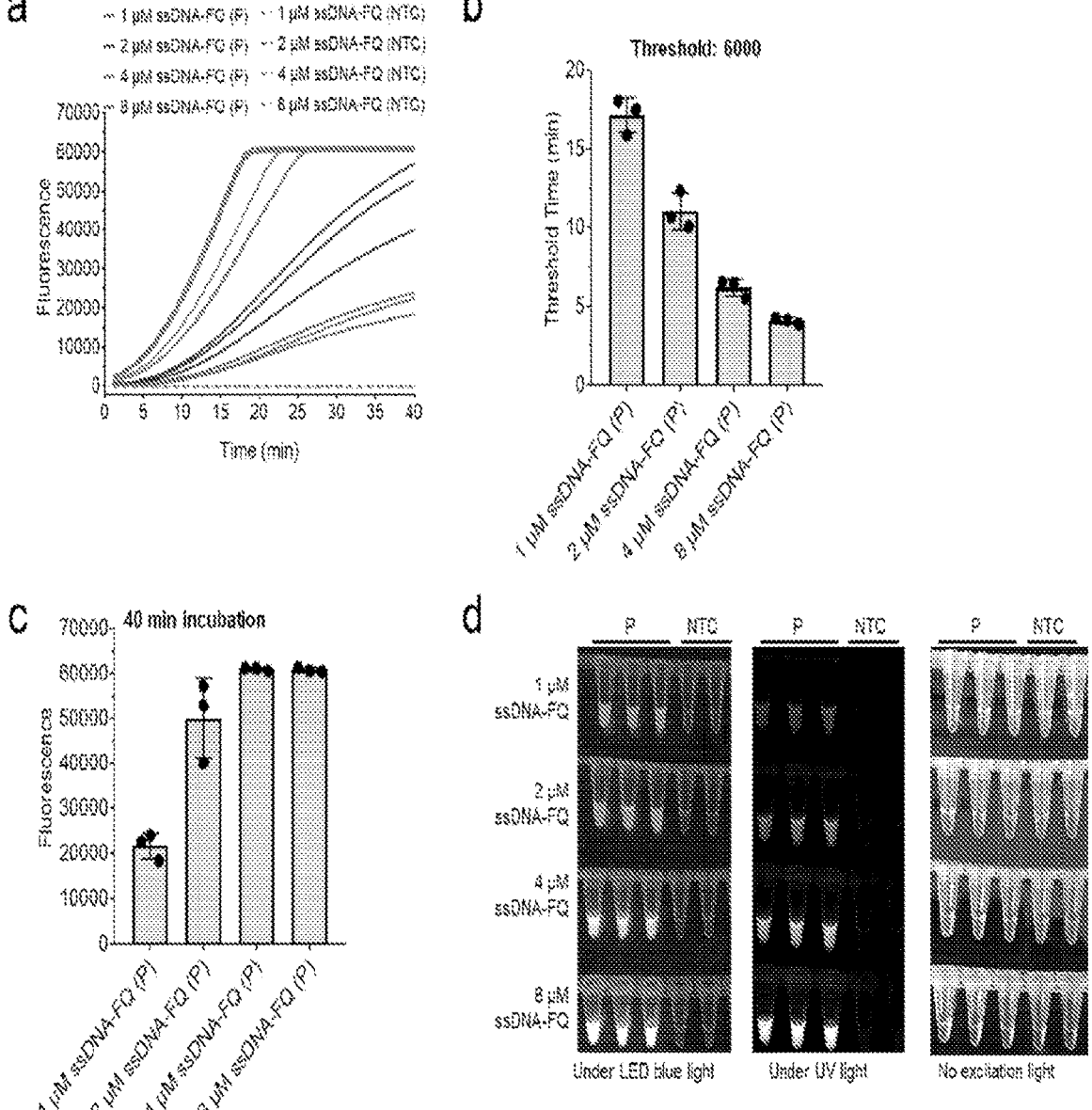
FIG. 8a-d. The AIOD-CRISPR assay with various concentrations of the ssDNA-FQ reporters. a Real-time fluorescence detection. b Threshold time comparison. c Endpoint fluorescence intensity comparison after 40 min incubation. d Visual detection comparison after 40 min incubation. P, $3×10^3$ copies of the plasmid DNA containing SARS-CoV-2 N gene sequence. NTC, non-target control reaction. Error bars represent the means±s.d. from three replicates (n=3).
Figure 9:
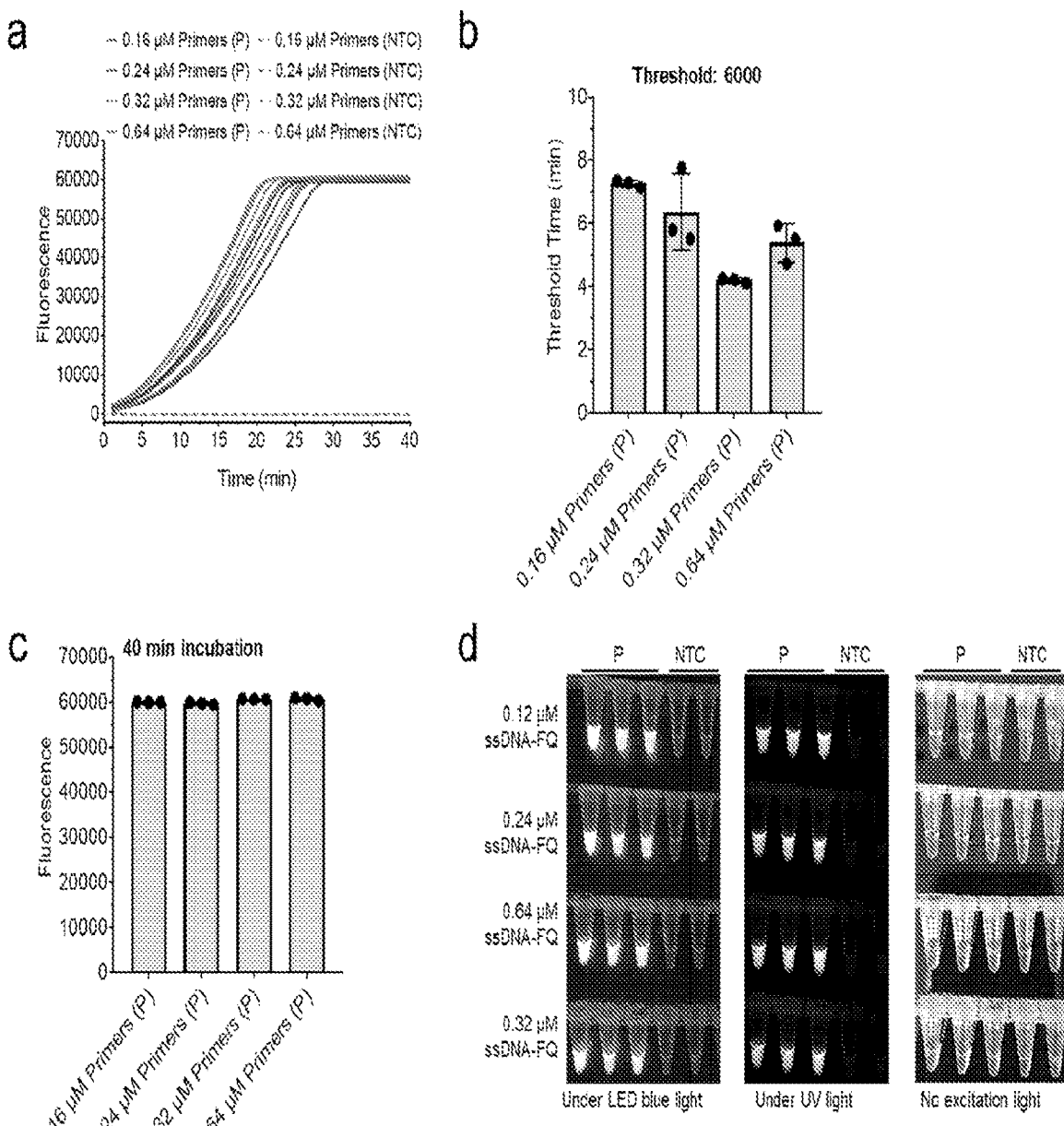
FIG. 9a-d. The AIOD-CRISPR assay with various concentrations of the primers, a Real-time fluorescence detection. b Threshold time comparison. c Endpoint fluorescence intensity comparison after 40 min incubation. d Visual detection comparison after 40 min incubation. P, $3×10^3$ copies of the plasmid DNA containing SARS-CoV-2 N gene sequence. NTC, non-target control reaction. Error bars represent the means±s.d. from three replicates (n=3).
Figure 10:
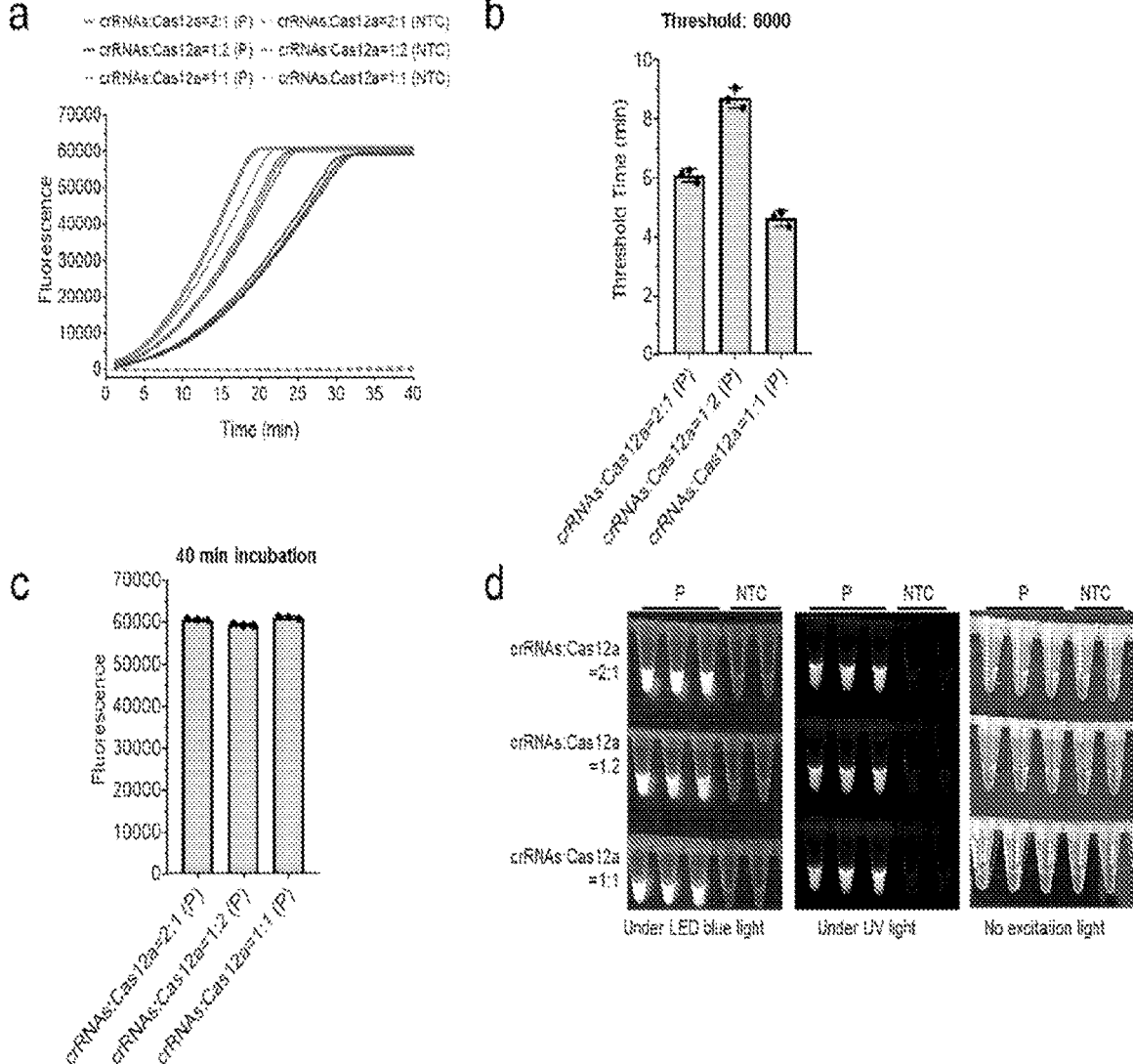
FIG. 10a-d. The AIOD-CRISPR assay with various ratios of crRNAs to Cas12a (the concentration of each of crRNAs was fixed at 0.64 µM). a Real-time fluorescence detection. b Threshold time comparison. c Endpoint fluorescence intensity comparison after 40 min incubation. d Visual detection comparison after 40 min incubation. P, $3×10^3$ copies of the plasmid DNA containing SARS-CoV-2 N gene sequence. NTC, non-target control reaction. Error bars represent the means±s.d. from three replicates (n=3).

Modifications to AIOD-CRISPR assay. ssDNA-FQ reporters were modified in the AIOD-CRISPR assay because the reporter concentration plays a crucial role in fluorescence readout. As shown in FIGS. 8a and b, the higher the concentration of the ssDNA-FQ reporters, the shorter the threshold time. As to fluorescence intensity, the minimal concentration for saturated values was 4 μM after 40 min incubation (FIG. 8c). For better visual colorimetric detection, 8 μM ssDNA-FQ was the best choice (FIG. 8d). Collateral cleavage efficiency of the activated Cas12a nuclease represents an ability to cut ssDNA-FQ reporters around it. Thus, increasing the ssDNA-FQ reporter concentration can improve the fluorescence signals. By choosing 8 μM ssDNA-FQ, the effect of the primer concentration and the ratio of crRNAs to Cas12a on the AIOD-CRISPR assay was next investigated by fixing the concentration of each crRNA at 0.64 μM. As shown in FIGS. 9 and 10, the concentration of the primers and the ratio of crRNAs to Cas12a that performed best was 0.32 μM and 1:1, respectively.

Figure 2:
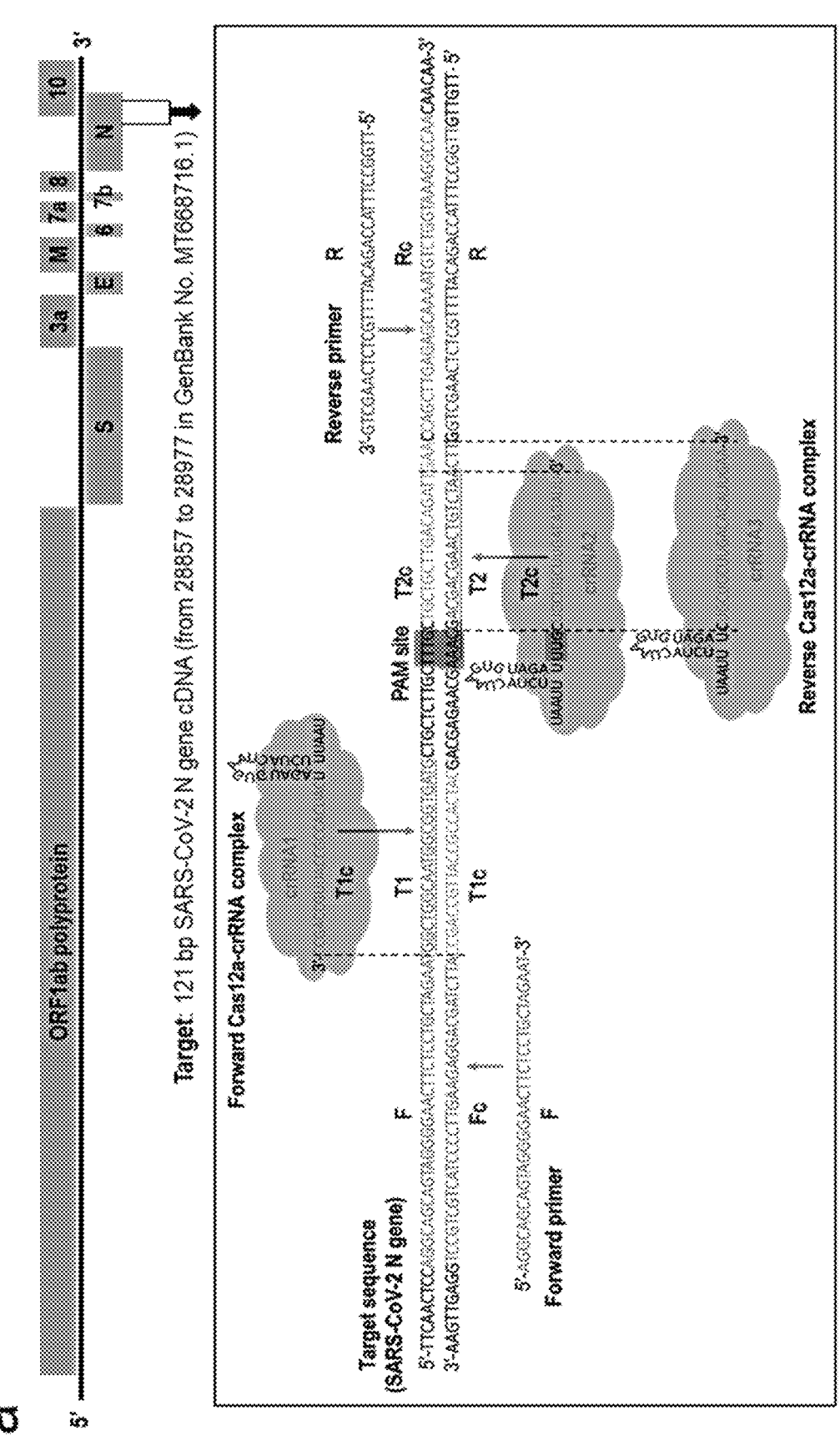
FIG. 2a-c. Primer design and the sensitivity of AIOD-CRISPR for the detection of the ten-fold serial dilution of plasmid DNA containing SARS-CoV-2 N gene sequence (N plasmid). a SARS-CoV-2 genome map with the detailed sequence information of the designed primers and crRNAs targeting the N gene sequence. For comparison purpose, the designed crRNA1 and crRNA2 were not limited by the PAM site (5'-TTTCG-3'), while the crRNA3 was limited by the PAM site. (Target Sequence is SEQ ID NO: 9; Forward primer is SEQ ID NO: 2; Reverser Primer is SEQ ID NO: 3; forward Cas12a-crNA complex is SEQ ID NO: 4; reverse Cas12a-crRNA2 complex is SEQ ID NO: 5; crRNA3 is SEQ ID NO: 6) b Real-time/endpoint AIOD-CRISPR assay using dual crRNAs (crRNA1&2) without PAM site limitation. c Real-time/endpoint AIOD-CRISPR assay using single crRNA (crRNA3) with PAM site limitation. Four replicates were run (n=4). The horizontal dashed line indicates the cut-off fluorescence that was defined by the average intensity of NTC plus 3 times of the standard deviation. NTC, non-template control reaction. Error bars represent the means±standard deviation (s.d.) from replicates. The unpaired two-tailed t-test was used to analyze the statistical significance.
Figure 2:
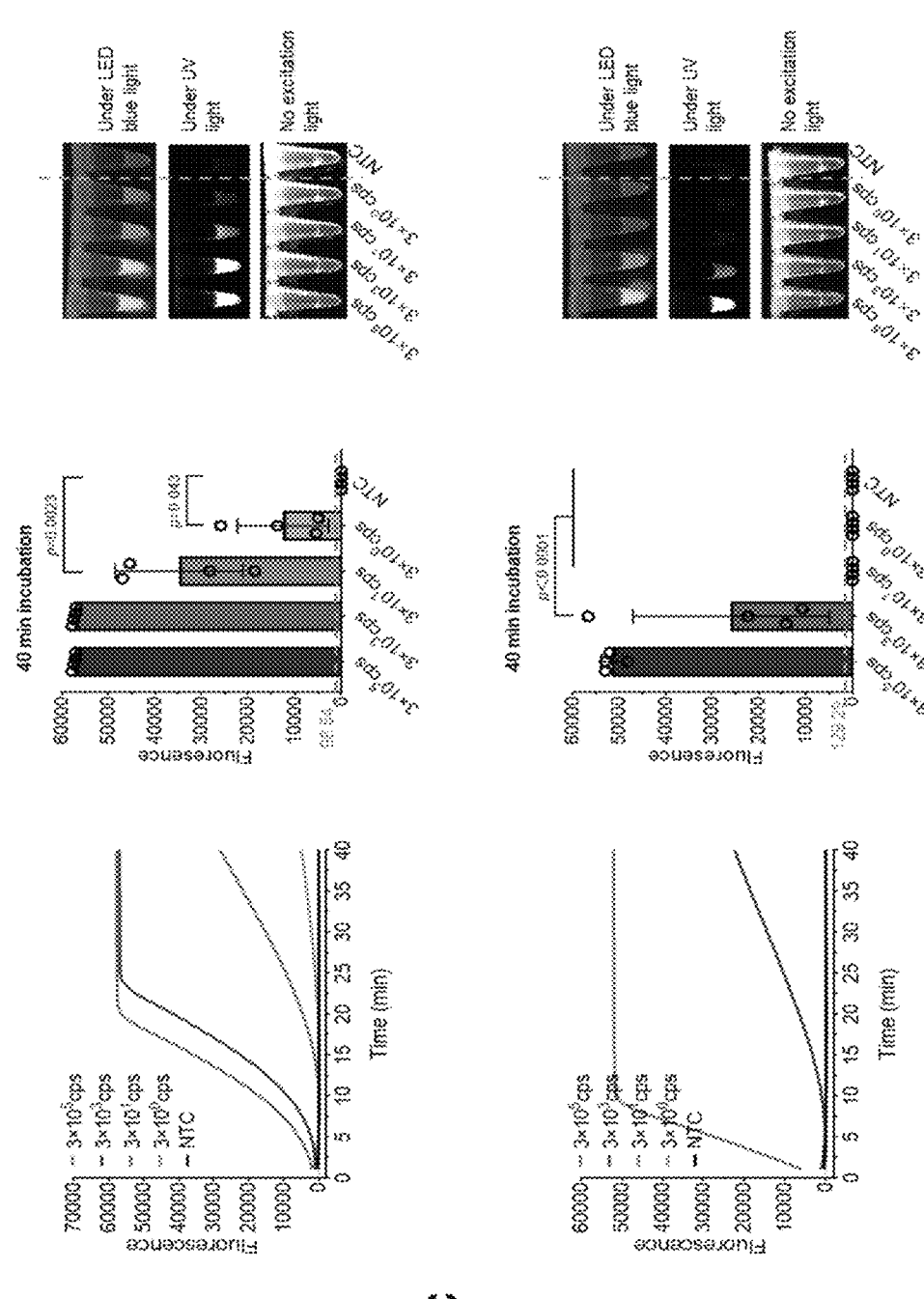
Figure 11:
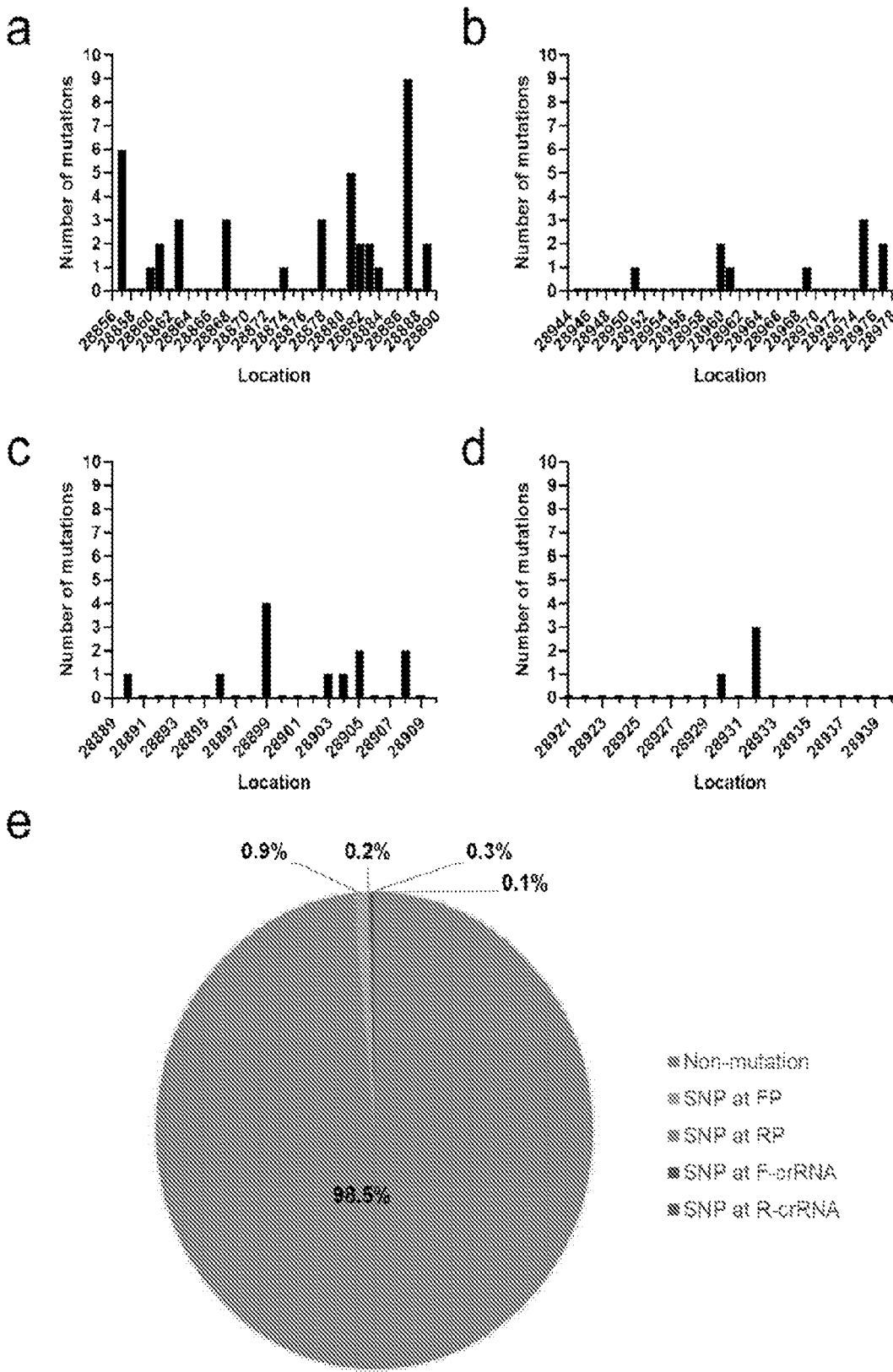
FIG. 11a-e. Number of mutations at each nucleotide location in the primers and crRNAs of AIOD-CRISPR assays based on multiple sequence alignments analysis of 4463 SARS-CoV-2 genomes sampled between December 2019 and August 2020, a-d Number of mutations at each nucleotide location in forward primer (FP), reverse primer (FP), forward crRNA (F-crRNA), and reverse crRNA (R-crRNA). e Percentage of the single nucleotide polymorphism (SNP) mutation when considering each mutation as a SNP mutation. The data were from GISAID-provided genomic epidemiology of hCoV-19 (as of Aug. 14, 2020).
Figure 12:
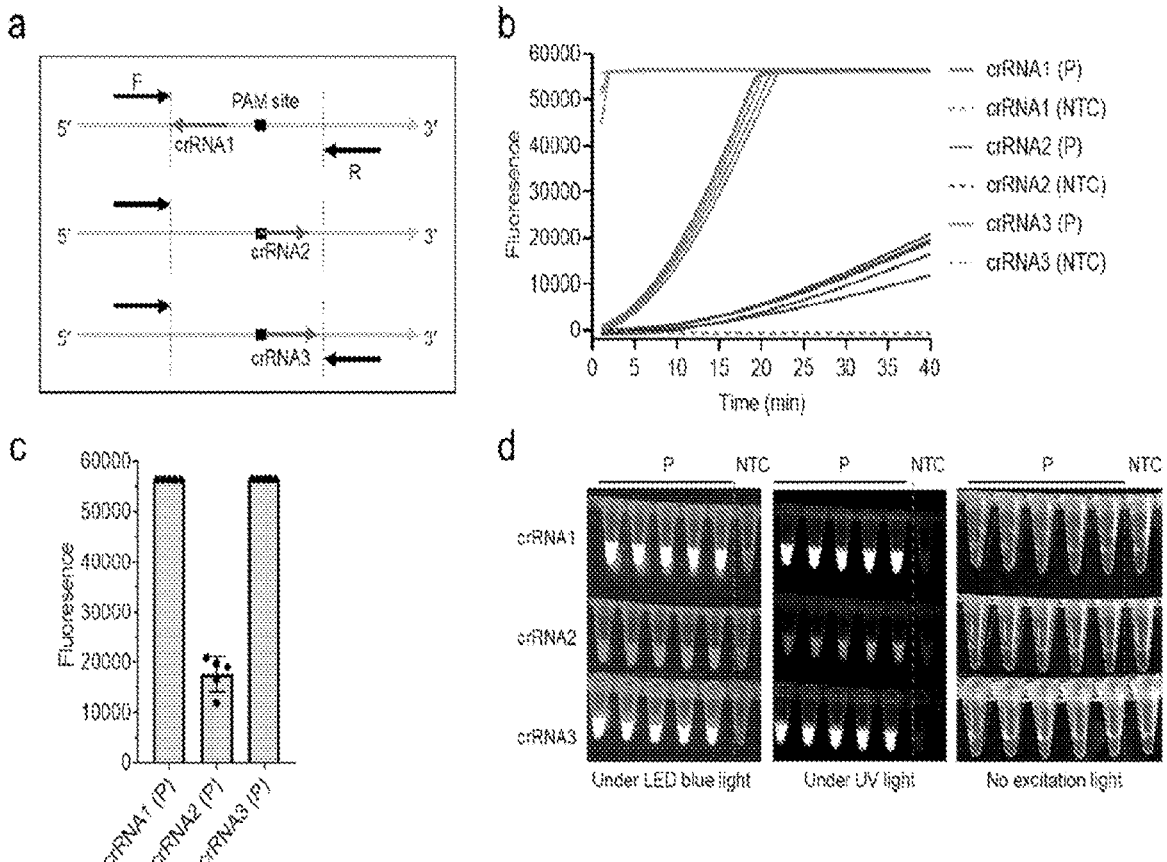
FIG. 12a-d. Comparison of AIOD-CRISPR assays using different single crRNA for the detection of $3×10^6$ copies of plasmid DNA containing SARS-CoV-2 N gene sequence (N plasmid). a Primer design and the location of each crRNA. Among them, the design of crRNA1 and crRNA2 were not limited by the PAM site, while the design of crRNA3 was limited by the PAM site. Detailed sequences were displayed in FIG. 2a. b Real-time fluorescence monitoring curves. c Endpoint fluorescence comparison after 40 min incubation. d Visual detection comparison after 40 min incubation. Five replicates were run (n=5) for each positive reaction. P, the positive reaction with $3\times10^6$ copies N plasmids. NTC, non-template control reaction. Error bars represent the means±s.d. from replicates.
Figure 13:
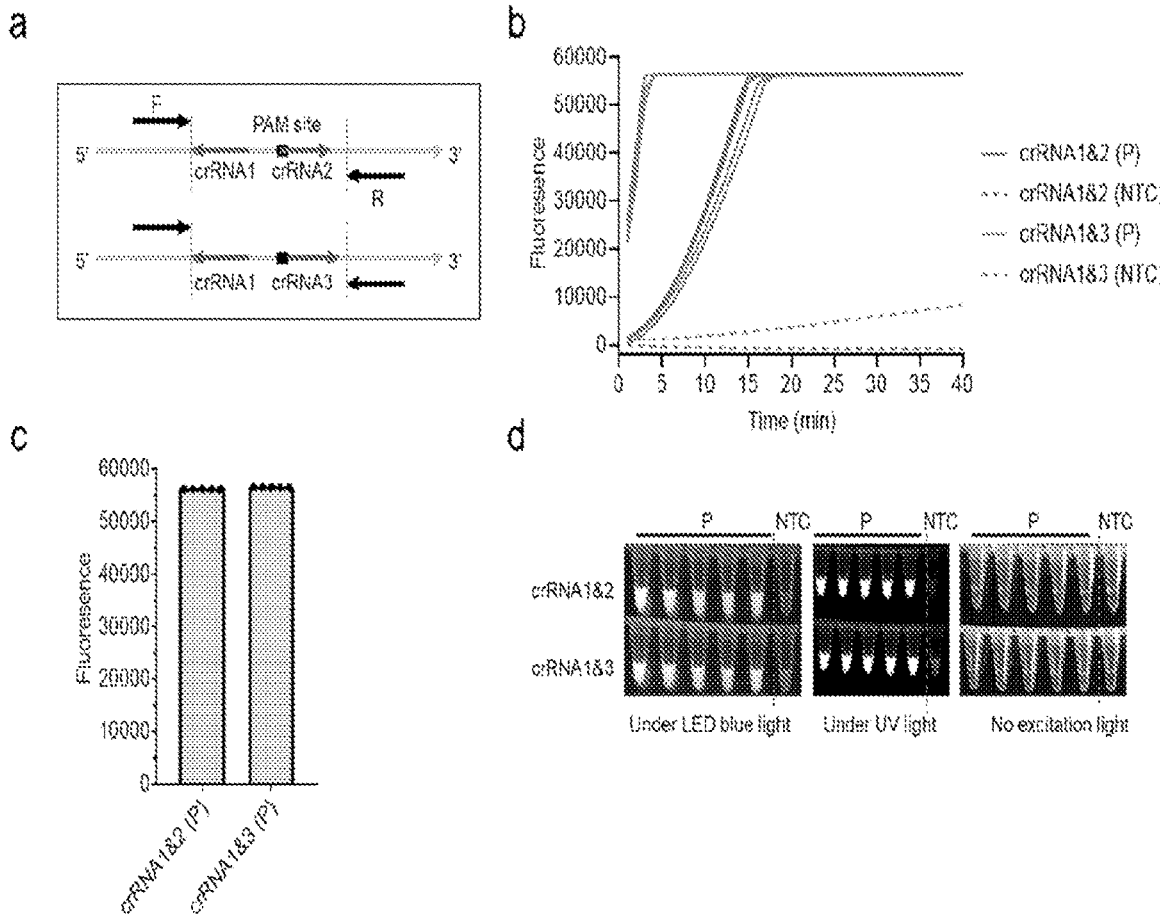
FIG. 13a-d. Comparison of AIOD-CRISPR assays using different pairs of dual crRNAs for the detection of $3\times10^6$ copies of plasmid DNA containing SARS-CoV-2 N gene sequence (N plasmid). a Design and location of primers and crRNAs. Detailed sequences were displayed in FIG. 2a. b Real-time fluorescence monitoring curves. c Endpoint fluorescence comparison after 40 min incubation. d Visual detection comparison after 40 min incubation. Five replicates were run for each positive reaction (n=5). P, the positive reaction with 3' $10^6$ copies N plasmids. NTC, non-template control reaction. Error bars represent the means±s.d. from replicates.
Figure 14:
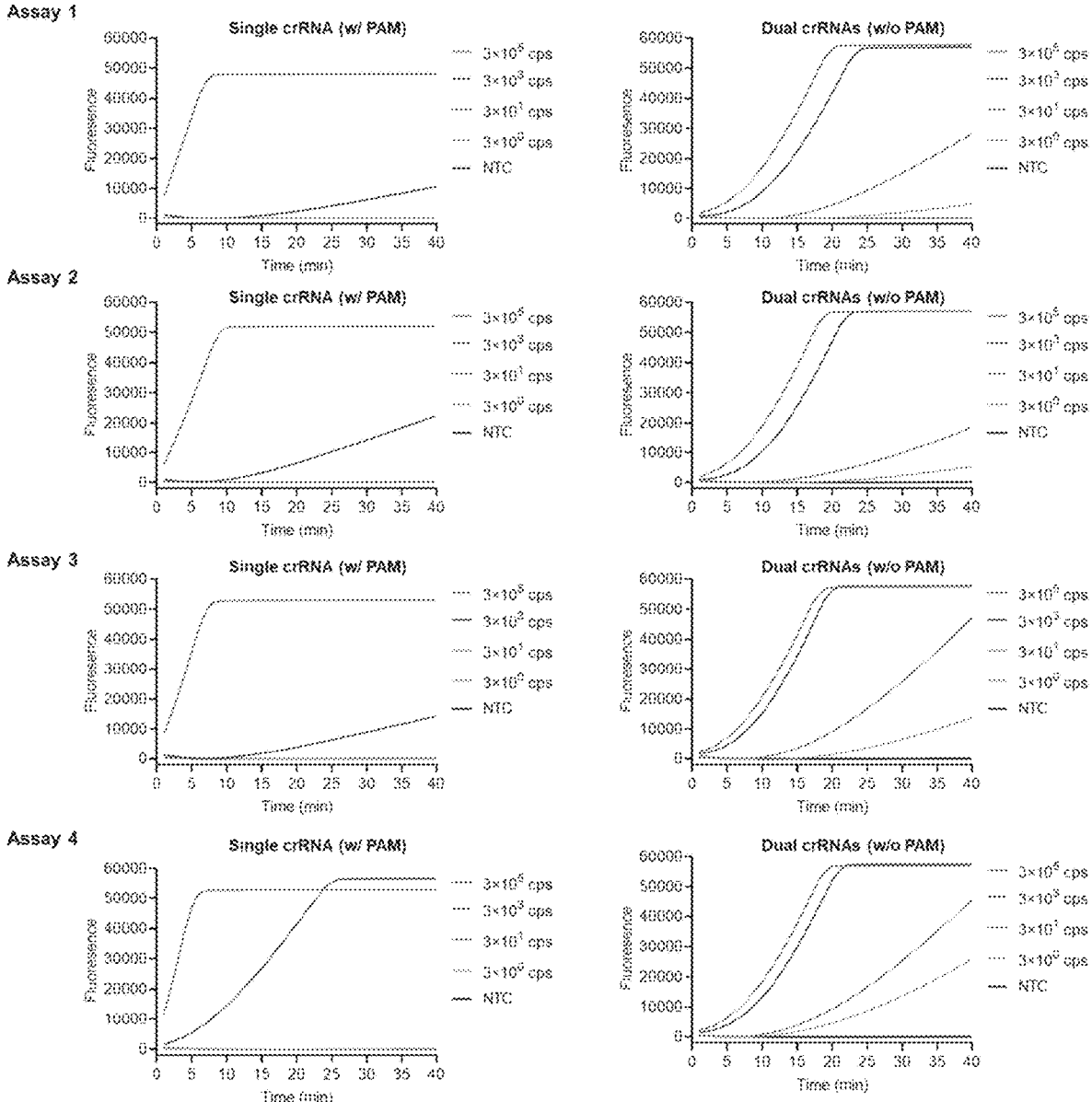
FIG. 14. Sensitivity comparison of AIOD-CRISPR assays using single crRNA (crRNA3) with PAM site limitation or the dual crRNAs (crRNA1&2) without PAM site limitation for detection of the ten-fold serial dilution of plasmid DNA containing SARS-CoV-2 N gene sequence. Detailed sequences were displayed in FIG. 2a. Four independent assays were conducted. NTC, non-template control reaction.

The primers are designed to amplify 121 bp of SARS-CoV-2 N gene sequence with the location from 28857 to 28977 in the SARS-CoV-2 genome map (GenBank accession MT688716.1) as shown in FIG. 2a. The four target sites for primers and crRNAs were highly conserved for SARS-CoV-2 with a theoretical mutation rate of less than 1.5%, according to the public data provided by Global Initiative on Sharing All Influenza Data (GISAID) (FIG. 11).[21] Previous studies have proved that the collateral cleavage of ssDNA-FQ reporters by the Cas12a nuclease is triggered by the binding of crRNA to target sites. Thus, the AIOD-CRISPR assays were investigated by using three different crRNAs (crRNA1, crRNA2, and crRNA3) (FIG. 2a) which were specific to different sites in the same amplification region. Among of them, crRNA3 was designed with PAM site (5'-TTTG-3') limitation, while crRNA1 and crRNA2 not. Under the conditions of ssDNA-FQ reporter (8 μM), primer concentration (0.32 μM), and ratio of crRNAs to Cas12a (1:1), the AIOD-CRISPR assays were evaluated using single crRNA (crRNA1, crRNA2, and crRNA3) for the detection of 3-10$^6$ copies plasmid DNA. As shown in FIG. 12b, the single crRNA3 with PAM sequence limitation showed the fastest fluorescence response than that of crRNA1 and crRNA2 without PAM sequence limitation. Next, the performance of dual crRNAs (crRNA1&2 and crRNA1&3) were compared. As shown in FIG. 13b, although crRNA1&3 showed the faster fluorescence response than crRNA1&2, it triggered the non-specific fluorescence signals in negative controls, which may potentially lead to an increased risk of false positive. Thus, the sensitivities of the AIOD-CRISPR assays with dual crRNA1&2 without PAM sequence limitation and single crRNA3 with PAM sequence limitation were determined. As shown in FIG. 2b, c and FIG. 14, the AIOD-CRISPR assay with crRNA1&2 without PAM sequence limitation can consistently detect 3 copies of SARS-CoV-2 plasmid DNA, which is much higher than that of single crRNA3 with PAM sequence. The lower sensitivity of single crRNA3 with PAM sequence in the AIOD-CRISPR assay is likely attributed to that the templates at low concentrations are rapidly cleaved by highly activated Cas12a from the crRNA3 with PAM sequence, thereby decreasing the amplification efficiency. Therefore, dual crRNAs without PAM sequence enables highly sensitive AIOD-CRISPR assay and eliminates the requirement of PAM sequence limitation.

SARS-CoV-2 detection by AIOD-CRISPR assay. To evaluate the detection specificity, the AIOD-CRISPR assay was tested using commercially available control plasmids containing the complete N gene from SARS-CoV-2 (SARS-CoV-2_PC, Catalogue #10006625, IDT), SARS (SARS-CoV control, Catalogue #10006624, IDT), and Middle East respiratory syndrome (MERS) (MERS-CoV (Middle East respiratory syndrome coronavirus) control, Catalogue

Figure 3:
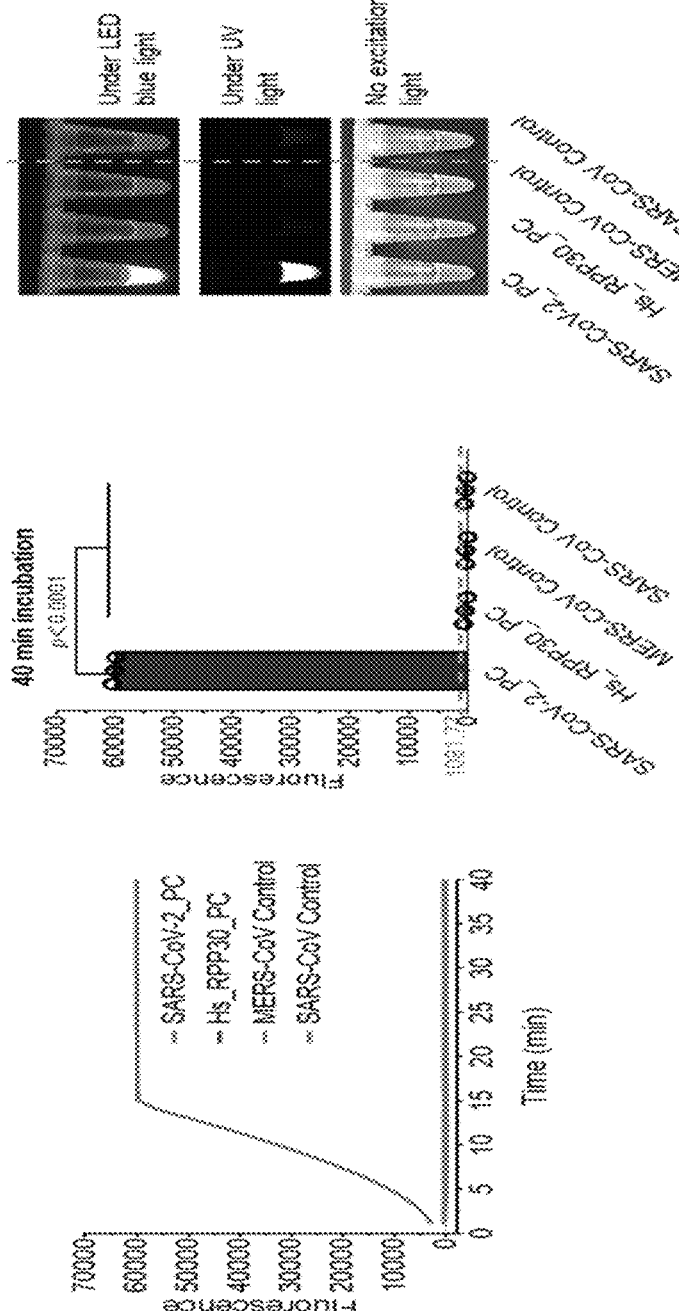
FIG. 3a-b. Specificity of AIOD-CRISPR and sensitivity of RT-AIOD-CRISPR for detection of synthetic SARS-CoV-2 N RNA sequences. a Specificity of real-time/endpoint AIOD-CRISPR assay for SARS-CoV-2 N detection. Three replicates were run (n=3). b Real-time/endpoint RT-AIOD-CRISPR detection of the ten-fold serial dilution of synthetic SARS-CoV-2 N RNA sequences. Four replicates were run (n=4). The horizontal dashed line indicates the cut-off fluorescence that was defined by the average intensity of NTC plus 3 times of the standard deviation. NTC, non-template control reaction. Error bars represent the means±s.d. from replicates. The unpaired two-tailed t-test was used to analyse the statistical significance.
Figure 3:
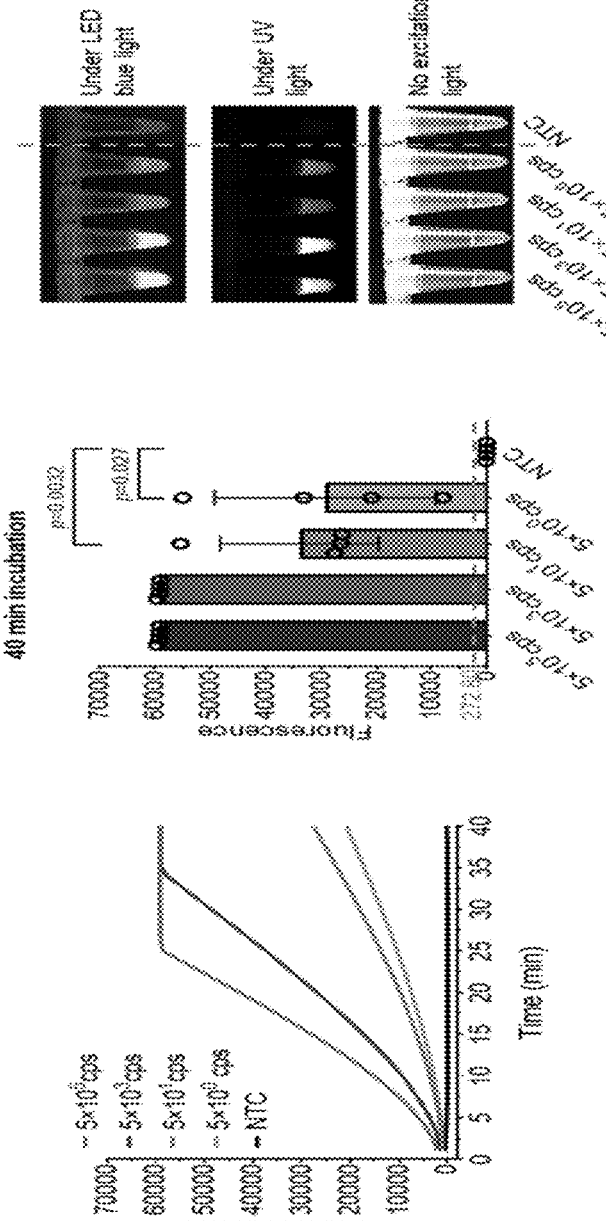
Figure 15:
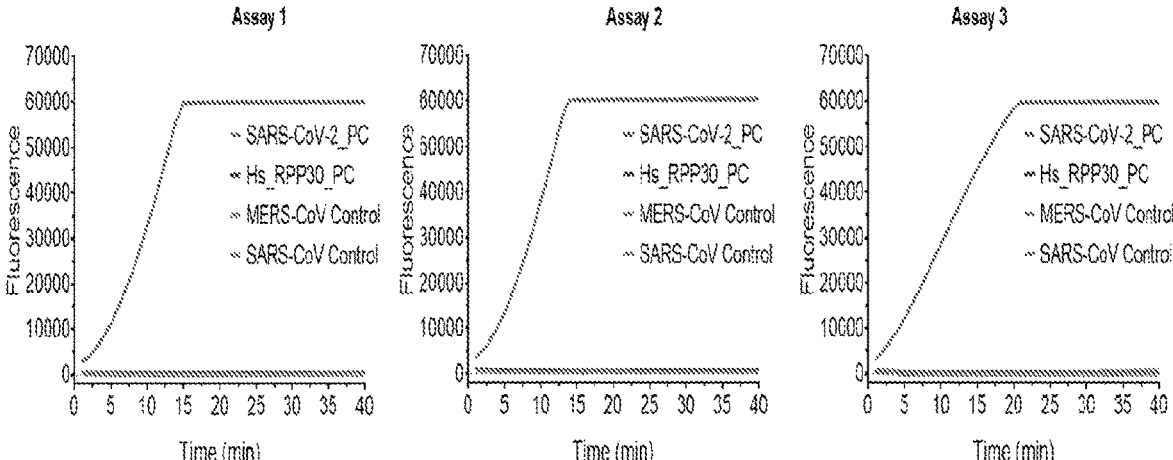
FIG. 15. AIOD-CRISPR specificity for SARS-CoV-2 N detection in three independent assays. IDT company provided the complete N gene from SARS-CoV-2 (SARS-CoV-2_PC, Catalogue #10006625, IDT), SARS (SARS-CoV_PC, Catalogue #10006624, IDT), and Middle East respiratory syndrome (MERS) (MERS-CoV (Middle East respiratory syndrome coronavirus)_PC, Catalogue #10006623, IDT), as well as the Hs_RPP30 control (Hs_RPP30_PC, Catalogue #10006626, IDT) with a portion of human RPP30 gene.

10006623, IDT), as well as the Hs_RPP30 control (Hs_RPP30_PC, Catalogue #10006626, IDT) with a portion of human RPP30 gene. FIG. 3a and FIG. 15 showed that only the reaction with SARS-CoV-2_PC had the positive signal in both real-time and visual detections, demonstrating that the AIOD-CRISPR assay possesses high specificity without cross reactions for non-SARS-CoV-2 targets.

Figure 16:
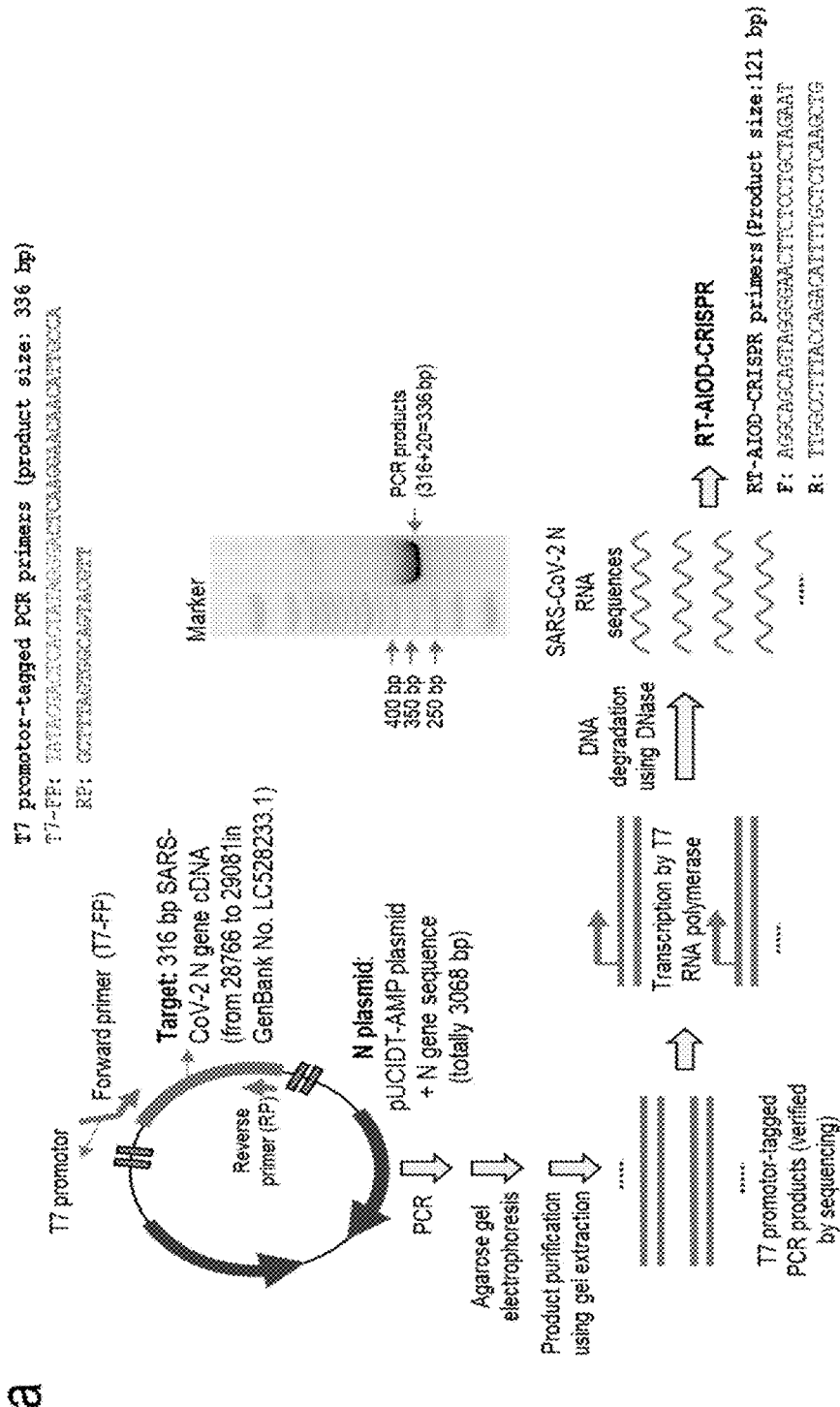
FIG. 16a-b. a Protocol and PCR primers for preparing the SARS-CoV-2 N RNA sequences. (T7 promotor-tagged PCT primers FP is SEQ ID NO: 7 and RP is SEQ ID NO: 8; RT AIOD CRISPR primers F is SEQ ID NO: 2 and R is SEQ ID NO: 3) b Sanger sequencing of the RT-AIOD-CRISPR detection region in the prepared SARS-CoV-2 N RNA (SEQ ID NO: 10).
Figure 16:
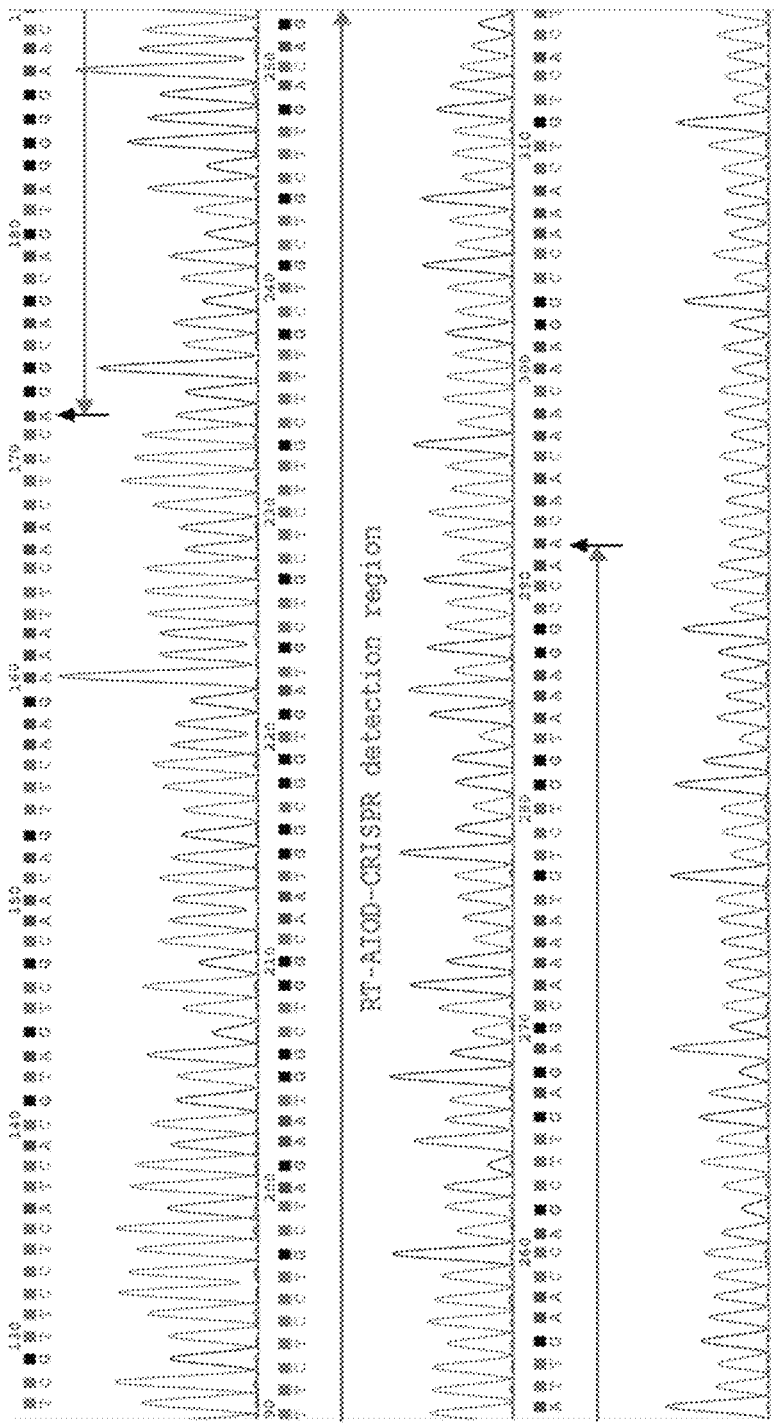
Figure 17:
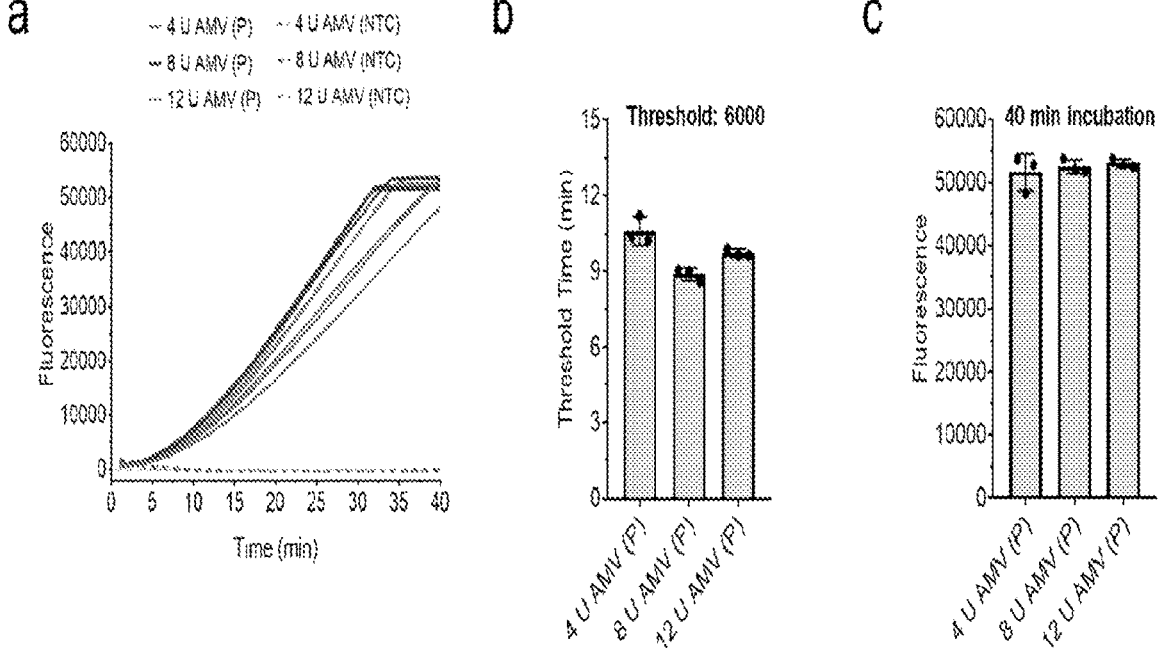
FIG. 17a-c. The RT-AIOD-CRISPR assay using various concentrations of AMV reverse transcriptase. a Real-time fluorescence detection. b Threshold time comparison. c Endpoint fluorescence intensity comparison after 40 min incubation. P, the positive reaction with $5\times10^3$ copies of SARS-CoV-2 N RNA sequences. NTC, non-target control reaction. Three replicates were run for each reaction or test. Error bars represent the means±s.d. from replicates.
Figure 18:
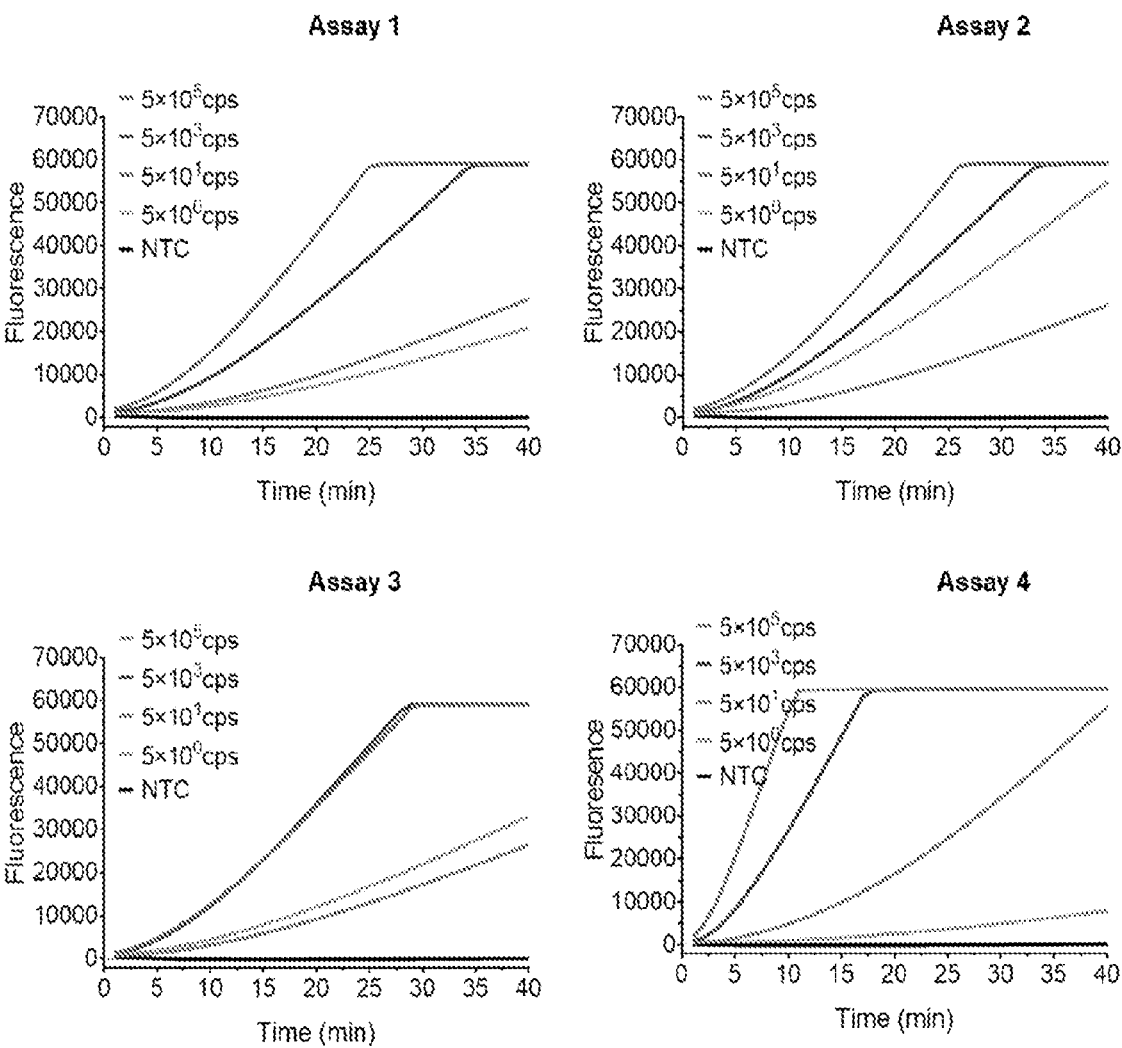
FIG. 18. Sensitivity of RT-AIOD-CRISPR assay for the detection of SARS-CoV-2 synthetic RNA templates in four independent assays. NTC, non-target control reaction.

Next, T7 promotor-tagged PCR and T7 RNA polymerase were used to prepare SARS-CoV-2 N gene RNA sequences (FIG. 16) and developed reverse transcription AIOD-CRISPR (RT-AIOD-CRISPR) assay by supplementing the AMV reverse transcriptase (8 U) (FIG. 17). As shown in FIG. 3b and FIG. 18, the RT-AIOD-CRISPR assay could consistently detect down to about 5 copies of SARS-CoV-2 N RNA targets in both real-time and visual detections.

Therefore, by targeting the SARS-CoV-2 N gene, the AIOD-CRISPR assay method was able to detect the nucleic acids with a sensitivity of few copies, providing a rapid, highly sensitive and specific method for SARS-CoV-2 detection.

Figure 4:
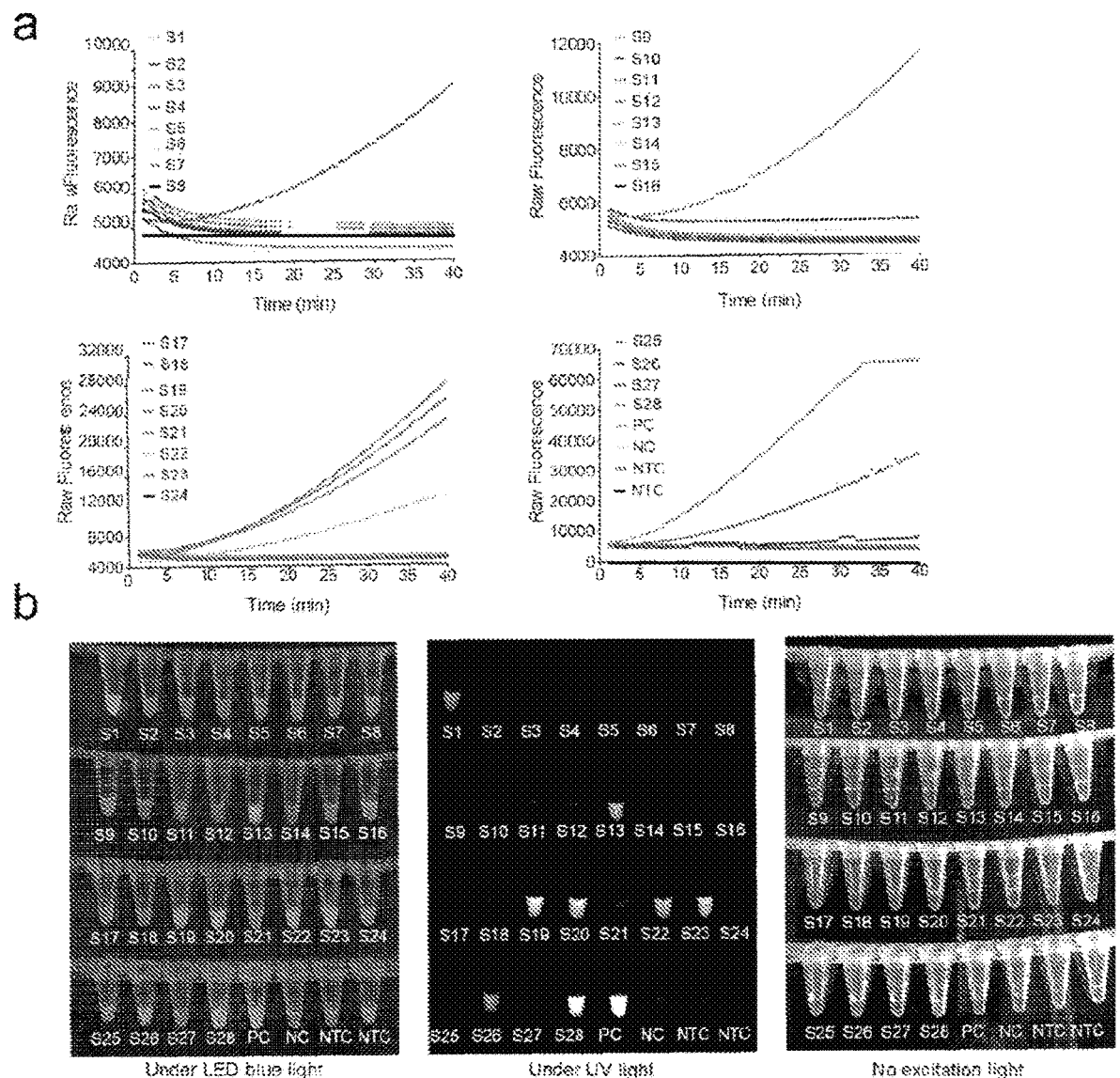
FIG. 4a-b. Detection of SARS-CoV-2 in clinical swab samples by RT-AIOD-CRISPR assay. a Real-time RT-AIOD-CRISPR detection. b Endpoint fluorescence/visual detection after 40 min incubation. PC, positive controls with $4.6×10^4$ copies of synthetic SARS-CoV-2 N RNA. S1-S28, clinical sample 1-28. NC, SARS-CoV-2-negative control reaction. NTC, non-template control reaction.
Figure 19:
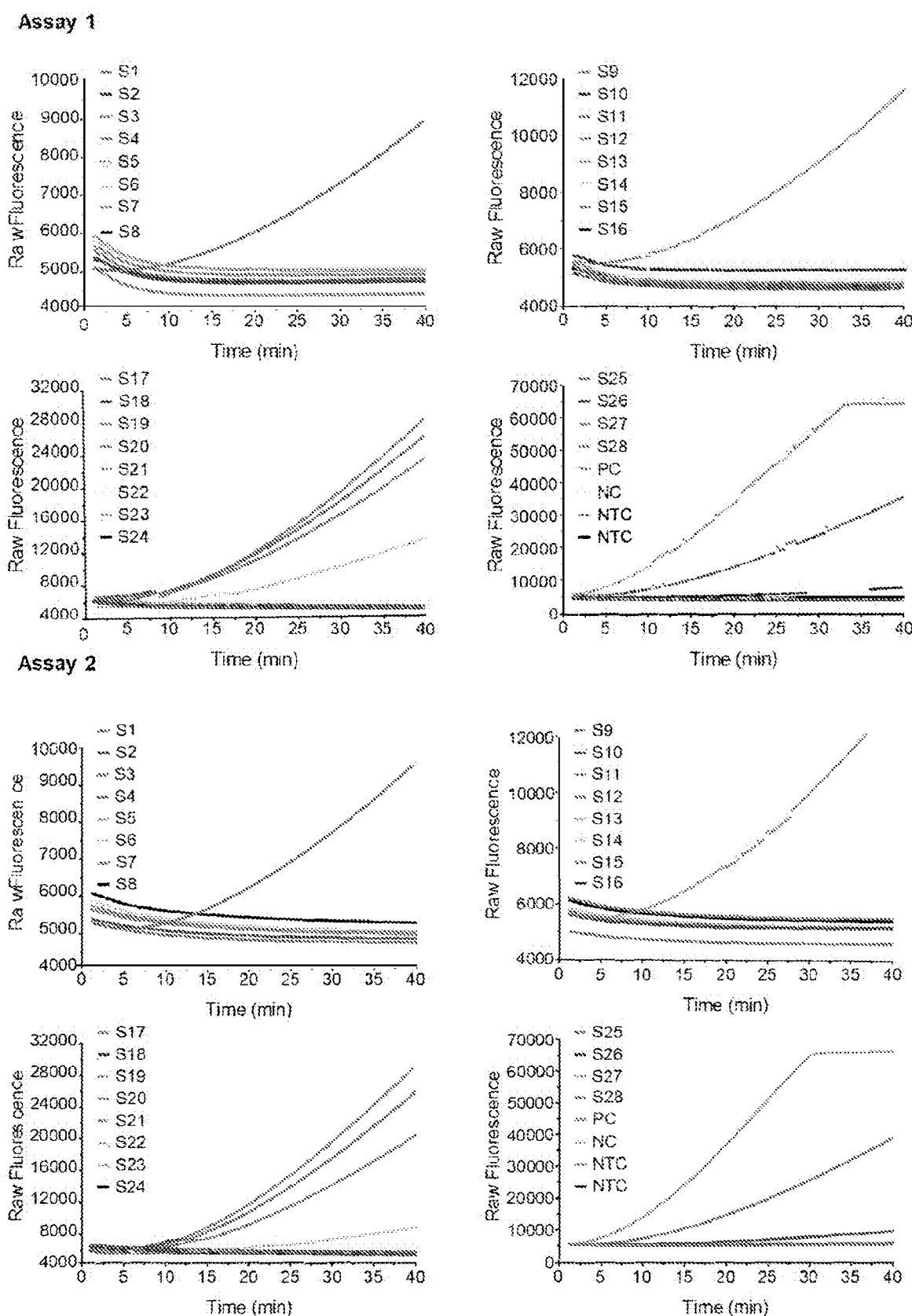
FIG. 19. Real-time RT-AIOD-CRISPR assay for SARS-CoV-2 detection in 28 clinical swab samples in two independent assays. Positive control (PC), $1.2\times10^6$ of synthetic SARS-CoV-2 N RNA. S1-S28, clinical samples 1-28. NC, SARS-CoV-2-negative control. NTC, non-template control reaction.
Figure 20:
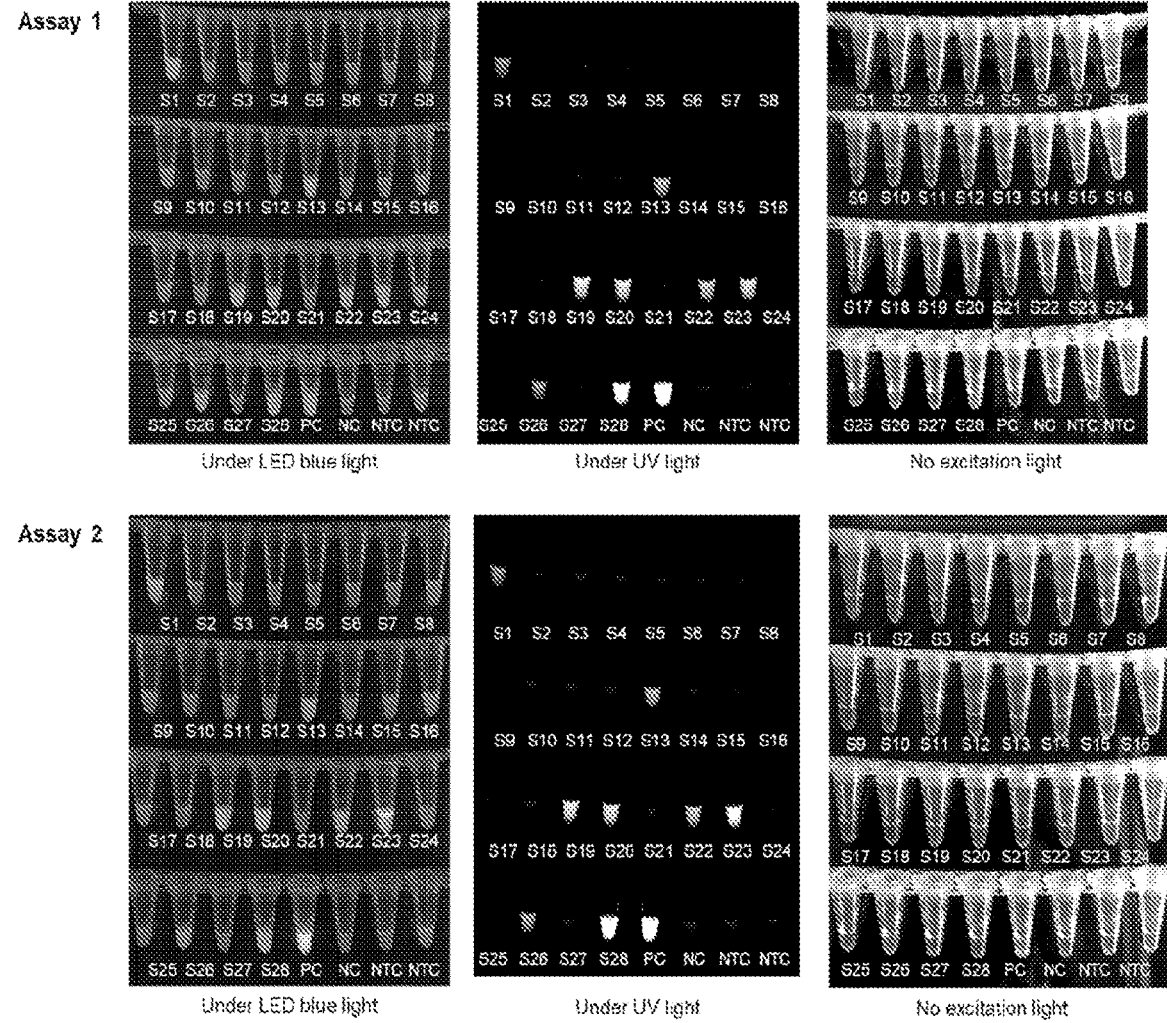
FIG. 20. Endpoint fluorescence/visual RT-AIOD-CRISPR assay for SARS-CoV-2 detection in 28 clinical swab samples in two independent assays. Positive control (PC), $1.2\times10^6$ of synthetic SARS-CoV-2 N RNA. S1-S28, clinical samples 1-28. NC, SARS-CoV-2-negative control. NTC, non-template control reaction.

Clinical validation and instrument-free point of care diagnostics. Given the outstanding performance, the RT-AIOD-CRISPR assay was further applied to detect SARS-CoV-2 from COVID-19 patient samples. A total of 28 de-identified clinical swab samples (including eight COVID-19 positive samples) were tested in the RT-AIOD-CRISPR assay by using their RNA extracts. To ensure the detection reliability, each sample was tested twice in two independent assays. As shown in FIG. 4a and FIG. 19, all eight COVID-19 positive samples were identified to be SARS-CoV-2-positive by our real-time RT-AIOD-CRISPR assay in 40 min, which was also confirmed by endpoint visual detection (FIG. 4b and FIG. 20).

Figure 5:
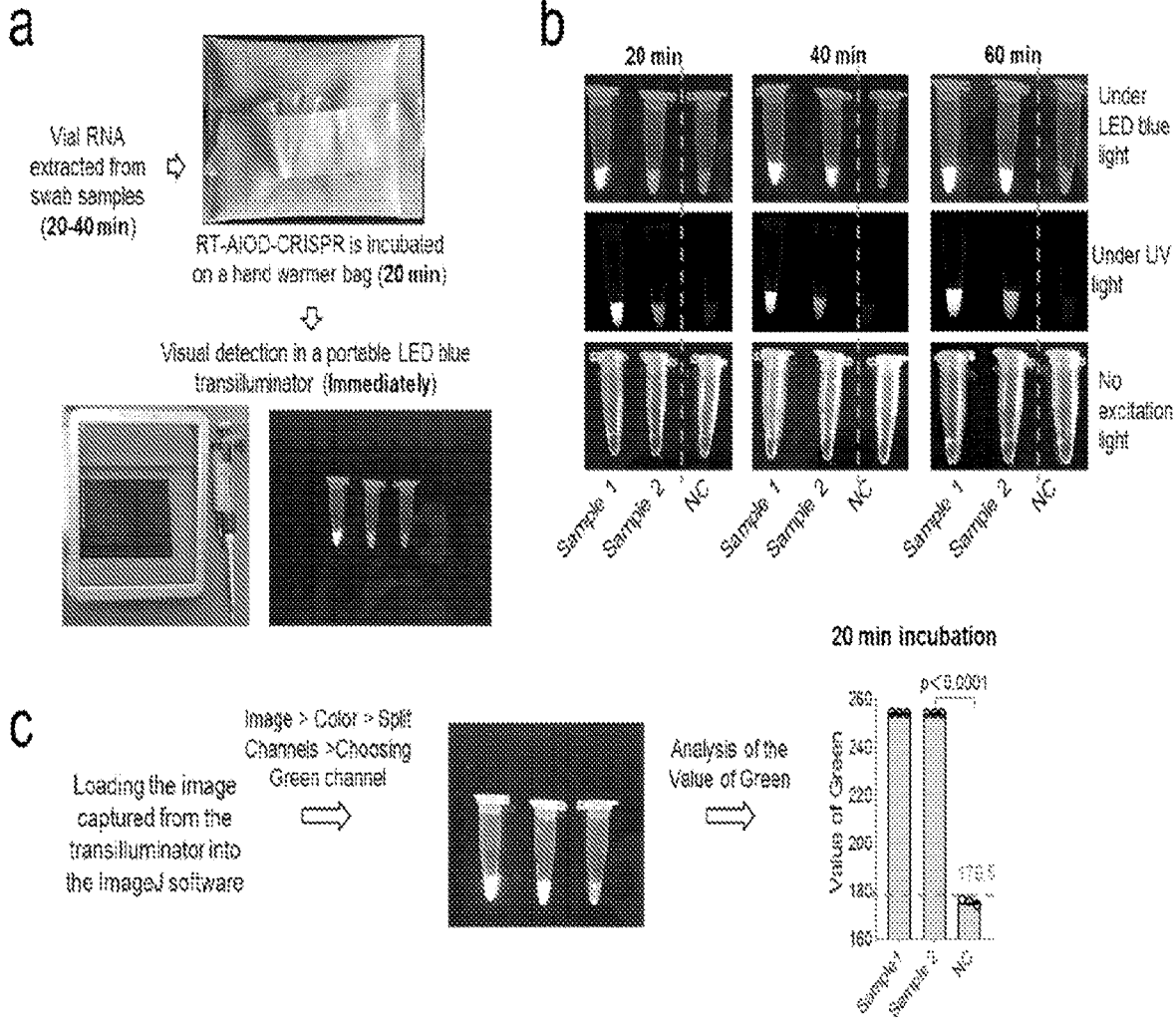
FIG. 5a-c. Instrument-free COVID-19 diagnostics by RT-AIOD-CRISPR assay, a Workflow of the instrument-free POC diagnostics. b Visual detection after 20, 40, and 60-min incubation on the hand warmer bag. c Analysis of the green value for the fluorescence image (20-min incubation) using the ImageJ™ software. The horizontal dashed line indicates the cut-off fluorescence that was defined by the average intensity of NTC plus 3 times of the standard deviation. NC, the SARS-CoV-2-negative sample. Each measuring was run with three replicates (n=3). Error bars represent the means±s.d. from replicates. The unpaired two-tailed t-test was used to analyse the statistical significance.

To further demonstrate its point of care diagnostic application, a low-cost hand warmer (~$0.3 per bag) was used as the incubator of the RT-AIOD-CRISPR assay and detect COVID-19 patient samples. As shown in FIG. 5a, the AIOD-CRISPR assay tubes were directly placed on an air-activated hand warmer without need for any electric incubator. The endpoint fluorescence result can be observed by the naked eye under LED light. FIG. 5b shows that two SARS-CoV-2-positive samples incubated in the hand warmer bag were visually detected and identified within as short as 20 min which excludes the nucleic acid extraction time. The longer the incubation time, the stronger the fluorescence signal of the positive samples. Additionally, a similar result was achieved through analyzing the green value of the fluorescence images using the ImageJ™ software (FIG. 5c). Therefore, the AIOD-CRISPR method provides a simple, rapid and visual approach for SARS-CoV-2 detection and has the potential to develop an instrument-free point of care diagnostics of the COVID-19.

Discussion

The emergence of the new coronavirus SARS-CoV-2, and its rapid spread through many countries, has been labeled as a global health emergency by the WHO. Early diagnosis of these severe infections is crucial to prevent the rapid spread of this deadly virus globally. Current PCR technology is not suitable for rapid point of care diagnostic application due to the need for specialized laboratory equipment and trained technicians. The limitations of current detection technology represent serious barriers for the real-time monitoring and detection of these highly contagious pathogens to prevent them spreading from person-to-person. Thus, there is an urgent need for a simple, easy-to-use, and inexpensive diagnostic approach.

In this study, a simple, rapid, ultrasensitive and highly specific AIOD-CRISPR assay for the detection of SARS-CoV-2 is described. This AIOD-CRISPR assay method is, to the best of our knowledge, the first system that allows all components to be incubated in one pot for CRISPR-based nucleic acid detection, enabling simple, all-in-one molecular diagnostics without need for separate and complex manual operations. The AIOD-CRISPR assay takes advantage of dual crRNAs without PAM sequence limitation to enable highly sensitive, specific and robust SARS-CoV-2 detection. Importantly, the detection results of the AIOD-CRISPR assay can be directly visualized by the naked eye, significantly simplifying the detection process and eliminating the need for separate lateral flow-based detection.

Compared existing CRISPR-based nucleic acid detection methods,[7] the versatile and robust AIOD-CRISPR assay has distinctive advantages and provides a true single reaction system. In the AIOD-CRISPR assay, the components for both isothermal amplification and CRISPR-based detection are prepared in one-pot, completely circumventing the need for separate pre-amplification of target nucleic acids, or physical separation of Cas enzyme. The AIOD-CRISPR assay enables rapid, ultrasensitive (few copies), and highly specific nucleic acid detection. While not being bound by a specific mechanism, rapid detection speed and ultrahigh sensitivity of the AIOD-CRISPR assay may be attributable to: i) the introduction of unique dual CRISPR-Cas12a detection methodology, ii) the increased concentration of ssDNA-FQ reporters, and iii) the combination of RPA amplification and CRISPR-Cas12a-based detection. Also, the AIOD-CRISPR assay showed a high specificity in the SARS-CoV-2 detection without any cross-interaction with other sequences (e.g., SARS-CoV, MERS-CoV) (FIG. 3a).

The methods disclosed herein are suitable to achieve semi-quantitative detection by quantifying endpoint fluorescence intensities. By adding AMV reverse transcriptase, the AIOD-CRISPR assay provides one-step RT-AIOD-CRISPR assay to detect RNA targets such as SARS-CoV-2 RNA, which facilitates the CRISPR-Cas12a-based RNA detection without need for the separate preparation of cDNA. To evaluate the validity and clinical applications of the AIOD-CRISPR assay, it was adapted to detect viral RNAs extracted from SARS-CoV-2 virus in nasal swab samples, achieving consistent detection results with that of RT-PCR method. Most importantly, an instrument-free AIOD-CRISPR assay for SARS-CoV-2 detection in clinical samples was successfully demonstrated by using a simple hand warmer. The cost of the AIOD-CRISPR assay is estimated ~$6 and can be significantly decreased when scaled-up for bulk production.

The AIOD-CRISPR assay may, for example, be integrated into a disposable microfluidics chip platform, enabling fully-integrated, sample to result, multiplexed detection. On one hand, all reagents of the AIOD-CRISPR assay can be lyophilized and pre-stored in a disposable microfluidic chamber, which eliminates need for cold chains and enables rapid detection outside of a laboratory setting. On the other hand, multiplexing detection can be developed by combining multiplexed microfluidics technology. Symptoms of COVID-19 are non-specific and similar to other respiratory illnesses. The present methods and compositions can be used detect and differentiate SARS-CoV-2 and other viral infections (e.g., Influenza A/B, Respiratory Syncytial Virus), for example by microfluidic-based multiplexed detection with a single sample.

Since the AIOD-CRISPR assay generates strong fluorescence signals at the endpoint, it is possible to record, analyze and report the detection results by taking advantage of ubiquitous smartphone technology. The smartphone can be programmed to take fluorescence photos, convert the images into fluorescence intensity, analyze the data, and report the qualitative/semi-quantitative test results. Further, the test results can be wirelessly transmitted to a website or remote server[40] and made available together with GPS coordinates to the patient's doctor and public health officials. This allows simple, rapid, smart, connected disease diagnostics and tracking.

In summary, the AIOD-CRISPR assay has been demonstrated to be a rapid, all-in-one, isothermal approach for nucleic acid (DNA and RNA) detection with ultrahigh sensitivity and single-base specificity. In turn, such simple and robust method has great potential in the future development of a next-generation point of care molecular diagnostics technology for the rapid detection of infectious diseases (e.g., COVID-19) at home or in small clinics.

Methods

Materials. Gel Loading Buffer II (Denaturing PAGE), PureLink™ Quick Gel Extraction Kit and TURBO™ DNA-free Kit were purchased from Thermo Fisher Scientific (Waltham, MA). EvaGreen™ dye (20×) was purchased from Biotium (Fremont, CA). TEMED, $(NH_4)_2S_2O_8$, 30% acrylamide/bis-acrylamide solution, 10×TBE Buffer, and SsoAdvanced™ Universal SYBR™ Green PCR Supermix™ were purchased from Bio-Rad Laboratories (Hercules, CA). EnGen™ Lba Cas12a (Cpf1) (100 μM), deoxynucleotide (dNTP) mix (10 mM of each), and Avian Myeloblastosis Virus (AMV) Reverse Transcriptase (10,000 units/mL) were purchased from New England BioLabs (Ipswich, MA). RNeasy MinElute Cleanup Kit was purchased from QIAGEN (Frederick, MD). RiboMAX™ Large Scale RNA Production Systems-T7 was purchased from Sigma-Aldrich (St. Louis, MO). TwistAmp Liquid Basic Kit was purchased from TwistDx Limited (Maidenhead, UK).

The LED blue light illuminator (Maestrogen UltraSlim™) was purchased from Fisher Scientific (Pittsburgh, PA). 28 de-identified clinical swab samples (including eight COVID-19 positive samples) were tested and their viral RNAs were extracted by utilizing 140 μL of each sample and eluting with 140 μL of buffer of the QIAamp™ DSP Viral RNA Mini Kit (QIAGEN N.V., Venlo, The Netherlands). These samples were screened for SARS-CoV-2 by CDC-approved RT-PCR assays (Thermo Fisher Scientific Inc., Waltham, MA) prior to the AIOD-CRISPR assays. All clinical samples were de-identified and in compliance with ethical regulations and the approval of Institutional Review Board of the University of Health Center (protocol #: P61067).

Design of primers and crRNAs. The SARS-CoV-2 target sequence was 121 bp N gene fragment with the location from 28857 to 28977 in the SARS-CoV-2's genome (GenBank accession MT688716.1). Four sites of this target sequence were used to design the primers and crRNAs of the AIOD-CRISPR assay. These sites were checked to be highly conserved by using the GISAID's data on multiple sequence alignments analysis of 4663 SARS-CoV-2 genomes (as of Aug. 14, 2020).[21] Primer design for RPA and PCR was achieved by using the publicly available tools of OligoAnalyzer™ and Realtime™ PCR, respectively. The principle of designing RPA primers referred to the TwistAmp™ Assay Design Manual. The crRNA with 20-24 nt size was also designed using the OligoAnalyzer™ and selected by against the MERS-CoV and SARS-CoV N genes. Oligonucleotides (primers and crRNAs), ssDNA-FQ reporters, the pUCIDT (Amp) plasmid with the 316 bp SARS-CoV-2 N gene sequence (from 28766 to 29081 in GenBank accession LC528233.1), and the control plasmids containing the complete N gene from SARS-CoV-2, SARS-CoV, and MERS-CoV as well as the Hs_RPP30 control were synthesized from Integrated DNA Technologies (Coralville, IA). The sequence information of all used primers and crRNAs as well as the target inserted into a plasmid has been listed in the Table 1.

TABLE 1

The sequence list of primers, crRNAs and target inserted into a plasmid

| Item | Sequence (5'-3') |
|---|---|
| The 316 bp SARS-COV-2 N gene sequence inserted into the pUCIDT (Amp) plasmid | CTCAAGGAACAACATTGCCAAAAGGCTTCTACGCAGAAGGGAGCAGAGGCG GCAGTCAAGCCTCTTCTCGTTCCTCATCACGTAGTCGCAACAGTTCAAGAA ATTCAACTCCAGGCAGCAGTAGGGGAACTTCTCCTGCTAGAATGGCTGGCA ATGGCGGTGATGCTGCTCTTGCTTTGCTGCTGCTTGACAGATTGAACCAGC TTGAGAGCAAAATGTCTGGTAAAGGCCAACAACAACAAGGCCAAACTGTCA CTAAGAAATCTGCTGCTGAGGCTTCTAAGAAGCCTCGGCAAAAACGTACTG CCACTAAAGC (SEQ ID NO: 1) |
| Forward primer (FP) targeting SARS-COV-2 N gene | AGGCAGCAGTAGGGGAACTTCTCCTGCTAGAAT (SEQ ID NO: 2) |
| Reverse primer (FP) targeting SARS-COV-2 N gene | TTGGCCTTTACCAGACATTTTGCTCTCAAGCTG (SEQ ID NO: 3) |
| Forward crRNA (crRNA1) targeting SARS-COV-2 N gene | UAAUUUCUACUAAGUGUAGAUCAUCACCGCCAUUGCCAGCC (SEQ ID NO: 4) |
| Reverse crRNA (crRNA2) targeting SARS-COV-2 N gene | UAAUUUCUACUAAGUGUAGAUUUGCUGCUGCUUGACAGAUU (SEQ ID NO: 5) |

TABLE 1-continued

| The sequence list of primers, crRNAs and target inserted into a plasmid | |
| --- | --- |
| Item | Sequence (5'-3') |
| Reverse crRNA (crRNA3) targeting SARS-COV-2 N gene T7 promotor-tagged | UAAUUUCUACUAAGUGUAGAUCUGCUGCUUGACAGAUUGAAC (SEQ ID NO: 6) |
| PCR forward primer targeting SARS-COV-2 N gene | TATACGACTCACTATAGGGACTCAAGGAACAACATTGCCA (SEQ ID NO: 7) |
| PCR reverse primer targeting SARS-COV-2 N gene | GCTTTAGTGGCAGTACGTT (SEQ ID NO: 8) |

Figure 21:
FIG. 21. Uncropped PAGE image of FIG. 1b.

AIOD-CRISPR assays. The AIOD-CRISPR system was prepared separately as Component A, B and C. Component A contained 1. Reaction Buffer, 1× Basic E-mix, 14 mM MgOAc, 320 nM each of primers, and 1.2 mM dNTPs. Component B consisted of 4 or 8 µM of ssDNA-FQ reporters and 1 Core Reaction Buffer. Component C was the Cas12a-crRNA mix with 0.64 µM each of crRNAs and 1.28 µM EnGen Lba Cas12a. The concentration in each component was calculated based on the finally assembled 25-µL AIOD-CRISPR system. In a typical AIOD-CRISPR assay, 1 µL of the target solution was mixed with 20 µL of Component A and 2.5 µL of Component B. This assembled mixture was then mixed with 1.5 µL of Component C to form final 25 µL of AIOD-CRISPR system. For RT-AIOD-CRISPR assays, most components were the same as those in the AIOD-CRISPR system above, except supplementing 0.32 U/µL AMV Reverse Transcriptase in Component A. Real-time fluorescence detection was carried out in the Bio-Rad CFX96 Touch Real-Time PCR Detection System. Visual detection was accomplished through imaging the tubes in the LED blue light illuminator or the Bio-Rad ChemiDoc® MP Imaging System with its built-in UV channel. For visual detection based on the reaction solution's color change, 8 µM of ssDNA-FQ reporters should be used. All the reactions were incubated at 37° C. for 40 min or the denoted time in figures. The endpoint fluorescence was the raw fluorescence determined by the Real-Time PCR Detection System. A saturated fluorescence intensity was the maximum intensity which the Real-Time PCR Detection System could determine. After reaction, the AIOD-CRISPR solution was mixed with isometric Gel Loading Buffer II prior to 15% denaturing PAGE with 8 M urea and gel imaging in the Imaging System. Uncropped PAGE image is shown in FIG. 21.

In vitro RNA preparation using T7 RNA polymerase. For SARS-CoV-2 N RNA preparation, the PCR system contained 1× SsoAdvanced Universal SYBR™ Green PCR Supermix™, 0.4 µM of the forward T7 promotor-tagged primers, 0.4 µM of the reverse primers, and 1.0 µL of 1.3×10⁵ copies/µL SARS-CoV-2 N plasmid solution. The thermal cycling was 2.5 min at 98° C. for initial denaturation, 35 cycles of 15 s at 95° C. for denaturation and 30 s at 60° C. for annealing and extension. The products of PCR were confirmed by agarose gel electrophoresis and Sanger sequencing. Afterwards, the products with the accurate sizes were extracted and purified using the Gel Extraction Kit. In vitro transcription was achieved through incubating the reaction system containing 8 µL of 5×T7 Transcription Buffer, 3 µL each of 100 mM rNTPs, 4 µL of the Enzyme Mix with 17 RNA polymerase, 16 µL of the gel-extracted PCR products at 37° C. for 4 h. Then, the transcription products were treated by DNase (from the TURBO™ DNA-free™ Kit) to degrading the DNA and the RNA was extracted and purified using the RNeasy MinElute Cleanup Kit. The purity and concentration of the collected nucleic acid were determined using NanoDrop One/One Microvolume UV-Vis Spectrophotometry (Thermo Fisher Scientific).

Statistics and Reproducibility. Statistical significances were analysed by using the Prism 8 (GraphPad Software, version 8.0.1). The data involving endpoint fluorescence and threshold time to positive were all displayed with error bars which represent mean±s.d. from three or more than three replicates. The unpaired two-tailed t-test was applied to investigate the differences between groups and the threshold for defining significance was based on the p value<0.05. Unless otherwise specified, each image for visual detection shown in the corresponding figure is a representative of at least two independent experiments.

REFERENCES

1. Zhu N. et al. A novel coronavirus from patients with pneumonia in China, 2019. *N. Engl. J. Med.* 382, 727-733 (2020).
2. WHO. *WHO Coronavirus Disease (COVID-19) Dashboard.* Web site covid19.who.int/ (2020).
3. Radmard S. et al. Clinical utilization of the Film Array meningitis/encephalitis (ME) multiplex polymerase chain reaction (PCR) assay. *Front. Neurol.* 10, https://doi.org/10.3389/fneur.2019.00281 (2019).
4. Cao L, et al. Advances in digital polymerase chain reaction (dPCR) and its emerging biomedical applications. *Biosens. Bioelectron.* 90, 459474 (2017).
5. Wang A M, Doyle M V, Mark D F. Quantitation of mRNA by the polymerase chain reaction. *Proc. Natl Acad. Sci. USA* 86, 9717-9721 (1989).
6. Piepenburg O. Williams C H, Stemple D L, Armes N A. DNA detection using recombination proteins. *PLoS Biol.* 4, https://doi.org/10.1371/journal.pbio.0040204 (2006).
7. Notomi T, et al. Loop-mediated isothermal amplification of DNA. *Nucleic. Acids Res.* 28. https://doi.org/10.1093/nar/28.12.e63 (2000).
8. Tian B, Minero G A S, Fock J, Dufva M, Hansen M F. CRISPR-Cas12a based internal negative control for non-specific products of exponential rolling circle amplification. *Nucleic. Acids Res.* 48. https://doi.org/10.1093/nar/gkaa017 (2020).
9. Rolando J C, Jue E, Barlow J T, Ismagilov R F. Real-time kinetics and high-resolution melt curves in single-molecule digital LAMP to differentiate and study specific and non-specific amplification. *Nucleic Acids Res.* 48, https://doi.org/10.1093/nar/gkaa099 (2020).

10. Li Y, Li S, Wang J, Liu G. CRISPR/Cas systems towards next-generation biosensing. *Trends Biotechnol.* 37, 730-743 (2019).

11. Chertow D S. Next-generation diagnostics with CRISPR. *Science* 360, 381-382 (2018).

12. Li S-Y, Cheng Q-X, Liu J-K, Nie X-Q, Zhao G-P, Wang J. CRISPR-Cas12a has both cis- and trans-cleavage activities on single-stranded DNA. *Cell Res.* 28, 491-493 (2018).

13. Chen J S, et al. CRISPR-Cas12a target binding unleashes indiscriminate single-stranded DNase activity. *Science* 360, 436-439 (2018).

14. Abudayyeh O O, et al. C2c2 is a single-component programmable RNA-guided RNA-targeting CRISPR effector. *Science* 353, https://doi.org/10.1126/science.aaf5573 (2016).

15. Li L, et al. HOLMESv2: a CRISPR-Cas12b-assisted platform for nucleic acid detection and DNA methylation quantitation. *ACS Synth. Biol.* 8, 2228-2237 (2019).

16. Jeon Y, et al. Direct observation of DNA target searching and cleavage by CRISPR-Cas12a. *Nat. Commun.* 9, https://doi.org/10.1038/s41467-018-05245-x (2018).

17. Gootenberg J S, et al. Nucleic acid detection with CRISPR-Cas13a/C2c2. *Science* 356, 438-442 (2017).

18. Broughton J P, et al. CRISPR-Cas12-based detection of SARS-CoV-2. *Nat. Biotechnol.* 38, 870-874 (2020).

19. Yang H, Gao P, Rajashankar K R, Patel D J. PAM-dependent target DNA recognition and cleavage by C2c1 CRISPR-Cas endonuclease. *Cell* 167, https://doi.org/10.1016/j.cell.2016.11.053 (2016).

20. Yeh E-C, Fu C-C, Hu L, Thakur R, Feng J, Lee L P. Self-powered integrated microfluidic point-of-care low-cost enabling (SIMPLE) chip. *Sci. Adv.* 3. https://doi.org/10.1126/sciadv.1501645 (2017).

21. GISAID. *Genomic epidemiology of hCoV-19.* Web site gisaid.org/epiflu-applications/next-hcov-19-app/(2020).

22. WHO. *Updated WHO recommendations for international traffic in relation to COVID-19 outbreak.* Web site who.int/news-room/articles-detail/updated-who-recommendations-for-international-traffic-in-relation-to-covid-19-outbreak. (2020).

23. Kralik P, Ricchi M. A basic guide to real time PCR in microbial diagnostics: definitions, parameters, and everything. *Front. Microbiol.* 8, https://doi.org/10.3389/fmicb.2017.00108 (2017).

24. Espy M, et al. Real-time PCR in clinical microbiology: applications for routine laboratory testing. *Clin. Microbiol. Rev.* 19, 165-256 (2006).

25. Cong L. et al. Multiplex genome engineering using CRISPR/Cas systems. *Science* 339, 819-823 (2013).

26. Zhou W, Hu L, Ying L, Zhao Z, Chu P K, Yu X-F. A CRISPR-Cas9-triggered strand displacement amplification method for ultrasensitive DNA detection. *Nat. Commun.* 9, https://doi.org/10.1038/s41467-018-07324-5 (2018).

27. Wang B, et al. Cas12aVDet: a CRISPR/Cas12a-based platform for rapid and visual nucleic acid detection. *Anal. Chem.* 91, 12156-12161 (2019).

28. Strohkendl I, Saifuddin F A, Rybarski J R, Finkelstein I J, Russell R. Kinetic basis for DNA target specificity of CRISPR-Cas12a. *Molecular cell* 71, 816-824. e813 (2018).

29. Kim H, et al. Enhancement of Target Specificity of CRISPR-Cas12a by Using a Chimeric DNA-RNA Guide. *Nucleic Acids Res.* https://doi.org/10.1093/nar/gkaa605 (2020).

30. Song J, Mauk M G, Hackett B A, Cherry S, Bau H H, Liu C. Instrument-free point-of-care molecular detection of Zika virus. *Anal. Chem.* 88, 7289-7294 (2016).

31. Chen D, et al. An integrated, self-contained microfluidic cassette for isolation, amplification, and detection of nucleic acids. *Biomed Aerodevices* 12, 705-719 (2010).

32. Park S, Zhang Y, Lin S, Wang T-H, Yang S. Advances in microfluidic PCR for point-of-care infectious disease diagnostics. *Biotechnol. Adv.* 29, 830-839 (2011).

33. Ferguson B S, et al. Genetic analysis of H1N1 influenza virus from throat swab samples in a microfluidic system for point-of-care diagnostics. *J. Am. Chem. Soc.* 133, 9129-9135 (2011).

34. Song J, Liu C, Mauk M G, Peng J, Schoenfeld T, Bau H H. A multifunctional reactor with dry-stored reagents for enzymatic amplification of nucleic acids. *Anal. Chem.* 90, 1209-1216 (2018).

35. Fang X, Chen H, Yu S, Jiang X, Kong J. Predicting viruses accurately by a multiplex microfluidic loop-mediated isothermal amplification chip. *Anal. Chem.* 83, 690-695 (2011).

36. Dou M, Sanjay S T, Dominguez D C, Liu P, Xu F, Li X. Multiplexed instrument-free meningitis diagnosis on a polymer/paper hybrid microfluidic biochip. *Biosens. Bioelectron.* 87, 865-873 (2017).

37. Song J. et al. Two-stage isothermal enzymatic amplification for concurrent multiplex molecular detection. *Clin. Chem.* 63, 714-722 (2017).

38. Wu D, Wu T, Liu Q, Yang Z. The SARS-CoV-2 outbreak: what we know. *Int. J. Infect. Dis.* 94, 44-48 (2020).

39. Chen W, et al. Mobile platform for multiplexed detection and differentiation of disease-specific nucleic acid sequences, using microfluidic loop-mediated isothermal amplification and smartphone detection. *Anal. Chem.* 89, 11219-11226 (2017).

40. Song J, et al. Smartphone-based mobile detection platform for molecular diagnostics and spatiotemporal disease mapping. *Anal. Chem.* 90, 48234831 (2018).

41. Yin K. et al. Synergistically enhanced colorimetric molecular detection using smart cup: a case for instrument-free HPV-associated cancer screening. *Theranostics* 9, 2637 (2019).

42. Ding X, et al. All-in-one dual CRISPR-Cas12a (AIOD-CRISPR) assay protocol for SARS-CoV-2 detection. *Protoc. Exch.* http://dx.doi.org/10.21203/rs.3.pex-1109/v1 (2020).

---

We claim:

1. A nucleic acid detection method, comprising:

(a) incubating a sample with dNTPs, ATP, a forward primer and a reverse primer that are each complementary to a target nucleic acid, a single stranded DNA fluorophore quencher (ssDNA-FQ) comprising a fluorophore and a quencher, a strand displacement DNA polymerase, single-stranded DNA binding protein, and a recombinase to form a mixture;

wherein incubating the sample results in base pairing of the forward primer and the reverse primer to the target nucleic acid if present in the sample and initiation of recombinase polymerase amplification (RPA) of the target nucleic acid in the mixture, exposing binding sites for Cas12a-crRNA complexes due to strand displacement;

(b) combining the mixture with:

(i) a forward Cas12a-crRNA complex and a reverse Cas12a-crRNA complex to form an assembled mixture, wherein the forward Cas12a-crRNA complex comprises a forward crRNA and Cas12a protein or functional analogue thereof, the reverse Cas12a-crRNA complex comprises a reverse crRNA and the Cas12a protein or functional analogue, wherein (I) the forward crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the forward primer on the opposite strand from the forward primer; and (II) the reverse crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid within 0-25, 0-20, 0-15, 0-10, or 0-5 nt of the reverse primer on the opposite strand from the reverse primer; or (ii) one or more Cas12a-crRNA complexes comprising a crRNA and Cas12a protein or functional analogue thereof to form an assembled mixture, wherein each of the one or more crRNA is between 10-100, 10-90, 10-80, 10-70, 10-60, 10-50, 10-40, 10-30, 20-100, 20-90, 20-80, 20-70, 20-60, 20-50, 20-40, 20-30, or 20-24 nt in length, and is designed to bind to the target nucleic acid between forward and reverse primer binding sites;

wherein all of the crRNAs in option (i) or (ii) each have a GC content of between about 50% and about 65%, and a melting temperature ($T_m$) of between about 56-65° C. using nearest neighbor method under the condition of 0.1 μM oligos and 1 M Na$^+$;

wherein none of the crRNAs include the protospacer adjacent motif (PAM) sequence TTTV;

wherein if the target nucleic acid is present in the mixture, combining the mixture results in binding of either:

(I) the forward Cas12a-crRNA complex and the reverse Cas12a-crRNA complex to the binding sites for Cas12a-crRNA complexes on the target nucleic acid and Cas12a endonuclease activation and cleavage of ssDNA-FQ reporters to produce fluorescence; or (II) the one or more Cas12a-crRNA complex to the binding sites for Cas12a-crRNA complexes on the target nucleic acid, and Cas12a endonuclease activation and cleavage of ssDNA-FQ reporters to produce fluorescence; and (c) detecting fluorescence emitted from the assembled mixture, wherein fluorescence emission detection indicates presence of the target nucleic acid in the sample.

2. The method of claim 1, wherein the incubating further comprises: incubating the sample with a Mg$^{2+}$ ion source and/or incubating the sample with a crowding agent and a recombinase loading agent.

3. The method of claim 2, wherein:

(a) the Mg$^{2+}$ ion source may comprise magnesium acetate, magnesium chloride, magnesium sulphate, magnesium borate, or combinations thereof and/or wherein the Mg$^{2+}$ ion source is present in the assembled mixture at a concentration between 2 mM-175 mM, 2 mM-150 mM, 2 mM-125 mM, 2 mM-100 mM, 2 mM-75 mM, 2 mM-50 mM, 2 mM-25 mM, 2 mM-20 mM, 2 mM-15 mM, 5 mM-200 mM, 5 mM-175 mM, 5 mM-150 mM, 5 mM-125 mM, 5 mM-100 mM, 5 mM-75 mM, 5 mM-50 mM, 5 mM-25 mM, 5 mM-20 mM, 5 mM-15 mM, 10 mM-200 mM, 10 mM-175 mM, 10 mM-150 mM, 10 mM-125 mM, 10 mM-100 mM, 10 mM-75 mM, 10 mM-50 mM, 10 mM-25 mM, 10 mM-20 mM, 10 mM-15 mM, 11 mM-15 mM, 12 mM-15 mM, or 13 mM-15 mM;

(b) wherein the crowding agent comprises polyethylene glycol (PEG) over 10,000 Daltons in molecular weight, or PEG of 20,000 Daltons or more in molecular weight, and wherein the crowding agent is present in the assembled mixture between 0.5%-12%, 0.5%-10%, 0.5%-7.5%, 0.5%-6%, 1%-15%, 1%-12%, 1%-10%, 1%-7.5%, 1%-6%, 2.5%-15%, 2.5%-12%, 2.5%-10%, 2.5%-7.5%, 2.5%-6%, 4%-15%, 4%-12%, 4%-10%, 4%-7.5%, or 4%-6% crowding agent on a wt/vol basis;

(c) the dNTPs are present in the assembled mixture at a concentration between 0.2 mM-3 mM, 0.2 mM-2.5 mM, 0.2 mM-2 mM, 0.2 mM-1.5 mM, 0.5 mM-3.6 mM, 0.5 mM-3 mM, 0.5 mM-2.5 mM, 0.5 mM-2 mM, 0.5 mM-1.5 mM, 0.75 mM-3.6 mM, 0.75 mM-3 mM, 0.75 mM-2.5 mM, 0.75 mM-2 mM, 0.75 mM-1.5 mM, 1 mM-3.6 mM, 1 mM-3 mM, 1 mM-2.5 mM, 1 mM-2 mM, 1 mM-1.5 mM, or 1.1 mM to 1.3 mM;

(d) the ATP is present in the assembled mixture at a concentration between 0.2 mM-8 mM, 0.2 mM-6 mM, 0.2 mM-4 mM, 0.2 mM-3.5 mM, 0.2 mM-3.1 mM, 0.5 mM-10 mM, 0.5 mM-8 mM, 0.5 mM-6 mM, 0.5 mM-4 mM, 0.5 mM-3.5 mM, 0.5 mM-3.1 mM, 1 mM-10 mM, 1 mM-8 mM, 1 mM-6 mM, 1 mM-4 mM, 1 mM-3.5 mM, 1 mM-3.1 mM, 1.5 mM-10 mM, 1.5 mM-8 mM, 1.5 mM-6 mM, 1.5 mM-4 mM, 1.5 mM-3.5 mM, 1.5 mM-3.1 mM, 2 mM-10 mM, 2 mM-8 mM, 2 mM-6 mM, 2 mM-4 mM, 2 mM-3.5 mM, 2 mM-3.1 mM, 2.5 mM-10 mM, 2.5 mM-8 mM, 2.5 mM-6 mM, 2.5 mM-4 mM, 2.5 mM-3.5 mM, 2.5 mM-3.1 mM, or 2.9 mM-3.1 mM;

(e) the forward primer and the reverse primer are each present in the assembled mixture at a concentration between 50 nM-1.6 μM, 50 nM-1 μM, 50 nM-750 nM, 50 nM-500 nM, 50 nM-400 nM, 50 nM-350 nM, 100 nM-1.6 μM, 100 nM-1 μM, 100 nM-750 nM, 100 nM-500 nM, 100 nM-400 nM, 100 nM-350 nM, 150 nM-1.6 μM, 150 nM-1 μM, 150 nM-750 nM, 150 nM-500 nM, 150 nM-400 nM, 150 nM-350 nM, 200 nM-1.6 μM, 200 nM-1 μM, 200 nM-750 nM, 200 nM-500 nM, 200 nM-400 nM, 200 nM-350 nM, 250 nM-1.6 μM, 250 nM-1 μM, 250 nM-750 nM, 250 nM-500 nM, 250 nM-400 nM, 250 nM-350 nM, 300 nM-1.6 μM, 300 nM-1 μM, 300 nM-750 nM, 300 nM-500 nM, 300 nM-400 nM, 300 nM-350 nM, or 310 nM-330 nM;

(f) wherein the ssDNA-FQ comprises fluorophore 6-FAM at 5'-end and quencher DABCYL at 3'-end and is present in the assembled mixture at a concentration of between 0.2 μM-14 μM, 0.2 μM-12 μM, 0.2 μM-10 μM, 0.2 μM-9 μM, 0.2 μM-8.5 μM, 1 μM-16 μM, 1 μM-14 μM, 1 μM-12 μM, 1 μM-10 μM, 1 μM-9 μM, 1 μM-8.5 μM, 2.5 M-16 μM, 2.5 μM-14 μM, 2.5 μM-12 μM, 2.5 μM-10 μM, 2.5 μM-9 μM, 2.5 μM-8.5 μM, 5 μM-16 μM, 5 μM-14 μM, 5 μM-12 μM, 5 μM-10 μM, 5 μM-9 μM, 5 μM-8.5 μM, 7.5 μM-16 μM, 7.5 μM-14 μM, 7.5 μM-12 UM, 7.5 μM-10 μM, 7.5 μM-9 μM, 7.5 μM-8.5 μM, 7.8 μM-8.2 μM, or 7.9 μM-8.1 μM and is between 5-30 nucleotides in length;

(g) wherein the strand displacement DNA polymerase comprises Bsu DNA polymerase and is present in the assembled mixture at a concentration between 5 ng/μL-0.75 μg/μL, 5 ng/μL-0.50 μg/μL, 5 ng/μL-0.25 μg/μL, 5 ng/μL-0.1 μg/μL, 5 ng/μL-0.5 μg/μL, 5 ng/μL-0.4 μg/μL, 10 ng/μL-1 μg/μL, 10 ng/μL-0.75 μg/μL, 10 ng/μL-0.50 μg/μL, 10 ng/μL-0.25 μg/μL, 10 ng/μL-0.1 μg/μL, 10 ng/μL-0.5 μg/μL, 10 ng/μL-0.4 μg/μL, 20 ng/μL-1 μg/μL, 20 ng/μL-0.75 μg/μL, 20 ng/μL-0.50 μg/μL, 20 ng/μL-0.25 μg/μL, 20 ng/μL-0.1 μg/μL, 20 ng/μL-0.5 μg/μL, 20 ng/μL-0.4 μg/μL, 25 ng/μL-1 μg/μL, 25 ng/μL-0.75 μg/μL, 25 ng/μL-0.50 μg/μL, 25 ng/μL-0.25 μg/μL, 25 ng/μL-0.1 μg/μL, 25 ng/μL-0.5 μg/μL, 25 ng/μL-0.4 μg/μL, 28 ng/μL-32 ng/μL, or 29 ng/μL-31 ng/μL;

(h) wherein the single-stranded DNA binding protein optionally comprises T4 gp32, Rb69 gp32, or combinations thereof and is present in the assembled mixture at a concentration between 50 ng/μL-7.5 μg/μL, 50 ng/μL-5 μg/μL, 50 ng/μL-2.5 μg/μL, 50 ng/μL-1 μg/μL, 250 ng/μL-10 μg/μL, 250 ng/μL-7.5 μg/μL, 250 ng/µL-5 µg/µL, 250 ng/µL-2.5 µg/µL, 250 ng/µL-1 µg/µL, 500 ng/µL-10 µg/µL, 500 ng/µL-7.5 µg/µL, 500 ng/µL-5 µg/µL, 500 ng/µL-2.5 µg/µL, 500 ng/µL-1 µg/µL, 750 ng/µL-10 µg/µL, 750 ng/µL-7.5 µg/µL, 750 ng/µL-5 µg/µL, 750 ng/µL-2.5 µg/µL, 750 ng/µL-1 µg/µL, or 850 ng/µL-950 ng/µL;

(i) wherein the recombinase comprises T2 UvsX, T4 UvsX, T6 UvsX, Aeh1 UvsX, Rb69 UvsX, or combinations thereof and is present in the assembled mixture at a concentration between 20 ng/µL-1 µg/µL, 20 ng/µL-0.75 µg/µL, 20 ng/µL-0.5 µg/µL, 20 ng/µL-0.25 µg/µL, 20 ng/µL-0.15 µg/µL, 50 ng/µL-5 µg/µL, 50 ng/µL-1 µg/µL, 50 ng/µL-0.75 µg/µL, 50 ng/µL-0.5 µg/µL, 50 ng/µL-0.25 µg/µL, 50 ng/µL-0.15 µg/µL, 75 ng/µL-5 µg/µL, 75 ng/µL-1 µg/µL, 75 ng/µL-0.75 µg/µL, 75 ng/µL-0.5 µg/µL, 75 ng/µL-0.25 µg/µL, 75 ng/µL-0.15 µg/µL, 100 ng/µL-5 µg/µL, 100 ng/µL-1 µg/µL, 100 ng/µL-0.75 µg/µL, 100 ng/µL-0.5 µg/µL, 100 ng/µL-0.25 µg/µL, 100 ng/µL-0.15 µg/µL, or 110 ng/µL-130 ng/µL;

(j) wherein the recombinase loading agent comprises T2 UvsY, T4 UvsY, T6 UvsY, Aeh1 UvsY, Rb69 UvsY, or combinations thereof and is present in the assembled mixture at a concentration between about 5 ng/µL-0.5 µg/µL, 5 ng/µL-0.25 µg/µL, 5 ng/µL-0.1 µg/µL, 5 ng/µL-0.075 µg/µL, 5 ng/µL-0.05 µg/µL, 10 ng/µL-1 µg/µL, 10 ng/µL-0.5 µg/µL, 10 ng/µL-0.25 µg/µL, 10 ng/µL-0.1 µg/µL, 10 ng/µL-0.075 µg/µL, 10 ng/µL-0.05 µg/µL, 20 ng/µL-1 µg/µL, 20 ng/µL-0.5 µg/µL, 20 ng/µL-0.25 µg/µL, 20 ng/µL-0.1 µg/µL, 20 ng/µL-0.075 µg/µL, 20 ng/µL-0.05 µg/µL, or 25 ng/µL-35 ng/µL;

(k) wherein the forward crRNA and the reverse crRNA are each present in the assembled mixture at a concentration of between 0.05 µM-5 µM, 0.05 µM-2.5 µM, 0.05 UM-1 µM, 0.05 µM-0.75 µM, 0.25 µM-5 µM, 0.25 µM-5 µM, 0.25 µM-2.5 µM, 0.25 µM-1 µM, 0.25 µM-0.75 µM, 0.5 µM-5 µM, 0.5 µM-5 µM, 0.5 µM-2.5 µM, 0.5 µM-1 µM, or 0.5 µM-0.75 µM; and/or (l) wherein the Cas12a is present in the assembled mixture at a concentration of between 0.01 µM-7.5 µM, 0.01 µM-5 µM, 0.01 µM-2.5 µM, 0.01 µM-2 µM, 0.1 µM-10 µM, 0.1 µM-7.5 µM, 0.1 µM-5 µM, 0.1 µM-2.5 µM, 0.1 µM-2 µM, 0.5 µM-10 µM, 0.5 µM-7.5 µM, 0.5 µM-5 µM, 0.5 µM-2.5 µM, 0.5 µM-2 µM, 0.75 µM-10 µM, 0.75 µM-7.5 µM, 0.75 µM-5 µM, 0.75 µM-2.5 µM, 0.75 µM-2 µM, 1 µM-10 µM, 1 µM-7.5 µM, 1 µM-5 µM, 1 µM-2.5 µM, 1 µM-2 µM, or 1 µM-1.5 µM.

4. The method of claim 1, wherein the forward primer and the reverse primer are designed to generate a target nucleic acid amplification product of between 100-500 base pairs in length.

5. The method of claim 1, wherein combining the mixture with forward and reverse Cas12a-crRNA complexes to generate the assembled mixture comprises:

(a) combining the mixture with pre-formed forward and reverse Cas12a-crRNA complexes, or (b) combining the mixture with the crRNAs and the Cas12a protein or functional analogue thereof, wherein the forward and reverse Cas12a-crRNA complexes form in the assembled mixture.

6. The method of claim 1, wherein the assembled mixture comprises (i) 2 mM-200 mM of the $Mg^{2+}$ ion source;

(ii) 0.5%-15% of a crowding agent on a wt/vol basis;

(iii) 0.2 mM-3.6 mM of the dNTPs;

(iv) 0.2 mM-10 mM of the ATP;

(v) 50 nM-1.6 µM each of the forward primer and the reverse primer;

(vi) 0.2 µM-16 µM of the ssDNA-FQ;

(vii) 5 ng/µL-1 µg/µL of the strand displacement DNA polymerase;

(viii) 50 ng/µL-10 µg/µL of the single-stranded DNA binding protein;

(ix) 20 ng/µL-5 µg/µL of the recombinase; and (x) 5 ng/µL-1 µg/µL of a recombinase loading agent;

(xi) 0.05 µM-5 µM each of the forward crRNA and the reverse crRNA, or each crRNA in the one or more Cas12a-crRNA complexes; and (xii) 0.01 µM-10 µM of the Cas12a protein or functional analogue thereof.

7. The method of claim 6, wherein the assembled mixture further comprises:

(xiii) a concentration between 0.5 mM-500 mM, 0.5 mM-250 mM, 0.5 mM-150 mM, 25 mM-500 mM, 25 mM-250 mM, 25 mM-150 mM, 50 mM-500 mM, 50 mM-250 mM, 50 mM-150 mM, 75 mM-500 mM, 75 mM-250 mM, 75 mM-150 mM, or 90 mM-110 mM of a $K^{2+}$ ion source comprising potassium acetate, potassium chloride, potassium sulphate, potassium borate, or combinations thereof;

(xiv) a concentration between 0.1 mM-20 mM, 0.1 mM-15 mM, 0.1 mM-10 mM, 0.1 mM-5 mM, 0.1 mM-3 mM, 0.5 mM-20 mM, 0.5 mM-15 mM, 0.5 mM-10 mM, 0.5 mM-5 mM, 0.5 mM-3 mM, 1 mM-20 mM, 1 mM-15 mM, 1 mM-10 mM, 1 mM-5 mM, or 1 mM-3 mM of dithiothreitol (DTT);

(xv) a concentration between 0.01 µg/µL-1.0 µg/µL, 0.05 µg/µL-0.5 µg/µL, 0.0.75 µg/µL-0.25 µg/µL, or 0.9 µg/µL-1.1 µg/µL of creatine kinase; and (xvi) a concentration between 0.5 mM-500 mM, 0.5 mM-250 mM, 0.5 mM-100 mM, 0.5 mM-75 mM, 5 mM-500 mM, 5 mM-250 mM, 5 mM-100 mM, 5 mM-75 mM, 20 mM-500 mM, 20 mM-250 mM, 20 mM-100 mM, 20 mM-75 mM, 40 mM-500 mM, 40 mM-250 mM, 40 mM-100 mM, 40 mM-75 mM, or 40 mM-60 mM phosphocreatine.

8. The method of claim 6, wherein the incubating step (a) comprises (I) pre-mixing components (i)-(v) to form a first pre-mixture, and (II) pre-mixing components (vi)-(x) to form a second pre-mixture, and then mixing the first pre-mixture and the second pre-mixture to form the mixture of step (a); and then combining the mixture of step (a) with components (xi)-(xii) in step (b) to form the assembled mixture.

9. The method of claim 8, wherein the first pre-mixture comprises components (i)-(vi), and (xiii)-(xvi).

10. The method of claim 1, wherein the ssDNA-FQ reporter does not anneal to the target nucleic acid.

11. The method of claim 1, wherein the assembled mixture has a pH between 7.0 and 8.5.

12. The method of claim 1, wherein the target nucleic acid comprises RNA, wherein the method further comprises incubating the sample with reverse transcriptase.

13. The method of claim 1, wherein the incubating the sample in step (a) is carried out for between 1 minute and 60 minutes, 1 minute and 45 minutes, 1 minute and 30 minutes, 1 minute and 15 minutes, 5 minutes and 60 minutes, 5 minutes and 45 minutes, 5 minutes and 30 minutes, 5 minutes and 15 minutes, 7.5 minutes and 12.5 minutes, 9 minutes and 11 minutes, or 10 minutes and/or incubating the mixture in step (b) is carried out for between 1 minute and 120 minutes, 1 minute and 90 minutes, 1 minute and 60 minutes, 10 minutes and 120 minutes, 10 minutes and 90 minutes, 10 minutes and 60 minutes, 20 minutes and 120 minutes, 20 minutes and 90 minutes, 20 minutes and 60 minutes, 30 minutes and 50 minutes, 35 minutes and 45 minutes, or 40 minutes.

14. The method of claim 1, wherein incubating the sample and incubating the mixture are carried out at between 32° C. and 43° C., or between 35° C. and 42° C.

15. The method of claim 1, wherein the target nucleic acid is a pathogen nucleic acid, nucleic acid biomarker, or tumor specific nucleic acid.

16. The method of claim 15, where the target nucleic acid is a pathogen nucleic acid, wherein the pathogen is a bacterial, viral, fungal pathogen or any other organism capable of causing disease or illness in its host.

17. The method claim 1, wherein the method comprises quantitating an amount of the target nucleic acid based on detecting fluorescence emitted from the assembled mixture.

18. The method of claim 1, wherein the assembled mixture comprises about 100 mM potassium acetate, about 14 mM magnesium acetate, about 2 mM DTT, about 5% polyethylene glycol over 10,000 Daltons in molecular weight, about 1.2 mM dNTPs, about 3 mM ATP, about 50 mM phosphocreatine, about 0.1 μg/μL creatine kinase, about 320 nM each of the forward primer and the reverse primer, about 8 μM the ssDNA-FQ reporter, about 0.03 μg/μL strand displacement DNA polymerase, about 0.9 μg/μL single-stranded DNA binding protein, about 0.12 μg/μL recombinase, about 0.03 μg/μL recombinase loading agent, about 0.64 μM each of the forward crRNA and the reverse crRNA, and about 1.28 μM of Cas12a protein or functional analogue thereof.

\* \* \* \* \*

SEQUENCE LISTING

<160> NUMBER OF SEQ ID NOS: 10

<210> SEQ ID NO 1
<211> LENGTH: 316
<212> TYPE: DNA

-continued

```
<213> ORGANISM: Artificial Sequence
<220> FEATURE:
<223> OTHER INFORMATION: Synthetic

<400> SEQUENCE: 1
ctcaaggaac aacattgcca aaaggcttct acgcagaagg gagcagaggc ggcagtcaag      60
cctcttctcg ttcctcatca cgtagtcgca acagttcaag aaattcaact ccaggcagca     120
gtaggggaac ttctcctgct agaatggctg gcaatggcgg tgatgctgct cttgctttgc     180
tgctgcttga cagattgaac cagcttgaga gcaaaatgtc tggtaaaggc caacaacaac     240
aaggccaaac tgtcactaag aaatctgctg ctgaggcttc taagaagcct cggcaaaaac     300
gtactgccac taaagc                                                     316

<210> SEQ ID NO 2
<211> LENGTH: 33
<212> TYPE: DNA
<213> ORGANISM: Artificial Sequence
<220> FEATURE:
<223> OTHER INFORMATION: Synthetic

<400> SEQUENCE: 2
aggcagcagt aggggaactt ctcctgctag aat                                   33

<210> SEQ ID NO 3
<211> LENGTH: 33
<212> TYPE: DNA
<213> ORGANISM: Artificial Sequence
<220> FEATURE:
<223> OTHER INFORMATION: Synthetic

<400> SEQUENCE: 3
ttggccttta ccagacattt tgctctcaag ctg                                   33

<210> SEQ ID NO 4
<211> LENGTH: 41
<212> TYPE: RNA
<213> ORGANISM: Artificial Sequence
<220> FEATURE:
<223> OTHER INFORMATION: Synthetic

<400> SEQUENCE: 4
uaauuucuac uaaguguaga ucaucaccgc cauugccagc c                          41

<210> SEQ ID NO 5
<211> LENGTH: 41
<212> TYPE: RNA
<213> ORGANISM: Artificial Sequence
<220> FEATURE:
<223> OTHER INFORMATION: Synthetic

<400> SEQUENCE: 5
uaauuucuac uaaguguaga uuugcugcug cuugacagau u                          41

<210> SEQ ID NO 6
<211> LENGTH: 42
<212> TYPE: RNA
<213> ORGANISM: Artificial Sequence
<220> FEATURE:
<223> OTHER INFORMATION: Synthetic

<400> SEQUENCE: 6
uaauuucuac uaaguguaga ucugcugcuu gacagauuga ac                         42
```

<210> SEQ ID NO 7
<211> LENGTH: 40
<212> TYPE: DNA
<213> ORGANISM: Artificial Sequence
<220> FEATURE:
<223> OTHER INFORMATION: Synthetic

<400> SEQUENCE: 7
tatacgactc actataggga ctcaaggaac aacattgcca                                   40

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
gctttagtgg cagtacgtt                                                          19

<210> SEQ ID NO 9
<211> LENGTH: 136
<212> TYPE: DNA
<213> ORGANISM: Artificial Sequence
<220> FEATURE:
<223> OTHER INFORMATION: Synthetic

<400> SEQUENCE: 9
ttcaactcca ggcagcagta ggggaacttc tcctgtagaa tggctggcaa tggcggtgat      60
gctgctcttg ctttgctgct gcttgacaga ttgaaccagc ttgagagcaa aatgtctggt      120
aaaaggccaa caacaa                                                            136

<210> SEQ ID NO 10
<211> LENGTH: 190
<212> TYPE: DNA
<213> ORGANISM: Artificial Sequence
<220> FEATURE:
<223> OTHER INFORMATION: Synthetic

<400> SEQUENCE: 10
tcgttcctca tcacgtagtc gcaacagttc aagaaattca actccaggca gcagtagggg      60
aacttctcct gctagaatgg ctggcaatgg cggtgatgct gctcttgctt tgctgctgct      120
tgacagattg aaccagcttg agagcaaaat gtctggtaaa ggccaacaac aacaaggcca      180
aactgtcact                                                                   190